(12) United States Patent  (10) Patent No.: US 7,067,110 B1
Gillies et al.  (45) Date of Patent: Jun. 27, 2006

(54) FC FUSION PROTEINS FOR ENHANCING THE IMMUNOGENICITY OF PROTEIN AND PEPTIDE ANTIGENS

(75) Inventors: Stephen D. Gillies, Carlisle, MA (US); Kin Ming Lo, Lexington, MA (US); John S. Wesolowski, Jr., Weymouth, MA (US)

(73) Assignee: EMD Lexigen Research Center Corp., Billerica, MA (US)

( * ) Notice: Subject to any disclaimer, the term of this patent is extended or adjusted under 35 U.S.C. 154(b) by 245 days.

(21) Appl. No.: 09/621,268

(22) Filed: Jul. 21, 2000

Related U.S. Application Data

(60) Provisional application No. 60/144,965, filed on Jul. 21, 1999.

(51) Int. Cl.
*A61K 39/395* (2006.01)

(52) U.S. Cl. .................................. 424/1.49; 424/192.1

(58) Field of Classification Search ................ 424/1.49, 424/192.1, 85.2, 134.1; 530/351, 387.1, 387.9, 530/389.1, 391.7, 391.9; 435/7.1; 930/141
See application file for complete search history.

(56) References Cited

U.S. PATENT DOCUMENTS

| | | | |
|---|---|---|---|
| 4,196,265 A | 4/1980 | Koprowski et al. | |
| 4,469,797 A | 9/1984 | Albarella | |
| 4,676,980 A | 6/1987 | Segal et al. | |
| 4,703,008 A | 10/1987 | Lin | |
| 4,816,567 A | 3/1989 | Cabilly et al. | |
| 4,946,778 A | 8/1990 | Ladner et al. | |
| 5,019,368 A | 5/1991 | Epstein et al. | |
| 5,073,627 A | 12/1991 | Curtis et al. | |
| 5,114,711 A | 5/1992 | Bell et al. | |
| 5,116,964 A | 5/1992 | Capon et al. | |
| 5,199,942 A | 4/1993 | Gillis | |
| 5,225,538 A | 7/1993 | Capon et al. | |
| 5,225,539 A | 7/1993 | Winter | |
| 5,258,498 A | 11/1993 | Huston et al. | |
| 5,314,995 A | 5/1994 | Fell, Jr. et al. | |
| 5,349,053 A * | 9/1994 | Lnadolifi | 530/351 |
| 5,359,035 A | 10/1994 | Habermann | |
| 5,441,868 A | 8/1995 | Lin | |
| 5,457,038 A | 10/1995 | Trinchieri et al. | |
| 5,514,582 A | 5/1996 | Capon et al. | |
| 5,538,866 A * | 7/1996 | Israeli et al. | |
| 5,541,087 A | 7/1996 | Lo et al. | |
| 5,543,297 A | 8/1996 | Cromlish et al. | |
| 5,547,933 A | 8/1996 | Lin | |
| 5,552,524 A | 9/1996 | Basinski et al. | |
| 5,585,089 A | 12/1996 | Queen et al. | |
| 5,601,819 A | 2/1997 | Wong et al. | |
| 5,609,846 A | 3/1997 | Goldenberg | |
| 5,618,698 A | 4/1997 | Lin | |
| 5,624,821 A | 4/1997 | Winter et al. | |
| 5,639,725 A | 6/1997 | O'Reilly et al. | |
| 5,645,835 A | 7/1997 | Fell, Jr. et al. | |
| 5,650,150 A | 7/1997 | Gillies | |
| 5,650,492 A | 7/1997 | Gately et al. | |
| 5,667,776 A | 9/1997 | Zimmerman et al. | |
| 5,679,543 A | 10/1997 | Lawlis | |
| 5,688,679 A | 11/1997 | Powell | |
| 5,691,309 A | 11/1997 | Basinski et al. | |
| 5,709,859 A * | 1/1998 | Aruffo et al. | |
| 5,719,266 A | 2/1998 | DiMarchi et al. | |
| 5,723,125 A | 3/1998 | Chang et al. | |
| 5,726,044 A | 3/1998 | Lo et al. | |
| 5,728,552 A | 3/1998 | Fujisawa et al. | 435/69.5 |
| 5,733,876 A | 3/1998 | O'Reilly et al. | |
| 5,756,349 A | 5/1998 | Lin | |
| 5,756,461 A | 5/1998 | Stephens | |
| 5,759,551 A | 6/1998 | Ladd et al. | 424/198.1 |
| 5,770,195 A | 6/1998 | Hudziak et al. | |
| 5,800,810 A | 9/1998 | Doyle et al. | 424/85.2 |
| 5,807,715 A | 9/1998 | Morrison et al. | |
| 5,827,516 A | 10/1998 | Urban et al. | 424/93.21 |
| 5,837,682 A | 11/1998 | Folkman et al. | |
| 5,843,423 A | 12/1998 | Lyman et al. | |
| 5,854,205 A | 12/1998 | O'Reilly et al. | |
| 5,856,298 A | 1/1999 | Strickland | |
| 5,858,347 A | 1/1999 | Bauer et al. | |
| 5,885,795 A | 3/1999 | O'Reilly et al. | |
| 5,886,178 A | 3/1999 | Allen et al. | |
| 5,888,772 A | 3/1999 | Okasinski et al. | |
| 5,891,680 A | 4/1999 | Lieschke et al. | |
| 5,908,626 A | 6/1999 | Chang et al. | |

(Continued)

FOREIGN PATENT DOCUMENTS

| | | |
|---|---|---|
| AU | 21725/88 | 3/1989 |
| CN | 93100115.3 | 7/1993 |

(Continued)

OTHER PUBLICATIONS

Sallusto et al (Journal of Experimntal Medicine, 1994, vol. 179, pp. 1109–1118).*

(Continued)

*Primary Examiner*—Karen A. Canella
(74) *Attorney, Agent, or Firm*—Kirkpatrick & Lockhart; Nicholson Graham LLP

(57) ABSTRACT

Disclosed herein are methods and compositions for enhancing the immunogenicity of a preselected protein or peptide antigen in a mammal. Immunogenicity is enhanced by fusing the preselected antigen to an immunoglobulin heavy chain constant region to produce an Fc-antigen fusion protein. The Fc-antigen fusion proteins bind Fc receptors on the surface of antigen presenting cells, thereby targeting the antigen to the antigen presenting cells in the mammal. In addition, disclosed is a family of adjuvants, for example, an Fc-adjuvant fusion protein, for use in combination with the Fc-antigen fusion proteins to enhance or modulate a particular immune response against the preselected antigen.

25 Claims, 14 Drawing Sheets

U.S. PATENT DOCUMENTS

| | | |
|---|---|---|
| 5,922,685 A | 7/1999 | Rakhmilevich et al. |
| 5,955,422 A | 9/1999 | Lin |
| 5,994,104 A | 11/1999 | Anderson et al. |
| 5,994,126 A | 11/1999 | Steinman et al. ............ 435/325 |
| 6,080,409 A | 6/2000 | Laus et al. ............... 424/192.1 |
| 6,086,875 A | 7/2000 | Blumberg et al. ........ 424/134.1 |
| 6,100,387 A | 8/2000 | Herrmann et al. |
| 6,169,070 B1 | 1/2001 | Chen et al. |
| 6,171,588 B1 | 1/2001 | Carron et al. |
| 6,231,536 B1 | 5/2001 | Lentz |
| 6,277,375 B1 * | 8/2001 | Ward |
| 6,284,536 B1 | 9/2001 | Morrison et al. |
| 6,335,176 B1 | 1/2002 | Inglese et al. |
| 6,340,742 B1 | 1/2002 | Burg et al. |
| 6,348,192 B1 | 2/2002 | Chan et al. |
| 6,406,689 B1 * | 6/2002 | Falkenberg et al. |
| 6,429,199 B1 * | 8/2002 | Krieg et al. .................. 514/44 |
| 6,444,792 B1 | 9/2002 | Gray et al. |
| 6,475,717 B1 | 11/2002 | Enssle et al. |
| 6,485,726 B1 | 11/2002 | Blumberg et al. |
| 6,500,641 B1 | 12/2002 | Chen et al. |
| 6,506,405 B1 | 1/2003 | Desai et al. |
| 6,551,592 B1 | 4/2003 | Lindhofer et al. |
| 6,583,272 B1 | 6/2003 | Bailon |
| 6,586,398 B1 | 7/2003 | Kinstler et al. |
| 6,617,135 B1 | 9/2003 | Gillies et al. |
| 6,646,113 B1 | 11/2003 | Dreyfuss et al. |
| 2001/0053539 A1 | 12/2001 | Lauffer et al. |
| 2002/0037558 A1 | 3/2002 | Lo et al. |
| 2002/0081664 A1 | 6/2002 | Lo et al. |
| 2002/0142374 A1 | 10/2002 | Gallo et al. |
| 2002/0146388 A1 | 10/2002 | Gillies |
| 2002/0147311 A1 | 10/2002 | Gillies et al. |
| 2002/0192222 A1 | 12/2002 | Blumberg et al. |
| 2002/0193570 A1 | 12/2002 | Gillies et al. |
| 2003/0003529 A1 | 1/2003 | Bayer |
| 2003/0012789 A1 | 1/2003 | Blumberg et al. |
| 2003/0044423 A1 | 3/2003 | Gillies et al. |
| 2003/0049227 A1 | 3/2003 | Gillies et al. |
| 2003/0105294 A1 | 6/2003 | Gillies et al. |
| 2003/0139365 A1 | 7/2003 | Lo et al. |
| 2003/0139575 A1 | 7/2003 | Gillies |
| 2003/0157054 A1 | 8/2003 | Gillies et al. |
| 2003/0166163 A1 | 9/2003 | Gillies |
| 2003/0166877 A1 | 9/2003 | Gillies et al. |
| 2004/0013640 A1 | 1/2004 | Zardi et al. |
| 2004/0033210 A1 | 2/2004 | Gillies |
| 2004/0043457 A1 | 3/2004 | Schumacher et al. |
| 2004/0053366 A1 | 3/2004 | Lo et al. |
| 2004/0072299 A1 | 4/2004 | Gillies et al. |
| 2004/0082039 A1 | 4/2004 | Gillies et al. |

FOREIGN PATENT DOCUMENTS

| | | |
|---|---|---|
| DE | 37 12985 A1 | 11/1988 |
| DE | 37 12985 | 11/1988 |
| EP | 0 158 198 A1 | 10/1985 |
| EP | 0 211 769 A2 | 2/1987 |
| EP | 0 237 019 A2 | 9/1987 |
| EP | 0 256 714 A2 | 2/1988 |
| EP | 0 294 703 A2 | 12/1988 |
| EP | 0 308 936 B1 | 3/1989 |
| EP | 0 314 317 B1 | 5/1989 |
| EP | 0 318 554 B1 | 6/1989 |
| EP | 0 319 012 A2 | 6/1989 |
| EP | 0 326 120 B1 | 8/1989 |
| EP | 0 350 230 A2 | 1/1990 |
| EP | 0 375 562 B1 | 6/1990 |
| EP | 0 396 387 A2 | 11/1990 |
| EP | 0 439 095 A2 | 7/1991 |
| EP | 0 511 747 A1 | 11/1992 |
| EP | 0 601 043 B1 | 6/1994 |
| EP | 0 640 619 A1 | 3/1995 |
| EP | 0 668 353 A1 | 8/1995 |
| EP | 0 706 799 A2 | 4/1996 |
| EP | 0 790 309 A1 | 8/1997 |
| EP | 1 088 888 A1 | 4/2001 |
| GB | 2 292 382 A | 2/1996 |
| JP | 63-267278 | 11/1988 |
| JP | 63-267296 | 11/1988 |
| WO | WO 86/01533 | 3/1986 |
| WO | WO 88/00052 | 1/1988 |
| WO | WO 88/09344 | 12/1988 |
| WO | WO 89/02922 | 4/1989 |
| WO | WO 89/09620 | 10/1989 |
| WO | WO 90/03801 | 4/1990 |
| WO | WO 91/00360 | 1/1991 |
| WO | WO 91/04329 | 4/1991 |
| WO | WO 91/08298 | 6/1991 |
| WO | WO 91/13166 | 9/1991 |
| WO | WO 91/14438 | 10/1991 |
| WO | WO 92/02240 | 2/1992 |
| WO | WO 92/08495 | 5/1992 |
| WO | WO 92/08801 | 5/1992 |
| WO | WO 92/16562 | 10/1992 |
| WO | WO 93/03157 | 2/1993 |
| WO | WO 93/10229 | 5/1993 |
| WO | WO 93/20185 | * 10/1993 |
| WO | WO 94/24160 | 10/1994 |
| WO | WO 94/25055 | 11/1994 |
| WO | WO 95/05468 | 2/1995 |
| WO | WO 95/21258 | 8/1995 |
| WO | WO 95/28427 | 10/1995 |
| WO | WO 95/31483 | * 11/1995 |
| WO | WO 96/04388 | 2/1996 |
| WO | WO 96/05309 | 2/1996 |
| WO | WO 96/08570 | 3/1996 |
| WO | WO 96/18412 | 6/1996 |
| WO | WO 96/31526 | 10/1996 |
| WO | WO 97/00317 | 1/1997 |
| WO | WO 97/00319 | 1/1997 |
| WO | WO 97/15666 | 5/1997 |
| WO | WO 97/20062 | 6/1997 |
| WO | WO 97/24137 | 7/1997 |
| WO | WO 97/24440 | 7/1997 |
| WO | WO 97/26335 | 7/1997 |
| WO | WO 97/30089 | 8/1997 |
| WO | WO 97/33617 | 9/1997 |
| WO | WO 97/33619 | 9/1997 |
| WO | WO 97/34631 | 9/1997 |
| WO | WO 97/43316 | 11/1997 |
| WO | WO 98/00127 | 1/1998 |
| WO | WO 98/06752 | 2/1998 |
| WO | WO 98/28427 | 7/1998 |
| WO | WO 98/30706 | 7/1998 |
| WO | WO 98/46257 | 10/1998 |
| WO | WO 98/59244 | 12/1998 |
| WO | WO 99/02709 | 1/1999 |
| WO | WO 99/03887 | 1/1999 |
| WO | WO 99/29732 | 6/1999 |
| WO | WO 99/43713 | 9/1999 |
| WO | WO 99/52562 | 10/1999 |
| WO | WO 99/53958 | 10/1999 |
| WO | WO 99/60128 | 11/1999 |
| WO | WO 99/62944 | 12/1999 |
| WO | WO 99/66054 | 12/1999 |
| WO | WO 00/11033 | 3/2000 |
| WO | WO 00/24893 | 5/2000 |
| WO | WO 00/34317 | 6/2000 |
| WO | WO 00/40615 | 7/2000 |
| WO | WO 00/68376 | 11/2000 |

| | | |
|---|---|---|
| WO | WO 00/69913 | 11/2000 |
| WO | WO 00/78334 A1 | 12/2000 |
| WO | WO 01/07081 A1 | 2/2001 |
| WO | WO 01/10912 A1 | 2/2001 |
| WO | WO 01/36489 A2 | 5/2001 |
| WO | WO 01/58957 A2 | 8/2001 |
| WO | WO 02/02143 A2 | 1/2002 |
| WO | WO 02/066514 A2 | 8/2002 |
| WO | WO 02/072605 A2 | 9/2002 |
| WO | WO 02/079232 A2 | 10/2002 |
| WO | WO 02/079415 A2 | 10/2002 |
| WO | WO 02/090566 A2 | 11/2002 |
| WO | WO 03/015697 A2 | 2/2003 |
| WO | WO 03/048334 A2 | 6/2003 |
| WO | WO 03/077834 A2 | 9/2003 |

OTHER PUBLICATIONS de La Salle et al ('FcgR on Humna Dendritic Cells' In:Human IgG Receptors, 1996, pp. 39–55, Van de Winkel et al Eds).*

Hurn and Chantler (Methods in Enzymology, 1980, vol. 70, pp. 104–142).*

Schlom (In: Molecular Foundations of Oncology, 1991, pp. 95–133).*

Heijnen et al, Journal of Clinical Investigation, 1996, vol. 97, pp. 331–338.*

Liu et al (Blood, 1998, vol. 92, pp. 3730–3736).*

Roitt et al (Immunology (text), 1993, p. 8.4.*

Harvill ET, Flemming JF, Morrison SL. I Immunol. Oct. 1, 1996, 157(7):3165–70. In vivo properties of an IgG3–IL–2 fusion protein: A general approach for immune potentiation.*

Chapman et al., (1994), "Mapping Effector Functions of a Monoclonal Antibody to GD3 by Characterization of a Mouse–Human Chimeric Antibody," *Cancer Immuno. Immunother.*, 39:198–204.

Cruse et al., (eds.), (1995), *Illustrated Dictionary of Immunology*, p. 158, CRC Press, NY.

Dorai et al., (1991), "Aglycosylated Chimeric Mouse/Human IgG1 Antibody Retains Some Effector Function," *Hybridoma*, 10(2):211–217.

Dorai et al., (1992), "Role of Inter–Heavy and Light Chain Disulfide Bonds in the Effector Functions of Human IgG1," *Molecular Immunology*, 29(12):1487–1491.

Elliott et al.,(1996), "Fine–Structure Epitope Mapping of Antierythropoietin Monoclonal Antibodies Reveals a Model of Recombinant Human Erythropoietin Structure," *Blood*, 87(7):2702–2713.

Gillies et al., (1991), "Targeting Human Cytotoxic T Lymphocytes to Kill Hererologous Epidermal Growth Factor Receptor–Bearing Tumor Cells: Tumor–Infiltrating Lymphocyte/Hormone Receptor/Recombinant Antibody," *J. Immunology*, 146(3):1067–1071.

Handgretinger et al., (1995), "A Phase I Study of Human/Mouse Chimeric Anti–ganglioside GD2 Antibody ch14.18 in Patients with Neuroblastoma," *European J. Cancer*, 31 A(2):261–267.

Isenman et al., (1975), "The Structure and Function of Immunoglobulin Domains: II. The Importance of Interchain Disulfide Bonds and the Possible Role of Molecular Flexibility in the Interaction between Immunoglobulin G and Complement," *J. Immunology*, 114(6):1726–1729.

Lo et al., (1992), "Expression and Secretion of an Assembled Tetrameric CH2–deleted Antibody in *E. coli.*," *Hum. Antibod. Hybridomas*, 3:123–128.

Maecker et al., (1997), "DNA Vaccination with Cytokine Fusion Constructs Biases the Immune Response to Ovalbumin," *Vaccine*, 15(15):1687–1696.

Mueller et al., (1990), "Enhancement of Antibody–Dependent Cytotoxicity With A Chimeric Anti–GD2 Antibody," *J. Immunology*, 144(4):1382–1386.

Mueller et al., (1990), "Serum Half–Life and Tumor Localization of a Chimeric Antibody Deleted of the CH2 Domain and Directed Against the Disialoganglioside GD2," *Proc. Natl. Acad. Sci. USA.*, 87:5702–5705.

Naramura et al., (1993), "Therapeutic Potential of Chimeric and Murine Anti–(Epidermal Growth Factor Receptor) Antibodies in a Metastasis Model for Human Melanoma," *Cancer Immuno. Immunother.*, 37:343–349.

Reisfeld et al., (1994), "Potential of Genetically Engineered Anti–Ganglioside GD2 Antibodies for Cancer Immunotherapy," *Prog. Brain Res.*, 101:201–212.

Saleh et al., (1992), "Phase I Trial of the Chimeric Anti–GD2 Monoclonal Antibody ch14.18 in Patients With Malignant Melanoma," *Hum. Antibod. Hybridomas*, 3:19–24.

Wen et al., (1994), "Erythropoietin Structure–Function Relationships: Identification of Functionally Important Domains," *J. Biological Chemistry*, 269(36):22839–22846.

Ghetic et al., (1997), "FcRn: the MNC class I–related receptor that is more than an IgG transporter," *Immunology Today*, 18(12):592–598.

Junghans et al., (1996), "The protection receptor for IgG catabolism is the $\beta_2$–microglobulin–containing neonatal intestinal transport receptor," *Proc. Natl. Acad. Sci. USA*, 93:5512–5516.

Takai, (2002), "Roles of Fc Receptors in Autoimmunity," *Nat. Rev. Immunol.*, 2(8)580–592.

Zhu et al., (2001), "MHC Class I–Related Neonatal Fc Receptor for IgG Is Functionally Expressed in Monocytes, Intestinal Macrophages, and Dendritic Cells," *J. Immunology*, 166:3266–3276.

Boissel et al., (1993), "Erythropoietin Structure–Function Relationships," *The Journal of Biological Chemistry*, 268:15983–15993.

Wen et al., (1993), "Erythropoietin Structure–Function Relationships: High Degree of Sequence Homology Among Mammals," *Blood*, 82:1507–1516.

Angal et al. (1993), "A Single Amino Acid Substitution Abolishes the Heterogeneity of Chimeric Mouse/Human (IgG4) Antibody," *Molecular Immunology*, 30:105–108.

Bitonti et al. (2002), "Transepithelial Absorption of an Erythropoietin–Fc Fusion Protein After Delivery to the Central Airways," *Respiratory Drug Delivery*, 8:309–312.

Darling et al. (2002), "Glycosylation of Erythropoietin Affects Receptor Binding Kinetics: Role of Electrostatic Interactions," *Biochemistry*, 41:14524–14531.

Fibi et al. (1995), "N– and O–Glycosylation Muteins of Recombinant Human Erythropoietin Secreted From BHK–21 Cells," *Blood*, 85:1229–1236.

Hammerling et al. (1996), "In vitro bioassay for human erythropoietin based on proliferative stimulation of an erythroid cell line and analysis of carbohydrate–dependent microheterogeneity," *Journal of Pharmaceutical and Biomedical Analysis*, 14:1455–1469.

Kitamura et al. (1989), "Establishment and Characterization of a Unique Human Cell Line that Proliferates Dependently on GM–CSF, IL–3, or Erythropoietin," *Journal of Cellular Physiology*, 140:323–334.

Locatelli et al. (2001), "Darbepoetin alfa Amgen," *Current Opinion in Investigational Drugs*, 2:1097–1104.

Spiekermann et al. (2002), "Receptor–mediated Immunoglobulin G Transport Across Mucosal Barriers in Adult Life: Functional Expression of FcRn in the Mammalian Lung," *J. Exp. Med.*, 196:303–310.

Syed et al. (1998), "Efficiency of signalling through cytokine receptors depends critically on receptor orientation," *Nature*, 395:511–516.

U.S. Appl. No. 07/348,237 filed May 5, 1989, Rosenblum et al.

Abaza et al., (1992), "Effects of Amino Acid Substitutions Outside an Antigenic Site on Protein Binding to Monoclonal Antibodies of Predetermined Specificity Obtained by Peptide Immunization," *Journal of Protein Chemistry*, 11:5:433–444.

Abstract XP–002116766, (1996), "Prostaglandins, their inhibitors and cancer," *Prostaglandins, Leukotrienes and Essential Fatty Acids*, 54:2:83–94.

Afonso et al., (1994), "The Adjuvant Effect of Interleukin–12 in a Vaccine Against Leishmania Major," *Science*, 263:235–237.

Arenberg et al. (1996), "Interferon–γ–inducible Protein 10 (IP–10) Is an Angiostatic Factor That Inhibits Human Non–small Cell Lung Cancer (NSCLC) Tumorigenesis and Spontaneous Metastases," *J. Exp. Med*, 184:981–992.

Bacha et al., (1988), "Interleukin 2 Receptor–Targeted Cytotoxicity Interleukin 2 Receptor–mediated Action of a Diphtheria Toxin–related Interleukin 2 Fusion Protein," *J. Experimental Medicine*, 167:612–622.

Bachelot et al., (Mar. 1998), "Retrovirus–Mediated Gene Transfer of an Angiostatin–Endostatin Fusion protein with Enhanced Anti–Tumor Properties In Vivo," *Proceedings of the Annual Meeting of the American Association for Cancer Research*, 39:271, Abstract #1856.

Barnett et al., (1994), "Purification, characterization and selective inhibition of human prostaglandin G/H synthase 1 and 2 expressed in the baculovirus system," *Biochimica et Biophysica Acta*, 1209:130–139.

Baselga, et al., (1998), "Recombinant Humanized Anti–HER2 Antibody (Herceptin ™) Enhances the Antitumor activity of Paclitazel and Doxorubicin against HER3/neu Overexpressing Human Breast Cancer Xenografts," *Cancer Research*, 58:2825–2831.

Batova et al., (1999), "The Ch 14.18–GM–CSF Fusion Protein Is Effective at Mediating Antibody–dependent Cellular Cytotoxicity and Complement–dependent Cytotoxicity in Vitro," *Clinical Cancer Research*, 5:4259–4263.

Batra et al., (1993), "Insertion of Constant Region Domains of Human IgG1 into CD4–PE40 Increases Its Plasma Half–Life," *Mol. Immunol.*, 30:379–386.

Becker et al., (1996), "An Antibody–Interleukin 2 Fusion Protein Overcomes Tumor Heterogeneity by Induction of a Cellular Immune Response," *Proc. Natl. Acad. Sci.*, 93:7826–7831.

Becker et al., (1996), "Eradication of human hepatic and polmonary melanoma metastases in SCID mice by antibody–interleukin 2 fusion proteins," *Proc. Natl. Acad. Sci. USA*, 93:2702–2707.

Beutler et al., (1988), "Tumor Necrosis, Cachexia, Shock, and Inflammation: A Common Mediator," *Ann. Rev. Biochem.*, 57:505–518.

Bissery et al., (1997), "The Taxoids," in *Cancer Therapeutics: Experimental and Clinical Agents*, Teicher, ed., 175–193.

Bjorn et al., (1985), "Evaluation of Monoclonal Antibodies for the Development of Breast Cancer Immunotoxins," *Cancer Research*, 45:1214–1221.

Boehm et al., (1997), "Antiagiogenic therapy of experimental cancer does not induce acquired drug resistance," *Nature*, 390:404–407.

Boehm et al., (1998), "Zinc–Binding of Endostatin Is Essential for Its Antiangiogenic Activity," *Biochemical and Biophysical Research Communications*, 252:190–194.

Brooks et al., (1994), "Integrin $\alpha_v\beta_3$ Antagonists Promote Tumor Regression by Inducing Apoptosis of Angiogenic Blood Vessels," *Cell*, 79:1157–1164.

Buchli et al., (1993), "Structural and Biologic Properties of a Human Aspartic Acid–126 Interleukin–2 Analog," *Archives of Biochemistry and Biophysics*, 307:2:411–415.

Burgess et al., (1990), "Possible Dissociation of the Heparin–binding and Mitogenic Activities of Heparin–binding (Acidic Fibroblast) Growth Factor–1 from Its Receptor–binding Activities by Site–directed Mutagenesis of a Single Lysine Residue," *Journal of Cell Biology*, 111:2129–2138.

Canfield et al., (1991), "The Binding Affinity of Human IgG for its High Affinity Fc Receptor is Determined by Multiple Amino Acids in the CH2 Domain and Is Modulated by the Hinge Region," *Journal of Experimental Medicine*, 173:6:1482–1491.

Cao et al., (1996), "Kringle Domains of Human Angiostatin," *The Journal of Biological Chemistry*, 271:46:29461–29467.

Cao et al., (1997), "Kringle 5 of Plasminogen is a Novel Inhibitor of Endothelial Cell Growth," *The Journal of Biological Chemistry*, 272:36:22924–22928.

Capon et al., (1989), "Designing CD4 immunoadhesins for AIDS therapy," *Nature*, 337:525–531.

Caton et al., (1986), "Structural and functional implications of a restricted antibody response to a defined antigenic region on the influenza virus hemagglutinin," *The EMBO Journal*, 5:7:1577–1587.

Chan et al., (1991), "Induction of Interferon γ Production by Natural Killer Cell Stimulatory Factor: Characterization of the Responder Cells and Synergy with Other Inducers," *J. Exp. Med.*, pp. 869–879.

Chang et al., (1989), "Overview of Interleukin–2 as an Immunotherapeutic Agent," *Seminars in Surgical Oncology*, 5:385–390.

Chang et al., (1996), "A Point Mutation in Interleukin–2 that Alters Ligand Internalization," *Journal of Biological Chemistry*, 271:23:13349–13355.

Chaudhary et al., (1988), "Selective killing of HIV–infected cells by recombinant human CD4–Pseudomonas exotoxin hybrid protein," *Nature*, 335:370–372.

Chaudhary et al., (1989), "A recombinant immunotoxin consisting of two antibody variable domains fused to Pseudomonas exotoxin," *Nature*, 339:394–397.

Chen et al., (1997), "Eradication of Murine Bladder Carcinoma by Intratumor Injection of a Bicistronic Adenoviral Vector Carrying cDNAs for the IL–12 Heterodimer and Its Inhibition by the IL–12 p40 Subunit Homodimer," *Journal of Immunology*, 159:1:351–358.

Cheon et al., (1994), "High–affinity binding sites for related fibroblast growth factor ligands reside within different receptor immunoglobulin–like domains," *Proc. Natl. Acad. Sci. USA*, 91: 989–993.

Chuang et al., (1993), "Effect of new investigational drug taxol on oncolytic activity and stimulation of human lymphocytes," *Gyncol. Oncol.*, 49:291–298.

Cohen, S. L. et al., (1996), "Human leptin characterization," *Nature*, 283:589.

Cole et al., (1997), "Human IgG2 Variants of Chimeric Anti–CD3 Are Nonmitogenic to T Cells," *Journal of Immunology*, 159:3613–3621.

Collins et al., (1988), "Identification of Specific Residues of Human Interleukin 2 that Affect Binding to the 70–kDa Subunit (p70) of the Interleukin 2 Receptor," *Proc. Natl. Acad. Sci*, 85:7709–7713.

Colombo et al., (1996), "Amount of Interleukin 12 Available at the Tumor Site is Critical for Tumor Regression," *Cancer Research*, 56:2531–2534.

D'Amato et al., (1994), "Thalidomide is an inhibitor of angiogenesis," *Proc. Natl. Acad. Sci. USA*, 91:4082–4085.

D'Andrea et al., (1992), "Production of Natural Killer Cell Stimulatory Factor (Interleukin 12) by Peripheral Blood Mononuclear Cells," *J. Exp. Med.*, 176:1387–1398.

Ding et al., (1988), "Zinc–Dependent Dimers Observed in Crystals of Human Endostatin," *Proceedings of the National Academy of Sciences of USA*, 95:10443–10448.

Earnest et al., (1992), "Piroxicam and Other Cyclooxygenase Inhibitors: Potential for Cancer Chemoprevention," *J. Cell. Biochem. Supp*, 161:156–166.

Eisenthal, (1990), "Indomethacin up–regulated the generation of lymphokine–activated killer–cell activity and antibody–dependent cellular cytotoxicity mediated by interleukin–2," *Cancer Immunol. Immunotherap.* 31:342–348.

Fell et al., (1991), "Genetic Construction and Characterization of Fusion Protein Consisting of a Chimeric F(ab') with Specificity for Carcinomas and Human IL–2," *The J. of Immunology*, 146:7:2446–2452.

Fell et al., (1992), "Chimeric L6 antitumor antibody," *The J. of Biol. Chem.*, 267:15552–15558.

Friedman, J. M. et al., (1998), "Leptin and the regulation of body weight in mammals," *Nature*, 395:763–770.

Gasson et al., (1984), "Purified Human Granulocyte Macrophage Colony–Stimulating Factor: Direct Action on Neutrophils," *Science*, 226:1339–1342.

Gately et al., (1998), "The Interleukin–12/Interleukin–12 Receptor system: Role in Normal and Pathologic Immune Responses," *Annu. Rev. Immunol.*, 16:495–521.

Gillessen et al., (1995), "Mouse Interleukin–12 (IL–12) p40 Homodimer: A Potent IL–12 Antagonist," *Eur. J. Immunol.*, 25:200–206.

Gillies et al., (1989), "Expression of Human Anti–Tetanus Toxoid Antibody in Transfected Murine Myeloma Cells," *Bio/Technology*, 7:799–804.

Gillies et al., (1989), "High–Level Expression of Chimeric Antibodies Using Adapted cDNA Variable Region Cassettes," *J. Immunol. Methods*, 125:191–202.

Gillies et al., (1990), "Antigen binding and biological activities of engineered mutant chimeric antibodies with human tumor specificities," *Hum. Antibod. Hybridomas*, 1:1:47–54.

Gillies et al., (1992), "Antibody–Targeted Interleukin 2 Stimulates T–Cell Killing of Autologous Tumor Cells," *Proc. Natl. Acad. Science*, 89:1428–1432.

Gillies et al., (1993), "Biological Activity and In Vivo Clearance of Antitumor Antibody/Cytokine Fusion Proteins," *Bioconjugate Chem.*, 4:230–235.

Gillies et al., (1998), "Antibody–IL–12 fusion proteins are effective in SCID mouse models of prostate and colon carcinoma matastases," *J. Immunology*, 160:2:6195–6203.

Gillies et al., (1999), "Improving the Efficacy of Antibody–Interleukin 2 Fusion Proteins by Reducing Their Interaction with Fc Receptors," *Cancer Research*, 59:2159–2166.

Gillis et al., (1978), "T Cell Growth Factor: Parameters of Production And A Quantitative Microassay for Activity," *Journal of Immunology*, 120:6:2027–2032.

Goeddel et al., (1986), "Tumor Necrosis Factors: Gene Structure and Biological Activities," *Pharm. Sciences*, pp. 597–609.

Gren et al., (1983), "A New Type of Leukocytic Interferon," *Dokl. Biochem.*, 269:91–95.

Griffon–Etienne et al., (1999), "Taxane–induced apoptosis decompresses blood vessels and lowers interstitial fluid pressure in solid tumors: clinical implications," *Cancer Research*, 59:3776–3782.

Grimaldi et al., (1989), "The t(5;14) Chromosomal Translocation in a Case of Acute Lymphocytic Leukemia Joins the Interleukin–3 Gene to the Immunoglobulin Heavy Chain Gene," *Blood*, 73:8:2081–2805.

Harris et al., (1993), "Therapeutic Antibodies—the Coming of Age," *Tibtech*, 11:42–44.

Harvill et al., (1995), "An IgG3–IL2 Fusion Protein Activates Complement, Binds FcYRI, Generates LAK Activity and Shows Enhanced Binding to the High Affinity IL–2R," *Immunotech.*, 1:95–105.

Harvill et al., (1996), "In vivo properties of an IgG3–IL–2 fusion protein: A general strategy for immune potentiation," *Journal of Immunology*, 157:7:3165–3170.

Hazama et al., (1993), "Adjuvant–Independent Enhanced Immune Responses to Recombinant Herpes Simplex Virus Type 1 Glycoprotein D by Fusion with Biologically Active Interleukin–2," *Vaccine*, 11:6:629–636.

He et al., (1998), "Humanization and Pharmacokinetics of Monoclonal Antibody with Specificity for Both E–and P–Selectin," *J. Immunol.*, 1029–1035.

Heinzel et al., (1997), "In Vivo Production and Function of IL–12 p40 Homodimers," *J. Immunol.*, 158:4381–4388.

Hellstrom et al., (1986), "Antitumor effects of L6, and IgG2a antibody the reacts with most human carcinomas," *Proc. Natl. Acad. Sci.*, 83:18: 7059–7063.

Henkart, (1985), "Mechanism of Lymphocyte–Mediated Cytotoxicity," *Ann. Rev. Immunol.*, 3:31–58.

Herrmann et al., (1989), "Hematopoeitic Responses With Advanced Malignancy Treated With Recombinant Human Granulocyte–Macrophage Colony–Stimulating Factor," *Journal of Clinical Oncology*, 7:2:159–167.

Hohenester et al., (1998), "Crystal Structure of the Angiogenesis Inhibitor Endostatin at 1.5 Å Resolution," *EMBO Journal*, 17:6:1656–1664.

Holden et al., (2001), "Augmentation of Anti–Tumor Activity of KS–IL2 Immunocytokine with Chemotherapeutic Agents," *Proceedings of the American Association for Cancer Research*, 42:683, Abstract No. 3675.

Holden et al., (2001), "Augmentation of Antitumor activity of an Antibody–Interleukin 2 Immunocytokine with Chemotherapeutic Agents," *Clinical Cancer Research*, 7:2862–2869.

Hoogenboom et al., (1991), "Construction and expression of antibody–tumor necrosis factor fusion proteins," *Molecular Immunology*, 28:9:1027–1037.

Hoogenboom et al., (1991), "Targeting of Tumor Necrosis Factor to Tumor Cells Secretion by Myeloma Cells of a Genetically Engineered Antibody–Tumor Necrosis Factor Hybrid Molecule," *Biochim. and Biophys. Acta*, 1096:4:345–354 (Abstract).

Homick et al, (1999), "Pretreatment with a monoclonal antibody/interleukin–2 fusion protein directed against DNA enhaances the delivery of therapeutic molecules to solid tumors," *Clin. Cancer Res.*, 5:51–60.

Hu et al., (1996), "A Chimeric Lym–1/Interleukin 2 Fusion Protein for Increasing Tumor Vascular Permeability and Enhancing Antibody Uptake[1]," *Cancer Research*, 56:4998–5004.

Huck et al., (1986), "Sequence of a human immunogolbulin gamma 3 heavy chain constant region gene: comparison with the other human Cγ genes," *Nucleic Acids Research*, vol. 14:4:1779–1789.

Huse et al., (1989), "Generation of a Large Combinatorial Library of the Immunoglobulin Repertoire in Phage Lambda," *Science*, 246:1275–1281.

Ingber et al., (1990), "Synthetic analogues of fumagillin that inhibit angiogenesis and suppress tumour growth," *Nature*, 348:555–557.

Jones et al., (1986), "Replacing the complementarity–determining regions in a human antibody with those from a mouse," *Nature*, 321:6069:522–525.

Ju et al., (1987), "Structure–Function Analysis of Human Interleukin–2," *Journal of Biological Chemistry*, 262:12:5723–5731.

Jung et al., (1986), "Activation of human peripheral blood mononuclear cells by anti–T3: Killing of tumor target cells coated with anti–target–anti–T3 conjugates," *Proc. Natl. Acad. Sci.*, 83:4479–4483.

Junghans et al., (1996), "The protection receptor of IgG catabolism is the B2–micorgobulin–containing neonatal intestinal transport receptor," *Proc. Natl. Acad. Sci.*, 93:11:5512–5516.

Kang et al., (1991), "Antibody redesign by chain shuffling from random combinatorial immunoglobulin libraries," *Proc. Natl. Acad. Sci.*, 88:11120–11123.

Kappel et al., (1992), "Regulating gene expression in transgenic animals," *Current Opinion in Biotechnology* 3:548–553.

Karpovsky et al., (1984), "Production of Target–Specific Effector Cells using Hetero–Cross Linked Aggregate Containing Anti–Target Cell and AntiFcλ Receptor Antibodies," *Journal of Experimental Medicine*, 160:6:1686–1701.

Kendra et al., (1999), "Pharmacokinetics and Stability of the ch 14.18–Interleukin–2 Fusion Protein in Mice," *Cancer Immunol. Immunotherapy*, 48:219–229.

Kim et al., (1997), "An Ovalbumin–IL–12 fusion protein is more effective than ovalbumin plus free recombinant IL–12 in inducing a T helper cell type 1–dominated immune response and inhibiting antigen–specific IgE production," *Journal Immunology*, 158:9:4137–4144.

Kim et al., (1999), "Cytokine Molecular Adjuvants Modulate Immune Responses Induced by DNA Vaccine Constructs for HIV–1 and SIV," *Journal of Interferon and Cytokine Research*, 19:77–84.

Kranz et al., (1984), "Attachment of an anti–receptor antibody to non–target cells renders them susceptible to lysis by a clone of cytotoxic T lymphocytes," *Proc. Natl. Acad. Sci.*, 81:7922–7926.

Kuo et al., (2001), "Oligomerization–dependent Regulation of Motility and Morphogenesis by the Collagen XVIII NC1/Endostatin Domain," *Journal of Cell Biology*, 152:6:1233–1246.

LaVallie et al., (1993), "Cloning and Functional Expression of a cDNA Encoding the Catalytic Subunit of Bovine Enterokinase," *Journal of Biological Chemistry*, 268:31:23311–23317.

Lazar et al., (1988), "Transforming Growth Factor α: Mutation of Aspartic Acid 47 and Leucine 48 Results in Different Biological Activities," *Molecular and Cellular Biology*, 8:3:1247–1252.

LeBerthon et al., (1991), "Enhanced Tumor Uptake of Macromolecules Induced by a Novel Vasoactive Interleukin 2 Immunoconjugate," *Cancer Research*, 51:2694–2698.

Lieschke, et al., (1997), "Bioactive murine and human interleukin–12 fusion proteins which retain antitumor activity in vivo," *Nature Biotechnology*, 15:1:35–40.

Linsley et al., (1991), "CTLA–4 is a Second Receptor for B Cell Activation Antigen B7," *Journal of Experimental Medicine*, 174:3:561–569.

Liu et al., (1985), "Heteroantibody Duplexes Target Cells for Lysis by Cytotoxic T Lymphocytes," *Proc. Natl. Acad. Sci.*, 82:8648–8652.

Liu et al., (1988), "Hormone Conjugated with Antibody to CD3 Mediates Cytotoxic T Cell Lysis of Human Melanoma Cells," *Science*, 239:395–398.

Lode et al., (1998), "Immunocytokines: a promising approach to cancer immunotherapy," *Pharmacol. Thera.*, 80:3:277–292.

Lode et al., (1998), "Natural Killer Cell–Mediated Eradication of Neuroblastoma Metastases to Bone Marrow by Targeted Interleukin–2 Therapy," *Blood*, 91:5:1706–1715.

Lode et al., (1999), "Synergy between an antiangiogenic integrin $α_v$ antagonist and an antibody–cytokine fusion protein eradicates spontaneous tumor metastases," *Proc. Natl. Acad. Sci.*, 96:1591–1596.

Lode et al., (1999), "Tumor–targeted IL–2 amplifies T cell–mediated immune response induced by gene therapy with single–chain IL–12," *Proc. Natl. Acad. Sci.*, 96:8591–8596.

Lode et al., (2000), "Amplification of T Cell Mediated Immune Responses by Antibody–Cytokine Fusion Proteins," *Immunological Investigations*, 29:2:117–120.

Maloney et al., (1994), "Phase I Clinical Trial Using Escalating Single–Dose Infusion of Chimeric Anti–CD20 Monoclonal Antibody (IDEC–C2B8) in Patients with Recurrent B–Cell Lymphoma," *Blood*, 84:8:2457–2466.

Mark et al., (1992), "Expression and characterization of hepatocyte growth factor receptor–IgG fusion proteins," *Journal of Biological Chemistry*, 267:36:26166–26171.

Martinotti et al., (1995), "CD4 T Cells Inhibit in vivo the CD8–Mediated Immune Response Against Murine Colon Carcinoma Cells Transduced with Interleukin–12 Genes," *Eur. J. Immunol.* 25:137–146.

Medesan et al., (1997), "Delineation of the Amino Acid Residues Involved in Transcytosis and Catabolism of Mouse IgG1[1]," *J. Immunology*, 158:5:2211–2217.

Mestre et al., (1997), "Retinoids Suppress Epidermal Growth Factor–induced Transcription of Cyclooxygenase–2 in Human Oral Squamous Carcinoma Cells," *Cancer Research*, 57:2890–2895.

Mosmann et al., (1989), "TH1 and TH2 CELLS: Different Patterns of Lymphokine Secretion Lead to Different Functional Properties," *Ann. Rev. Immunol.* 7:145–173.

Mott et al., (1995), "The Solution Structure of the F42A Mutant of Human Interleukin 2," *J. Mol. Biol.*, 247:979–994.

Mullins et al., (1998), "Interleukin–12 overcomes paclitaxel–mediated suppression of T–cell proliferation," *Immunopharmacol. Immunotoxicol.*, 20:4:473–492.

Murphy et al., (1986), "Genetic construction, expression, and melanoma–selective cytotoxicity of a diphtheria toxin–related α–melanocyte–stimulating hormone fusion protein," *Proc. Natl. Acad. Sci.*, 83:8258–8262.

Murphy, (1988), "Diphtheria–related peptide hormone gene fusions: A molecular gene approach to chimeric toxin development," *Immunotoxins*, 123–140.

Nedwin et al., (1985), "Human Lymphotoxin and Tumor Necrosis Factor Genes: Structure, Homology and Chromosomal Localization," *Nucleic Acids Research*, 13:17:6361–6373.

Netti et al., (1995), "Time–dependent behavior of interstitial fluid pressure in solid tumors: implications for drug delivery," *Cancer Research*, 55:5451–5458.

Netti et al., (1999), "Enhancement of fluid filtration across tumor vessles: implication for delivery of macromolecules," *Proc. Nat. Acad. Sci*, 96:3137–3142.

Neuberger et al., (1984), "Recombinant Antibodies Possessing Novel Effector Functions," *Nature*, 312:604–608.

O'Reilly et al., (1994), "Angiostatin: A Novel Angiogenesis Inhibitor That Mediates the Suppression of Metastases by a Lewis Lung Carcinoma," *Cell*, 79:315–328.

O'Reilly et al., (1996), "Angiostatin induces and sustains dormancy of human primary tumors in mice," *Nature Medicine*, 2:6:689–692.

O'Reilly et al., (1997), "Endostatin: An Endogeneous Inhibitor of Angiogenesis and Tumor Growth," *Cell*, 88:277–285.

Pastan et al., (1989), "Pseudomonal Exotoxin: Chimeric Toxins," *Journal of Biological Chemistry*, 264:26:15157–15160.

Paul et al., (1988), "Lymphotoxin," *Ann. Rev. Immunol.*, 6:407–438.

Perez et al., (1986), "Specific Targeting of Human Peripheral Blood T Cells by Heteroaggregates Containing Anti–T3 Crosslinked to Anti–Target cell antibodies," *J. Exp. Medicine*, 163:166–178.

Perez et al., (1989), "Isolation and Characterization of a cDNA Encoding the KS1/4 Epithelial Carcinoma Marker," *Journal of Immunology*, 142:10:3662–3667.

Polizzi et al., (1999), "A novel taxane with improved tolerability and therapeutic activity in a panel of human tumor xenografts," *Cancer Research*, 59:1036–1040.

Putzer et al., (1997), "Interleukin 12 and B7–1 Costimulatory Molecule Expressed by an Adenovirus Vector Act Synergistically to Facilitate Tumor Regression," *Proc. Nat'l Acad. Sci.*, 94:20:10889–10894.

Reisfeld et al., (1996), "Recombinant antibody fusion proteins for cancer immunotherapy," *Current Topics in Microbiology and Immunology*, 27–53.

Reisfeld et al., (1997), "Immunocytokines: a new approach to immunotherapy of melanoma," *Melanoma Research*, 7:2:S99–S106.

Riethmuller et al., (1994), "Randomised trial of monoclonal antibody for adjuvant therapy of resected Dukes' C colorectal carcinoma," *The Lancet*, 343:1177–1183.

Roessler et al., (1994), "Cooperative interactions between the interleukin 2 receptor α and β chains alter the interleukin 2–binding affinity of the receptor subunits," *Proc. Natl. Acad. Sci.*, 91:3344–3347.

Rosenberg, (1988), "Immunotherapy of Cancer Using Interleukin 2: current status and future prospects," *Immunology Today*, 9:2:58–62.

Rozwarski et al., (1994), "Structural comparisons among the short–chain helical cytokines," *Structure*, 2:3:159–173.

Santon et al., (1986), "Effects of Epidermal Growth Factor Receptor Concentration on Tumorigenicity of A431 Cells in Nuce Mice," *Cancer Research*, 46:4701–4705.

Sasaki et al., (1998), "Structure, function and tissue forms of the C–terminal globular domain of collagen XVII containing the angiogenesis inhibitor endostatin," *The EMBO Journal*, 17:15:4249–4256.

Sauve et al., (1991), "Localization in human interleukin 2 of the binding site of the α chain (p55) of the interleukin 2 receptor," *Proc. Natl. Acad. Sci.*, 88:4636–4640.

Schnee et al., (1987), "Construction and expression of a recombinant antibody–targeted plasminogen activator," *Proc. Natl. Acad. Sci.*, 84:6904–6908.

Schoenhaut et al., (1992), "Cloning and Expression of Murine IL–12," *Journal of Immunology*, 148:11:3433–3340.

Senter et al., (1988), "Anti–tumor effects of antibody–alkaline phosphatase conjugates in combination with etoposide phosphate," *Proc. Natl. Acad. Sci.*, 85:13:4842–4846.

Shanafelt et al., (2000), "A T–cell–selective interleukin 2 mutein exhibits potent antitumor activity and is well tolerated in vivo," *Nature Biotechnology*, 18:1197–1202.

Sharma et al., (1999), "T cell–derived IL–10 promotes lung cancer growth by suppressing both T cell and APC function," *Journal of Immunology*, 163:5020–5028.

Shen et al., (1986), "Heteroantibody–Mediated Cytotoxicity: Antibody to the high affinity Fc receptor for IgG mediates cytotoxicity by human monocytes that is enhanced by interferon–λ and is not blocked by human IgG," *Journal of Immunology*, 137:11:3378–3382.

Shiff et al., (1995), "Sulindac Sulfide, an Asprin–like Compound, Inhibits Proliferation, Causes Cell Cycle Quiescence, and Induces Apoptosis in HT–29 Colon Adenocarcinoma Cells," *Journal of Clinical Investigation*, 96:491–503.

Shin et al., (1990), "Expression and characterization of an antibody binding specificity joined to insulin–like growth factor 1: Potential applications for cellular targeting," *Proc. Natl. Acad. Sci.*, 87:5322–5326.

Sim et al., (1997), "A Recombinant Human Angiostatin Protein Inhibits Experimental Primary and Metastatic Cancer," *Cancer Research*, 57:1329–1334.

Stevenson et al., (1997), "Conjugation of Human Fcγ in Closed–Hinge or Open–Hinge Configuration to Fab'γ and Analogous Ligands," *Journal of Immunology*, 158:2242–2250.

Sulitzeanu et al., (1993), "Immunosuppressive factors in human cancer," *Adv. Cancer Research*, 60:247–267.

Taniguchi et al., (1983), "Structure and expression of a cloned cDNA for human interleukin–2," *Nature*, 302:305–309.

Tao et al., (1989), "Studies of Aglycosylated Chimeric Mouse IgG: Role of Carbohydrate in the Structure and Effector Functions, Mediated by the Human IgG Constant Region," *Journal of Immunology*, 143:8:2595–2601.

Tao et al., (1993), "Structured Features of Human Immunoglobulin G that Determine Isotype–Differences in Complement Activation," *Journal of Experimental Medicine*, 178:2:661–667.

Teicher et al., (1994), "Potentiation of Cytotoxic Cancer Therapies by TNP–470 Alone and With Other Anti–Angiogenic Agents," *Int. J. Cancer*, 57:920–925.

*The Merck Manual of Diagnosis and Therapy*, 990–993, 1278–1283 (17$^{th}$ ed. 1999).

Till et al., (1988), "An Assay that Predicts the Ability of Monoclonal Antibodies to Form Potent Ricin A Chain–containing Immunotoxins," *Cancer Research*, 48:5:1119–1123.

Till et al., (1988), "HIV–Infected Cells are Killed by rCD4–Ricin A Chain," *Science*, 242:1166–1168.

Trinchieri, (1994), "Interleukin–12: A Cytokine Produced by Antigen–Presenting Cells With Immunoregulatory Functions in the Generation of T–Helper Cells Type 1 and Cytotoxic Lymphocytes," *Blood*, 84:4008–4027.

Vagliani et al., (1996), "Interleukin 12 Potentiates the Curative Effect of a Vaccine Based on Interleukin 2–transduced Tumor Cells," *Cancer Research*, 56:467–470.

Varki et al., (1984), "Antigens Associated with a human lung adenocarcinoma defined by monoclonal antibodies," *Cancer Research*, 44:681–687.

Verhoeyen et al., (1988), "Reshaping Human Antibodies: Grafting an Antilysozyme Activity," *Science*, 239:1534–1536.

Villunger et al., (1997), "Constitutive expression of Fas (Apo–1/CD95) ligand on multiple myeloma cells: a potential mechanism of tumor–induced suppression of immune surveillance," *Blood*, 90:1:12–20.

Watanabe et al., (1997), "Long–term depletion of naive T cells in patients treated for Hodgkin's disease," *Blood*, 90:9:3662–3672.

Williams et al., (1986), "Production of antibody–tagged enzymes by myeloma cells: application to DNA polymerase I Klenow fragment," *Gene*, 43:319–324.

Williams et al., (1987), "Diphtheria toxin receptor binding domain substitution with interleukin–2: genetic construction and properties of a diphtheria toxin–related interleukin–2 fusion protein," *Protein Engineering*, 1:6:493–498.

Wooley et al., (1993), "Influence of a Recombinant Human Soluble Tumor Necrosis Factor Receptor Fc Fusion Protein on Type II Collagen–Induced Arthritis in Mice," *Journal Immunology*, 151: 6602–6607.

Wu et al., (1997), "Suppression of Tumor Growth with Recombinant Murine Angiostatin," *Biochemical and Biophysical Research Communications*, 236:651–654.

Xiang et al., (1997), "Elimination of Established Murine Colon Carcinoma Metastases by Antibody–Interleukin 2 Fusion Protein Therapy," *Cancer Research*, 57:4948–4955.

Xu et al., (1994), "Residue at Position 331 in the IgG1 and IgG4 CH2 Domains Contributes to Their Differential Ability to Bind and Activate Complement," *J. Biol. Chem.*, 269:3469–3474.

Zheng et al., (1995), "Administration of noncytolytic IL–10/Fc in muring models of lipopolysaccharide–induced septic shock and allogenic islet transplantation," *Journal of Immunology*, 154:5590–5600.

Guyre et al., "Increased potency of Fc–receptor–targeted antigens," *Cancer Immunol. Immunother.*, 45: 146–148 (1997).

Lo et al., "High level expression and secretion of Fc–X fusion proteins in mammalian cells," *Protein Engineering*, 11(6): 495–500 (1998).

Becker et al., (1996), "Long–lived and Transferable Tumor Immunity in Mice after Targeted Interleukin–2 Therapy," *J Clin Invest.*, 98(12):2801–2804.

Becker et al., (1996), "T Cell–mediated Eradication of Murine Metastatic Melanoma Induced by Targeted Interleukin–2 Therapy," *J Exp. Med.*, 183(50):2361–6.

Briggs et al., (1974), "Hepatic Clearance of Intact and desialylated Erythropoietin," *American Journal of Physiology*, 227(6):1385–1388.

Chuang et al., (1994), "Alteration of Lymphocyte Microtubule Assembly, Cytotoxicity, and Activation by the Anticancer Drug Taxol," *Cancer Research*, 54:1286–1291.

Cruse et al., (1995), *Illustrated Dictionary of Immunology*, CRC Press, NY, p. 156–157.

Davis et al., (2003), "Immunocytokines: Amplification of Anti–cancer Immunity," *Cancer Immunol. Immunother.*, 52:297–308.

Dolman et al., (1998), "Suppression of Human Prostate Carcinoma Metastases in Severe Combined Immunodeficient Mice by Interleukin 2 Immunocytokine Therapy," *Clin Cancer Res.*, 4(10):2551–7.

Duncan et al., (1988), "The Binding Site for Clq on IgG," *Nature*, 332:738–740.

Egrie et al., (2001), "Development and Characterization of Novel Erythropoiesis Stimulating Protein (NESP)," *Nephrol. Dial. Transplant.*, 16:3–13.

Elliott et al., (1997), "Mapping of the Active Site of Recombinant Human Erythropoietin," *Blood*, 89(2):493–502.

Frost et al., (1997), "A Phase I/IB Trial of Murine Monoclonal Anti GD2 Antibody 14.G2a Plus Interleukin–2 in Children with Refractory Neutroblastoma," *Cancer*, 80:317–33.

Gan et al., (1999), "Specific enzyme–linked Immunosorbent Assays for Quantitation of Antibody–cytokine Fusion Proteins," *Clin. Diagn. Lab. Immunol.*, 6(2):236–42.

Gillies et al., (1991), "Expression of Genetically Engineered Immunoconjugates of Lymphotoxin and a Chimeric Anti–ganglioside GD2 Antibody," *Hybridoma.*, 10(3):347–56.

Gillies et al., (2002), "Bi–functional Cytokine Fusion Proteins for Gene Therapy and Antibody–targeted Treatment of Cancer," *Cancer Immunol. Immunother.*, 51(8):449–60.

Gillies et al., (2002), "Improved Circulating Half–life and eRfficacy of an Antibody–interleukin 2 Immunocytokine Based on Reduced Intracellular Proteolysis," *Clin. Cancer Res.*, 8(1):210–6.

Greene et al., (1975), Neuronal Properties of Hybrid Neuroblastoma X Sympathetic Ganglion Cells, *Proc. Natl. Acad. Sci. USA*, 72(12):4923–4927.

Hank et al., (1996), "Activation of Human Effector Cells by a Tumor Reactive Recombinant Anti–ganglioside GD2 Interleukin–2 Fusion Protein (ch14.18–IL2)," *Clin Cancer Res.*, 2(12):1951–9.

Hank et al., (2003), "Determination of peak serum levels and immune response to the humanized anti–ganglioside antibody–interleukin–2–immunocytokine," *Methods Mol. Med.*, 85:123–31.

Haraguchi, (1994), "Isolation of GD3 Synthase Gene by Expression Cloning of GM3 α–2,8–sialyltrasnferase cDNA using anti–GD2 Monoclonal Antibody," *Proc. Natl. Acad. Sci. USA*, 91(22):10455–9.

Harris, (1995), "Processing of C–terminal Lysine and Arginine Residues of Proteins Isolated from Mammalian Cell Culture," *J. Chromatogr. A.*, 705:129–134.

Hezareh et al, (2001), "Effector Function Activities of a Panel of Mutants of a Broadly Neutralizing Antibody against Human Immunodeficiency Virus Type 1," *J. Virol.*, 75(24):12161–8.

Idusogic et al., (2000), "Mapping of the Clq Binding Site on Rituxan, a Chimeric Antibody with a Human IgG1 Fc," *J. Immunol.*, 164(8):4178–4184.

Imboden et al., (2001), "The Level of MHC Class I Expression on Murine Adenocarcinoma Can Change the Antitumor Effector Mechanism of Immunocytokine Therapy," *Cancer Res.*, 61(4):1500–7.

Kato et al., (1997), "Mechanism for the Nonlinear Pharmacokinetics of Erythropoietin in Rats," *The Journal of Pharmacology and Experimental Therapeutics*, 283:520–527.

Kato et al., (1998), "Pharmacokinetics of Erythopoietin in Genetically Anemic Mice," *Drug Metabolism and Disposition*, 26:126–131.

Kushner et al., (2001), "Phase II Trial of the Anti–GD2 Monoclonal–macrophage–colongy–stimulating Factor for Neuroblastoma," *J. Clin. Oncol.*, 19:4189–94.

Lode et al., (1997), "Targeted interleukin–2 Therapy for Spontaneous Neuroblastoma Metastases to Bone Marrow," *J Natl Cancer Inst.*, 89(21):15868–94.

Lode et al., (2000), "What to do with Targeted IL–2," *Drugs Today*, 36(5):321–36.

Lode et al., (2000), "Melanoma Immunotherapy by Targeted II–2 Depends on CD4(+) T–cell Help Mediated by CD40/CD40L Interaction," *J. Clin. Invest.*, 105(11):1623–30.

Macdougall, (2002), "Optimizing the Use of Erythropoietic Agents—Pharmacokinetic and Pharmacodynamic Considerations," *Nephrol. Dial. Transplant.*, 17:66–70.

Metelitsa et al., (2002), "Antidisialoganglioside/granulocyte Macrophage–colony–stimulating Factor Ffusion Protein Facilitates Neutrophil Antibody–dependent Cellular Cytotoxicity and Depends on FcγRII (CD32) and Mac–1 (CD11b/CD18) for Enhanced Effector Cell Adhesion and Azurophil Granule Exocytosis," *Blood*, 99(11):4166–73.

Mueller et al. (1997), "Humanized Porcine VCAM–specific Monoclonal Antibodies with Chimeric IgG2/G4 Constant Regions Block Human Leukocyte Binding to Porcine Endothelial Cells," *Molecular Immunology*, 34(6):441–452.

Mullins et al. (1997), "Taxol–mediated Changes in Fibrosarcoma–induced Immune Cell Function: Modulation of Antitumor Activities," *Cancer Immunol. Immunother*, 45:20–28.

Naramura et al., "Mechanisms of Cellular Cytotoxicity Mediated by a Recombinant Antibody–IL2 Fusion Protein against Human Melanoma Cells," *Immunology Letters*, 39(1):91–9.

Neal et al. (2003), "NXS2 Murine Neuroblastomas Express Increased Levels of MHC Class I Antigens upon Recurrence Following NK–dependent Immunotherapy," *Cancer Immunol Immunother.*, 53:41–52.

Ngo et al., (1994), "The Protein Folding Problem and Tertiary Structure Prediction," pp. 433–440 and 492–495, Birkhauser Boston.

Niethammer et al., (2002) "An oral DNA Vaccine against Human Carcinoembryonic Antigen (CEA) Prevents Growth and Dissemination of Lewis Lung Carcinoma in CEA Transgenic Mice," *Vaccine*, 20:421–9.

Niethammer et al., (2001) "Targeted Interleukin 2 Therapy Enhances Protective Immunity Induced by an Autologous Oral DNA Vaccine against Murine Melanoma," *Cancer Research*, 61(16):6178–84.

Nimtz et al., (1993) Structures of Sialylated Oligosaccharides of Human Erythropoietin Expressed in Recombinant BHK–21 Cells, *Eur. J. Biochem.*, 213:39–56.

Pancook et al., (1996), "Eradication of Established Hepatic Human Neuroblastoma Metastases in Mice with Severe Combined Immunodeficiency by Antibody–targeted Interleukin–2," *Cancer Immunol. Immunother.*, 42(2):88–92.

Park et al., (2000), "Efficiency of Promoter and Cell line in High–level Expression of Erythropoietin," *Biotechnol. Appl. Biochem.*, 32:167–172.

Reisfeld et al., (1996), "Antibody–interleukin 2 Fusion Proteins: A New Approach to Cancer Therapy," *J Clin Lab Anal.*, 10(3):160–6.

Reisfeld et al., (1996), "Involvement of B Lymphocytes in the Growth Inhibition of Human Pulmonary Melanoma Metastases in Athymic nu/nu Mice by an Antibody–lymphotoxin Fusion Protein," *Cancer Res.*, 56(8):1707–12.

Ruehlmann et al., (2001), "MIG (CIXCL9) Chemokine Gene Therapy Combines with Antibody–cytokine Fusion Protein to Ssuppress Growth and Dissemination of Murine Colon Carcinoma," *Cancer Res.*, 61(23):8498–503.

Sabzevari et al., (1994), "A Recombinant Antibody–interleukin 2 Fusion Protein Suppresses Growth of Hepatic Human Severe Combined Immunodeficiency Mice," *Proc. Natl. Acad. Sci. USA*, 91(20):9626–30.

Seidenfeld et al., (2001), "Epoietin Treatment of Anemia Associated with Cancer Therapy: A Systematic Review and Meta–analysis of controlled Clinical Trials," *Journal of National Cancer Institute*, 93:1204–1214.

Shinkawa et al., (2003), "The Absence of Fucose but Not the Presence of Galactose or Bisecting N–Acetylglucosamine of Human IgG1 Complex–type Oligosaccharides Shows the Critical Role of Enhancing Antibody–dependent Cellular Cytotooxicity," *J. Biol. Chem.*, 278:3466–3473.

Strom et al., (1996), "Therapeutic Approach to Organ Transplantation," *Therapeutic Immunology*, Blackwell Science, Chapter 36, pp. 451–456.

Thommesen et al., (2000), "Lysine 322 in the Human IgG3 CH2 Domain is Crucial for Antibody Dependent Complement Activation," *Mol. Immunol.*, 37(16):995–1004.

Wells, (1990), "Additivity of Mutational Effect in Proteins," *Biochemistry*, 29(37):8509–8517.

Xiang et al., (1998), "Induction of Persistent Tumor–protective Immunity in Mice Cured of Established Colon Carcinoma Metastases," *Cancer Research*, 58(17)3918–3925.

Xiang et al., (1999) "T Cell Memory against Colon Carcinoma is Long–lived in the Absence of Antigen," *J. Immunol.*, 163(7):3676–83.

Xiang et al., (2001), "A Dual Function DNA Vaccine Encoding Carcinoembryonic Antigen and CD40 Ligand Trimer induces T Cell–mediated Protective Immunity Against Colon Cancer in Carcinoembryonic Antigen–Transgenic Mice," *J Immunol.*, 167(8):4560–5.

Xiang et al., (2001), "Protective Immunity Against Human Carcinoembryonic Antigen (CEA) Induced by an Oral DNA Vaccine in CEA–transgenic Mice," *Clin Cancer Res.*, 7(3 Supp):S856–S864.

Yu et al., (1998), "Phase I Trial of a Human–Mouse Chimeric Anti–Disaloganglioside Monoclonal Antibody ch14.18 in Patients with Refractory Neuroblastoma and Osteosarcoma," *J. Clin. Oncol.*, 16(6):2169–80.

Zagozdzon et al. (1999), "Potentiation of Antitumor Effect of IL–12 in Combination with Paclitaxel in Murine Melanoma Model In Vivo," *International Journal of Molecular Medicine*, 4:645–648.

\* cited by examiner

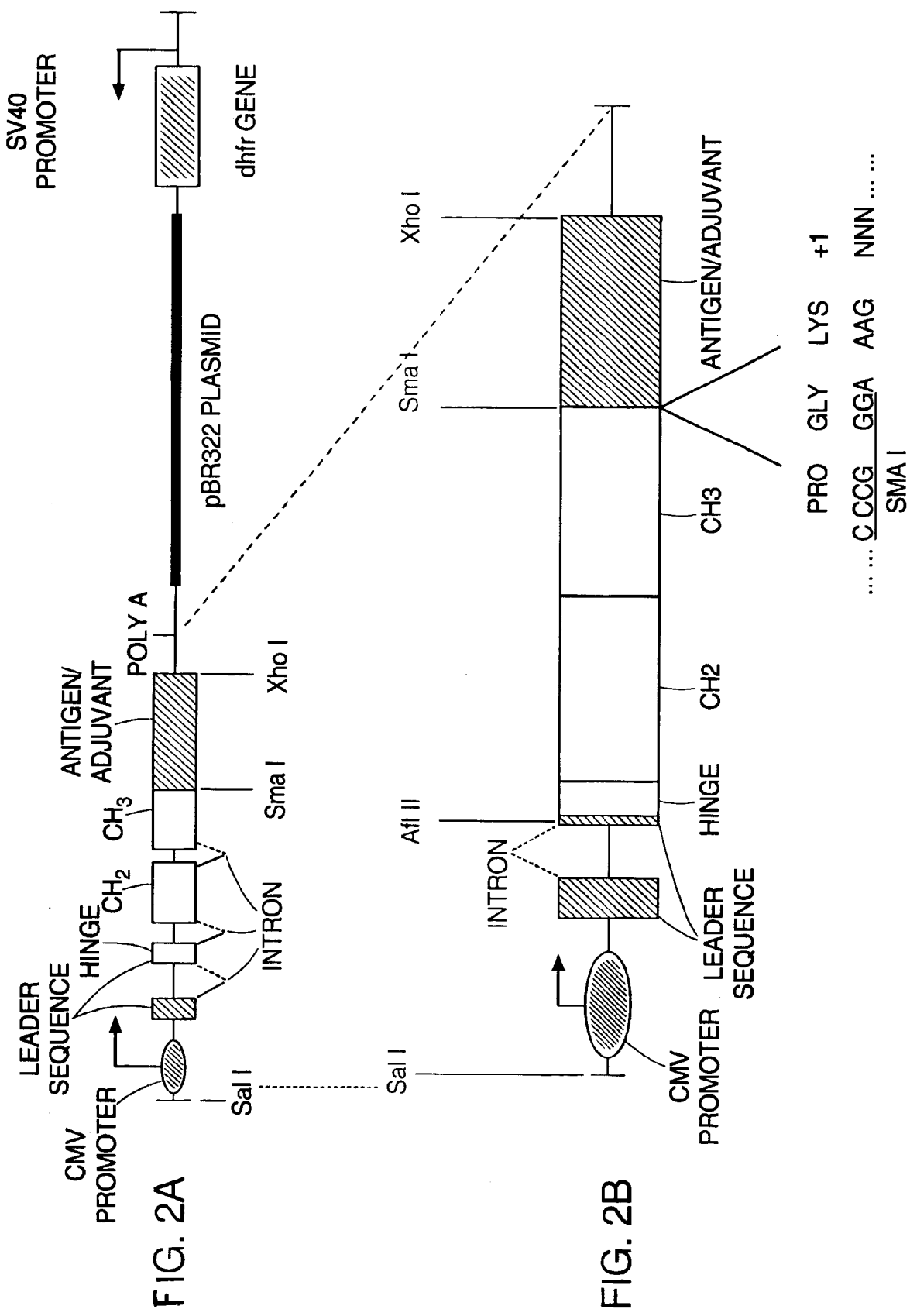

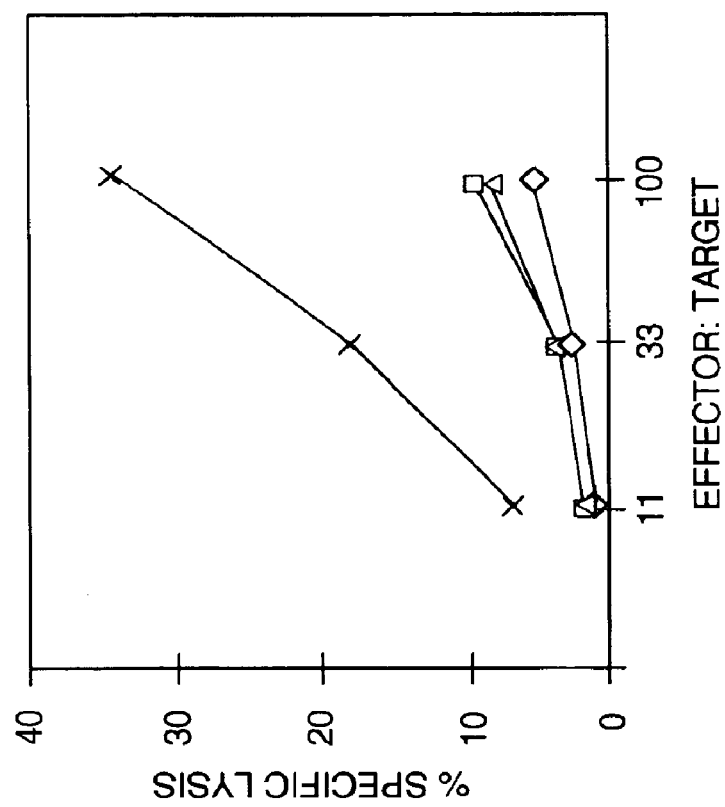
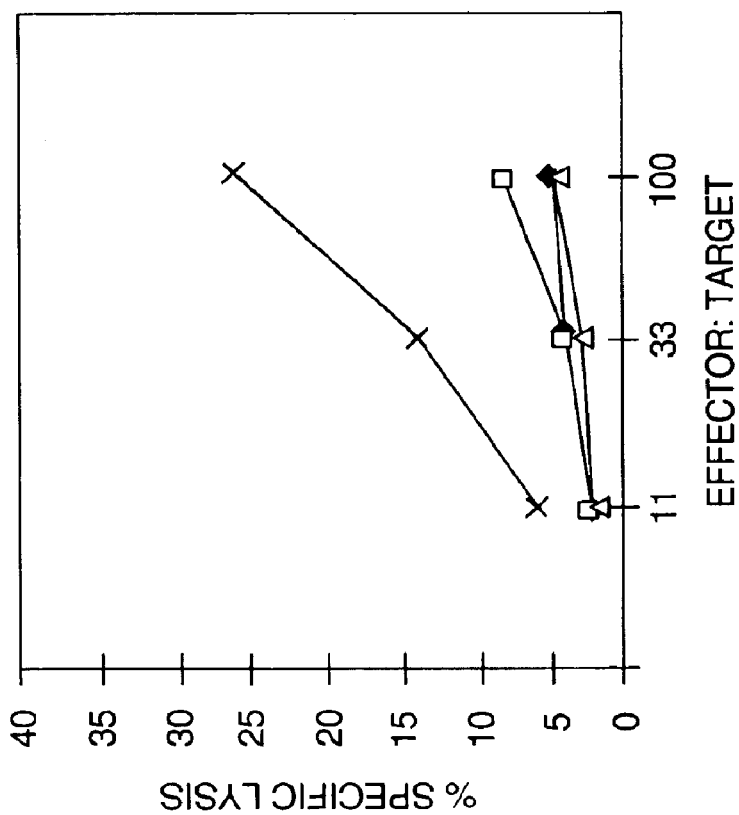
FIG. 12B
FIG. 12A

FC FUSION PROTEINS FOR ENHANCING THE IMMUNOGENICITY OF PROTEIN AND PEPTIDE ANTIGENS

This application claims priority to, and the benefit of U.S.S.N. 60/144,965, filed Jul. 21, 1999, the disclosure of which is incorporated by reference herein.

FIELD OF THE INVENTION

The present invention relates generally to methods and compositions for enhancing the immunogenicity of a preselected protein or peptide antigen in a mammal. More particularly, the invention relates to methods and compositions including nucleic acids encoding, and amino acid sequences defining fusion proteins containing an immunoglobulin heavy chain constant region and a preselected antigen, wherein the preselected antigen in the fusion protein is capable of eliciting a stronger immune response in the mammal relative to the preselected antigen alone.

BACKGROUND OF THE INVENTION

Vaccine development traditionally has focused on the generation of protective antibodies capable of neutralizing infectious agents. To date, the agents used as vaccines typically include inactivated or attenuated microorganisms (for example, bacteria or viruses), their products (for example, toxins), or purified antigens. With the advent of modern molecular biology and gene cloning methodologies, it has been possible to make purer, and apparently more specific vaccines. Furthermore, knowledge of the immune system at a molecular level has permitted the isolation and characterization of immune responses stimulated by infectious agents. Two components of the immune system believed to be central to the successful generation of immune responses include: the pivotal roles of regulatory and cytotoxic T cells; and the manner by which an antigen is presented to these cells by an antigen presenting cell (APC). See, for example, W. E. Paul, ed. (1993) FUNDAMENTALS OF IMMUNOLOGY, Raven Press, Ltd., New York.

Typically, a protein or peptide antigen received from the outside of an APC (exogenous antigen) is degraded within an endocytic vesicle or endosome of the APC, whereupon the resulting peptide fragments form a complex with major histocompatability class (MHC) class II proteins. The resulting complex moves to the cell surface where it is displayed to immune cells neighboring the APC. The peptide fragment fits into a groove defined by the MHC molecule, and the complex may be recognized by a T cell expressing a T cell receptor having binding specificity for the complex. Interaction between a peptide-loaded MHC class II molecule and a helper T cell, referred to in the art as a CD4 T cell, is further stabilized by another interaction between the MHC class II molecule itself and a $CD4^+$ receptor on the surface of the T cell. Thus, exogenous antigen which is processed within APC cells is presented on the cell surface via a MHC class II molecule. The MHC class II complex, when presented to $CD4^+$ T cells, results in the $CD4^+$ helper cell secreting cytokines that stimulate B cells to produce antibodies against the peptide. See, Paul, supra.

Vaccination with exogenous antigen typically results in a CD4 cell-mediated T cell response that generally results in antibody production. Cytotoxic T cells (CTL) typically are not stimulated by such a pathway. Apparently, CTL are stimulated in situations where the antigen originates from inside the APC itself (endogenous antigen), for example, via production of viral proteins in a virally infected cell or cancer-specific proteins in a cancer cell. In fact, in many viral diseases, the generation of CTL is believed to be critical in eliminating virus-infected cells, and thus recovery from infection.

Studies indicate that endogenous and exogenous antigens are processed differently. During synthesis of nascent polypeptides, a portion of the polypeptide is degraded by an intracellular structure called a proteosome. Fragments from this process complex with newly synthesized MHC class I rather than MHC class II molecules, whereupon the resulting antigen containing MHC Class I complexes are transported to the cell surface. Again, T cells with specificity for the specific peptide fragment bind T cells, but in this case, the required co-receptor interaction occurs between MHC class I molecule and a CD8 molecule. Accordingly, endogenous antigen on the surface of the APC is presented to $CD8^+$ T cells. Although there are some types of $CD8^+$ T cells that are not cytotoxic, the $CD8^+$ T cells make up the majority of CTL.

Accordingly, it appears that the design of a vaccine capable of inducing strong CTL responses, requires that the antigenic molecule (generally a protein), either be made inside the cell or delivered into the appropriate cellular compartment so that it can enter the MHC class I processing pathway. One strategy is to incorporate a gene encoding a protein or peptide of interest into a virus, and then use the engineered virus as a vaccine (Lorenz et al. (1999) HUM. GENE THER. 10:623–631). Another strategy is to inject a protein-encoding DNA vector into a cell, and then to administer the cell to the animal or patient where it is expressed from within the cell, and is then presented on the cell surface via MHC class I molecules (Donnelly et al. (1997) ANNU. REV. IMMUNOL. 15:617). A simpler technique of injecting DNA vectors directly into muscle or skin has been shown to induce CTL and/or antibody responses to several antigens (Lai et al. (1988) CRIT. REV. IMMUNOL. 18:449–84 and U.S. Pat. No. 5,589,466). Studies have shown that the antigen is taken up and processed by APC, where it is presented to the immune system (Lai et al., supra).

The delivery of exogenous peptides or proteins to the MHC class I pathway has been partially successful through use of chemical adjuvants such as Freund's adjuvant, and mixtures of squalene and detergents (Hilgers et al. (1999) VACCINE 17:219–228), and more recently through use of small antigen-coated beads which are phagocytosed by macrophages and induce CTL responses via an alternative MHC class I pathway (De Bruijn et al. (1995) EUR. J. IMMUNOL. 25:1274–1285). Furthermore, other methods for enhancing immune responses to an antigen may include the use of chemical adjuvants in combination with recombinant immunostimulatory cytokines, for example, IL-2, IL-12, GM-CSF, and others. For example, one method employs an anti-hapten antibody fused to IL-2 as a way of linking this cytokine to a protein antigen which has been chemically reacted with the hapten (Harvill et al. (1996) J. IMMUNOL. 157:3165).

Another technique exploits antibody "antigenization" whereby a portion of an immunoglobulin variable region is replaced with a peptide antigen. The peptide antigen of the hybrid molecule is presented to an APC once the recombinant antibody binds the APC via interaction with Fc receptors on the surface of the APC (Lanza et al. (1993) PROC. NATL. ACAD. SCI. USA 90:11683–11687). An extension of this approach utilizes splenic injection of plasmid DNA encoding an "antigenized" immunoglobulin heavy chain, after which spleen-derived B cells secrete the recombinant antibody once an immunoglobulin light chain partner is provided.

Immunogenicity of the antigen delivery system, however, is one of the major technical hurdles in modern vaccine development. The goal of vaccination is to elicit a strong immune response. However, because the host immune system has evolved to fight bacteria and viruses, when bacteria or viruses are used as vectors, the messenger typically is destroyed along with the message. Furthermore, strong immune responses to certain viral vectors, for example, vaccinia and adenovirus, limit their utility, and it is contemplated that similar problems can arise during use of bacterial toxins as protein vectors. Likewise, antibody-based "protein vectors" utilizing variable regions that, by their very nature, are not considered as "self" by the immune system are potentially immunogenic. It is contemplated that multiple uses of these carrier molecules can induce anti-idiotypic responses thereby precluding their efficacious use. Accordingly, it is an object of the present invention to provide a vaccine which produces a strong and long lasting immunity against a preselected protein or peptide antigen.

SUMMARY OF THE INVENTION

This invention is based, in part, upon the discovery that it is possible to enhance the immunogenicity of a preselected peptide or protein antigen in a mammal, by fusing the preselected antigen to an immunoglobulin heavy chain constant region. The resulting fusion protein (also referred to herein as an "Fc-antigen fusion protein" or an "antigen fusion protein") or a nucleic acid sequence encoding the fusion protein can then be administered to the mammal in the form of a vaccine to elicit an immune response against the preselected antigen. Furthermore, it has been discovered that the strength and type of immune response elicited against the preselected antigen can be modulated by administering specific adjuvants together with the Fc-antigen fusion protein or the nucleic acid sequence encoding the Fc-antigen fusion protein.

Accordingly, the invention provides a method for enhancing the immunogenicity of a preselected antigen in a mammal. In one aspect, the method comprises administering to the mammal an Fc-antigen fusion protein comprising an immunoglobulin heavy chain constant region linked by a polypeptide bond to the preselected antigen in an amount sufficient to elicit an immune response. In another aspect, the method comprises administering to the mammal a nucleic acid sequence, for example, a deoxyribose nucleic acid (DNA) or ribose nucleic acid (RNA), encoding an Fc-antigen fusion protein comprising an immunoglobulin heavy chain constant region fused to the preselected antigen. The preselected antigen, when part of an Fc-antigen fusion protein (either administered as a fusion protein or nucleic acid which then is expressed in the host to produce the fusion protein), is characterized as being capable of stimulating an immune response in the mammal that is stronger than a comparable amount (for example, by weight or by number of molecules) of preselected antigen alone, i.e., preselected antigen not fused to an immunoglobulin heavy chain constant region.

Furthermore, immune responses elicited against the preselected antigen of the Fc-antigen fusion protein may be enhanced or modulated by administering the Fc-antigen fusion protein together with an adjuvant. Although a variety of adjuvants, for example, chemical adjuvants, such as Freund's complete adjuvant or an oligonucleotide containing an unmethylated CpG sequence, may be useful in the practice of the invention, currently preferred adjuvants to be used with Fc-antigen fusion proteins comprise a second Fc fusion protein (referred to herein as an "Fc-adjuvant fusion protein" or an "adjuvant fusion protein") or a nucleic acid encoding such an Fc fusion protein. Preferred Fc-adjuvant fusion proteins comprise an immunoglobulin heavy chain constant region linked by a polypeptide bond to an adjuvant protein, for example, a cytokine. Preferred cytokines useful in the construction of Fc-adjuvant fusion proteins include, for example, interferon-γ (IFN-γ), interleukin-2 (IL-2), interleukin-4 (IL-4), interleukin-12 (IL-12), IL-18, tumor necrosis factor (TNF), granulocyte macrophage colony stimulating factor (GMCSF). Another class of Fc-adjuvant fusion protein comprises an immunoglobulin heavy chain region fused to an adjuvant moiety corresponding to an extracellular domain of a protein that usually is partically or exclusively membrane-bound. For example, CD40 ligand is fused to an Fc moiety to be used as an enhanced adjuvant protein.

Co-administration of the Fc-antigen and Fc-adjuvant fusion proteins, either simultaneously or one after the other (for example, Fc-antigen followed by Fc-adjuvant or Fc-adjuvant followed by Fc-antigen), can be used to modulate the type of immune response that is stimulated against the preselected antigen. Two classes of immune response, termed Th1 and Th2, are initiated in response to different stimuli and involve different cytokines. Th1 mediated immune responses typically are cellular in nature, whereas Th2 mediated immune responses typically are humoral in nature. Accordingly, a Th1 response can be useful in attacking altered cells, such as cancer cells or virus-infected cells, whereas a Th2 response can be useful in attacking extracellular agents such as parasites. Often it is useful to administer cytokines, fused to immunoglobulin heavy chain constant regions, to stimulate either a general immune response, or to initiate or modulate specific Th1 or Th2 responses.

For example, an Fc-adjuvant fusion protein comprising an immunoglobulin heavy chain constant region linked by a peptide bond to GMCSF is a potent general stimulator of immune responses, including both Th1 and Th2 responses. An Fc-adjuvant fusion protein comprising IL-12 or IFN-γ may be co-administered to stimulate a primarily cellular or Th1 mediated immune response. Alternatively, an Fc-adjuvant fusion protein comprising IL-4 may be administered to stimulate a primarily humoral or Th2 mediated immune response.

Furthermore, the choice of a particular cytokine present in an Fc-adjuvant fusion protein can influence the class of antibody produced against the preselected antigen of the Fc-antigen fusion protein. For example, an IL-12 containing Fc-adjuvant fusion protein can stimulate helper T cells, and the production of the IgG2a class of antibody. Alternatively, an IL-4 containing adjuvant fusion protein can stimulate the production of the IgE class of antibody.

As discussed previously, in a preferred embodiment, the method comprises administering the Fc-antigen fusion protein or the nucleic acid encoding the Fc-antigen fusion protein in combination with an Fc-adjuvant fusion protein. By using two fusion proteins, each containing an immunoglobulin heavy chain constant region, it is possible to co-localize both the preselected antigen and the adjuvant protein (for example, a cytokine) at the same or similar cell types in the mammal. For example, macrophages, B cells, granulocytes and dendritic cells express Fc receptors on their cell surface. Accordingly, by co-administering Fc-antigen and Fc-adjuvant fusion proteins capable of binding Fc receptors, it is possible to co-localize the antigen of the antigen fusion protein and the adjuvant of the adjuvant fusion protein at the same cell types. The adjuvant can then stimulate, enhance or otherwise modulate the immune response in the vicinity of the preselected antigen.

In this preferred embodiment, the invention uses two distinct forms of localization or concentration. First, the invention uses a common moiety that is fused to both the antigen and adjuvant, that is concentrated to certain regions of the body. In this way, the effective local concentration of the antigen in the neighborhood of the adjuvant is increased. Second, the invention targets the antigen to the antigen processing and presentation machinery of the immune system. The first concentration step may be carried out by fusing the antigen and adjuvant proteins to a moiety that results in concentration in some part of the body that is accessible to the immune system. The second targeting step may be carried out by fusing the antigen protein to any moiety that enhances the delivery to, or processing by, the antigen presentation system.

Accordingly, the invention achieves these concentration effects by two alternative methods. One method is to construct and administer two different fusion proteins, an antigen-localizing protein fusion and an adjuvant-localizing protein fusion. A second method is to construct and administer a fusion containing the antigen, the adjuvant, and the localizing protein. An Fc moiety is an example of a localizing protein.

An important feature of the immunoglobulin heavy chain constant region is that, unlike the preselected antigen in the Fc-antigen fusion protein, it preferably is non-immunogenic or is only weakly immunogenic in the intended recipient. In other words, in the Fc-antigen fusion protein the preselected antigen is designed to be more immunogenic in the recipient than the immunoglobulin heavy chain constant region. Similarly, it is contemplated that the Fc-adjuvant fusion protein should also be non- or weakly immunogenic in the intended recipient. Immunogenicity of an immunoglobulin heavy chain constant region can be reduced, and, in certain cases, eliminated by using immunoglobulin constant region sequences derived from, or similar to those present in the same species as the intended recipient. For example, immunoglobulin heavy chain constant regions, preferably of human origin, are used to generate fusion proteins to be administered to humans. Similarly, when the intended recipient is a human, the adjuvant protein in the Fc-adjuvant fusion protein also preferably is of human origin. By choice of suitable amino acid sequences defining immunoglobulin heavy chain constant regions and adjuvant proteins, it is possible to optimize an immune response directly primarily against the preselected antigen.

In a preferred embodiment, the immunoglobulin heavy chain constant region of the Fc-antigen fusion protein comprises an immunoglobulin hinge region, and optionally an immunoglobulin constant region domain selected from the group consisting of a CH2 domain, a CH3 domain and a CH4 domain, or a combination thereof. The immunoglobulin heavy chain constant region, however, preferably lacks at least a CH1 domain. Furthermore, the Fc fusion proteins of the invention, preferably lack an immunoglobulin heavy chain variable region domain ($V_H$). When the fusion protein is to be administered to a human, the immunoglobulin heavy chain constant region preferably comprises a hinge region, and a CH2 domain or a CH3 domain, and most preferably comprises a hinge region and both a CH2 domain and a CH3 domain. It is contemplated that immunoglobulin heavy chain constant regions useful in the practice of the invention may be derived from immunoglobulins belonging to any of the five immunoglobulin classes referred to in the art as IgA (Igα), IgD (Igδ), IgE (Igε), IgG (Igγ), and IgM (Igμ). However, immunoglobulin heavy chain constant regions from the IgG class are preferred.

It is contemplated that any preselected antigen of interest may be included in the Fc-antigen fusion protein of the invention. In a preferred embodiment, the preselected antigen is selected from the group consisting of a prostate-specific membrane antigen, an ectodomain of a cytokine receptor, a viral protein, and a cancer or tumor-specific antigen.

Fc-antigen fusion proteins having a variety of configurations may be useful in the practice of the invention. For example, the N-terminus of the preselected antigen may be linked by a polypeptide bond to the C-terminus of the immunoglobulin heavy chain constant region. Alternatively, the C-terminus of the preselected antigen may be linked by a polypeptide bond to the N-terminus of the immunoglobulin heavy chain constant region. Furthermore, it is contemplated that the Fc-antigen fusion proteins may comprise a plurality of one or more preselected antigens, one or more of which may be linked directly or via a polypeptide linker to each other or to the immunoglobulin heavy chain constant region. Furthermore, two or more Fc-antigen fusion proteins may be associated together either non-covalently or covalently, for example, through one or more disulfide bonds, to produce dimeric or multimeric compositions. It is contemplated that the Fc-antigen fusion proteins in the dimeric constructs may be the same or different to one another. For example, although both Fc-antigen fusion proteins may comprise the same immunoglobulin heavy chain constant region, the preselected antigens may differ. It is contemplated that similar configurations can be employed with the Fc-adjuvant fusion proteins also.

Furthermore, a variety of nucleic acid sequences encoding Fc fusion proteins may be useful in the practice of the invention. For example, the nucleic acid sequences may encode in a 5' to 3' direction, either the immunoglobulin heavy chain constant region and the preselected antigen, or the preselected antigen and the immunoglobulin heavy chain constant region. Furthermore, the nucleic acid sequences optionally may also include a "leader" or "signal" sequence based upon, for example, an immunoglobulin light chain sequence fused directly to a hinge region of the immunoglobulin heavy chain constant region. In a preferred embodiment, when the Fc region is based upon IgG sequences, the Fc region encodes in a 5' to 3' direction, at least an immunoglobulin hinge region (i.e., a hinge region containing at least one cysteine amino acid capable of forming a disulfide bond with a second immunoglobulin hinge region sequence), an immunoglobulin CH2 domain and a CH3 domain. Furthermore, a nucleic acid sequence encoding the Fc-antigen fusion proteins may also be integrated within a replicable expression vector that may either express the Fc fusion protein in, for example, a bacterial host, the intended recipient, or both.

It is contemplated that injection of nucleic acid sequences encoding the Fc-antigen fusion protein, either alone or in combination with nucleic acid sequences encoding the Fc-adjuvant fusion protein, may result in the generation of a cellular immune response, a humoral immune response, or both. Combinations of nucleic acid- and protein-based immunizations (e.g., administration of an Fc-antigen fusion protein before, during or after administration of a nucleic acid encoding the Fc antigen fusion protein) may act synergistically with one another to elicit stronger immune responses against the preselected antigen relative to immunization with either the nucleic acid or protein alone.

The foregoing and other objects, features and advantages of the present invention will be made more apparent from the following detailed description, drawings, and claims that follow.

BRIEF DESCRIPTION OF THE DRAWINGS

The foregoing and other objects, features, and advantages of the present invention as well as the invention itself, may be more fully understood from the following description of preferred embodiments, when read together with the accompanying drawings, in which:

FIG. 1A represents an Fc-antigen or Fc-adjuvant fusion protein where the immunoglobulin heavy chain constant region 1 is attached to the N-terminal end of the antigen or adjuvant 2. FIG. 1B represents an Fc-antigen or Fc-adjuvant fusion protein where the immunoglobulin heavy chain constant region 1 is attached to the C-terminal end of the antigen or adjuvant 2. FIGS. 1C and 1D represent a dimeric protein wherein either or both of polypeptide chains comprise an Fc-antigen or an Fc-adjuvant fusion protein. In FIG. 1C, in at least one polypeptide chain, the immunoglobulin heavy chain constant region 1 is attached to the N-terminal end of the antigen or adjuvant 2, and in FIG. 1D, the immunoglobulin heavy chain constant region 1 is attached to the C-terminal end of the antigen or adjuvant 2. FIG. 1E represents a dimeric protein wherein either or both of the polypeptide chains comprise an Fc-antigen-antigen, Fc-adjuvant-adjuvant, Fc-adjuvant-antigen or Fc-antigen-adjuvant fusion protein. FIG. 1F represents a dimeric fusion protein, wherein either or both of the polypeptide chains comprise an antigen-Fc-adjuvant or an adjuvant-Fc-antigen fusion protein. FIG. 1G represents a dimeric fusion protein, wherein either or both of the polypeptide chains comprise an antigen-adjuvant-Fc or an adjuvant-antigen-Fc fusion protein.

FIGS. 2A–2B are schematic representations of DNA sequences useful in the practice of the invention. FIG. 2A represents a human Fc fusion protein expression vector. FIG. 2B represents a gene fusion for expression of a mouse IgG2a Fc fusion protein.

In FIG. 3A, mice were immunized with Fc-IL-4R and Fc-IL-2 in Freund's complete adjuvant (CFA). In FIG. 3B, mice were immunized with Fc-IL4R in phosphate buffered saline (PBS). In FIG. 3C, mice were immunized with Fc-IL-4R in CFA. In FIG. 3D, mice were immunized with Fc-IL-4R and Fc-IL-2 in PBS. In FIG. 3E, mice were immunized with Fc-IL-4R and Fc-GMCSF in CFA. In FIG. 3F, mice were immunized with Fc-IL-4R and Fc-GMCSF in PBS. In FIGS. 3A–3F, the squares, diamonds and triangles represent data derived from three separate mice. The levels of antibodies to an antigen were measured by ELISA; the Y-axis indicates the optical density of the ELISA readout.

In FIG. 4A, mice were immunized with 50 μg of Fc-PSMA fusion protein alone. In FIG. 4B, mice were immunized with 50 μg of Fc-PSMA and 0.05 μg of Fc-GMCSF as an adjuvant. In FIG. 4C, mice were immunized with 50 μg of Fc-PSMA and 0.5 μg of Fc-GMCSF as an adjuvant. In FIG. 4D, mice were immunized with 50 μg of Fc-PSMA and 5 μg of Fc-GMCSF. In FIGS. 4A–4D, the squares, diamonds and triangles represent data derived from three separate mice.

FIGS. 5A–5F are graphs comparing the specific antibody responses to the PSMA antigen administered either as a native protein (5A–5C) or as a mouse Fc-PSMA fusion protein (5D–5F). In FIG. 5A, mice were immunized with 50 μg of PSMA as an antigen. In FIG. 5B, mice were immunized with 50 μg of PSMA as an antigen and 0.2 μg of GMCSF as an adjuvant. In FIG. 5C, mice were immunized with 50 μg PSMA as an antigen and 0.5 μg of Fc-GMCSF as an adjuvant. In FIG. 5D, mice were immunized with a50 μg of Fc-PSMA as an antigen. In FIG. 5E, mice were immunized with 50 μg of Fc-PSMA as an antigen and 0.2 μg GMCSF as an adjuvant. In FIG. 5F, mice were immunized with 50 μg of Fc-PSMA as an antigen and 0.5 μg of Fc-GMCSF as an adjuvant. In FIGS. 5A–5F, the squares, diamonds, and triangles represent data derived from three separate mice. The levels of antibodies to an antigen were measured by ELISA; the Y-axis indicates the optical density of the ELISA readout.

FIGS. 7A and 7B represent antibody titers measured 7 and 14 days after boost, respectively. Boost was given three weeks after the primary immunization. In both Figures, the open diamonds represent mice immunized subcutaneouly with 10 μg of Fc-EpCAM alone, and the solid triangles represent mice immunized subcutaneouly with 10 μg of Fc-EpCAM and 1 μg of Fc-GMCSF as an adjuvant. The levels of antibodies to an antigen were measured by ELISA; the Y-axis indicates the optical density of the ELISA readout.

FIGS. 8A and 8B represent antibody titers measured 14 days and 21 days (i.e., 7 days after boost) after immunization, respectively. In both Figures, the open diamonds represent average titers of three mice immunized with 25 μg of EpCAM-Fc fusion proteins, and the solid triangles represent mice immunized with 25 μg of EpCAM-Fc and 2.5 μg of Fc-GMCSF as an adjuvant. The levels of antibodies to an antigen were measured by ELISA; the Y-axis indicates the optical density of the ELISA readout.

FIGS. 10A–10D represent antibody titers recorded 14 days, 27 days, 55 days and 69 days post initial injection, respectively. Throughout the Figures, the open diamonds represent titers for individual mice injected with the Fc-EpCAM encoding plasmid in PBS, and the solid triangles represent titers for individual mice injected with Fc-EpCAM encoding plasmid in sucrose. The levels of antibodies to an antigen were measured by ELISA; the Y-axis indicates the optical density of the ELISA readout.

FIG. 11B shows an expanded view of the data in the lower portion of FIG. 11A. Throughout the Figures, the solid diamonds represent splenocytes harvested from mice immunized with 100 µg of plasmid DNA encoding the CMV-Fc-EpCAM fusion protein, the open circles represent splenocytes harvested from mice immunized with 100 µg of plasmid DNA encoding the CMV-EpCAM-Fc fusion protein, and the crosses represent splenocytes harvested from mice immunized with 10 µg of Fc-EpCAM protein. The spleens were removed from the mice on day 70 after the first injection of plasmid DNA or protein and two booster injections at 3 week intervals.

FIGS. 12A–B are graphs showing a cytotoxic T lymphocyte (CTL) killing assay using splenocytes from plasmid DNA or Fc-EpCAM protein immunized mice. FIG. 12A shows activity of splenocytes against mouse CT26 tumor cells expressing the human EpCAM protein. FIG. 12B shows activity of splenocytes against the parental mouse CT26 tumor cells. For both figures, the open diamonds represent splenocytes immunized with DNA carrying a (CMV-promoter)-EpCAM construct, open squares represent splenocytes from mice immunized with DNA carrying a (CMV-promoter)-Fc-EpCAM fusion construct, open triangles represent splenocytes from mice immunized with DNA carrying a (CMV-promoter)-EpCAM-Fc fusion construct, and crosses represent splenocytes from mice immunized with Fc-EpCAM fusion protein. The CTL assay used splenocytes from the immunized mice cultured for five days with 10 U/ml of IL-2. Labeled target cells were mixed with the indicated effectors and incubated for four hours. The release of radioactivity was used to calculate the percentage of specific lysis.

FIGS. 14A and 14B represent antibody titers achieved 7 and 33 days after a second boost, respectively. Throughout the Figures, open diamonds represent antibody titers in mice immunized by intradermal injection with 25 µg Fc-gp41pep626 antigen alone, open squares represent titers in mice immunized by intradermal injection with 25 µg Fc-gp41pep626 antigen in combination with 2.5 µg Fc-GMCSF adjuvant, and solid triangles represent antibody titers in mice immunized by intradermal injection with 25 µg Fc-gp41pep626 antigen in combination with 2.5 µg Fc-IL2 adjuvant. The levels of antibodies to an antigen were measured by ELISA; the Y-axis indicates the optical density of the ELISA readout.

DETAILED DESCRIPTION OF THE INVENTION

Figure 1A:
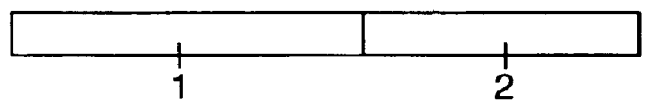
FIGS. 1A–1G are schematic illustrations of exemplary Fc-fusion proteins useful in the practice of the invention.

The present invention is directed to the efficient delivery of protein or peptide antigens in vivo for inducing humoral (i.e., antibody based) or Th2 cell mediated immune responses, cellular or Th1 cell mediated immune responses, and in some cases, both types of immune responses in a mammal. It has now been discovered that it possible to enhance the immunogenicity of a preselected protein or peptide antigen in a mammal by fusing the preselected antigen to an immunoglobulin heavy chain constant region to produce an Fc-antigen fusion protein. The resulting Fc-antigen fusion protein, or nucleic acid sequences encoding the Fc-antigen fusion proteins can then be administered to the mammal, for example, a human, in the form of a vaccine to elicit an immune response against the preselected antigen.

The Fc-antigen fusion protein selectively targets the antigen to antigen presenting cells (APCs). Without wishing to be bound by theory, it is believed that the binding of the Fc-antigen fusion protein to the APCs is mediated through Fc receptors expressed on numerous immune cell types, including, for example: dendritic cells; macrophages; B-cells; and granulocytes. The Fc-antigen fusion protein when administered to the mammal, binds Fc receptors, after which the Fc-antigen fusion protein is endocytosed by the APCs. The endocytosed fusion protein, including the preselected antigen, then is believed to be degraded into small peptides which are then presented on the cell surface. The presented peptides then mediate a humoral and/or cellular immune response. The particular type of immune response stimulated can be modulated by co-administering the Fc-antigen fusion protein with an adjuvant, for example, an adjuvant fusion protein.

In one mode of administration, an Fc-antigen fusion protein is administered to the recipient. In another mode of administration, a nucleic acid sequence encoding the Fc-antigen fusion protein is administered to the recipient. The preselected antigen, either in the administered Fc-antigen protein or as expressed from the administered nucleic acid, is more immunogenic than the antigen alone, i.e., antigen not fused by a polypeptide bond to an immunoglobulin heavy chain constant region. Furthermore, in certain circumstances, sequential administration of fusion protein followed by administration of nucleic acid encoding the same fusion protein, or alternatively, administration of nucleic acid encoding the fusion protein followed by administration of the same fusion protein can be used to maximize the immunogenicity of the preselected antigen. It is understood that an optimal immune response is elicited when both components of the Fc-antigen fusion proteins are active. In other words, the preselected antigen in the Fc-antigen fusion protein is capable of eliciting an immune response and the immunoglobulin heavy chain constant region is capable of binding an Fc receptor on the surface of APCs.

Furthermore, as discussed, the strength and type of immune response elicited against the preselected antigen can be modulated by co-administering specific adjuvants with the Fc-antigen fusion protein and/or the nucleic acid encoding the Fc-antigen fusion protein. Although chemical adjuvants, e.g., alum or Freund's complete or incomplete adjuvants, may under certain circumstances, for example, in veterinary applications, be useful in the practice of the invention, their side effects, for example, tissue scarring, can make them unacceptable for human use. Accordingly, preferred adjuvants comprise a second Fc fusion protein, wherein an immunoglobulin heavy chain constant region is fused to an adjuvant protein to produce an Fc-adjuvant fusion protein. As with the Fc-antigen fusion proteins, it is understood that an optimal immune response is elicited when both components of an Fc-adjuvant fusion protein are active. In other words, the adjuvant in the Fc-adjuvant fusion protein is capable of modulating an immune response and the immunoglobulin heavy chain constant region is capable of binding an Fc receptor on the surface of APCs.

In a preferred embodiment of the invention, both the antigen and the adjuvant are administered as Fc fusion proteins or nucleic acids encoding such fusion proteins. In other words, the antigen is administered as an Fc-antigen fusion protein and the adjuvant is administered as an Fc-adjuvant fusion protein. Certain preferred embodiments of Fc fusion proteins useful in the practice of the invention are illustrated in FIGS. 1A–1G.

Figure 1B:

FIG. 1A illustrates an exemplary Fc fusion protein in which the C terminus of the immunoglobulin heavy chain constant region 1 is connected, either directly or by means of a polypeptide linker, to the N-terminus of the preselected antigen or adjuvant 2. As used herein, the term "polypeptide linker" is understood to mean a sequence of one or more amino acid residues which couple two proteins together. The polypeptide linker often is a series of amino acids of about 10–15 residues in length, comprising, for example, repeating glycine and/or serine residues. FIG. 1B illustrates an exemplary Fc fusion protein in which the C terminus of the preselected antigen or adjuvant 2 is connected, either directly or by means of a polypeptide linker, to the N-terminus of the immunoglobulin heavy chain constant region 1.

Figure 1C:
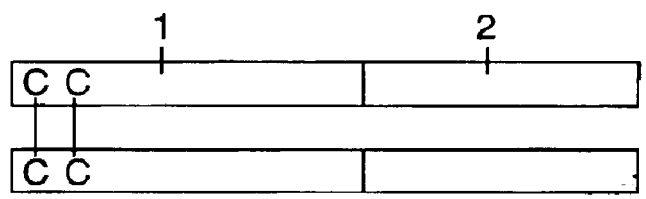
Figure 1D:
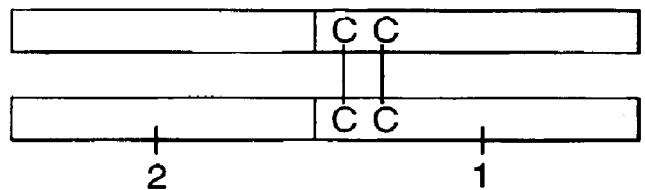

FIG. 1C depicts a dimeric construct containing two Fc fusion proteins linked covalently by means of two disulfide bonds. The dimeric construct comprises two Fc fusion proteins in which the C-terminus of each immunoglobulin heavy chain constant region 1 is linked to the N-terminus of a preselected antigen of adjuvant 2. Similarly, FIG. 1D depicts a dimeric construct containing two Fc fusion proteins linked covalently by means of two disulfide bonds. The dimeric construct comprises two Fc fusion proteins in which the C-terminus of each preselected antigen or adjuvant 2 is linked to the N-terminus of the immunoglobulin heavy chain constant region 1.

Figure 1E:
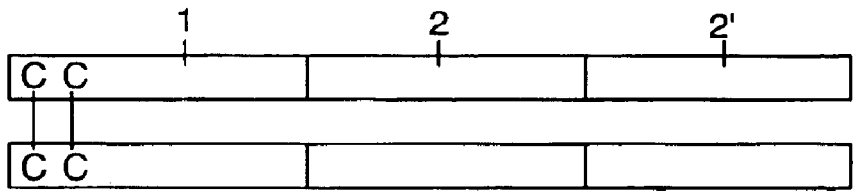

FIG. 1E depicts a dimeric construct containing two Fc fusion proteins linked by means of two disulfide bonds. The dimeric construct comprises two Fc fusion proteins in which the C-terminus of each immunoglobulin heavy chain constant region 1 is linked, either directly or via a polypeptide linker, to the N-terminus of a preselected antigen or adjuvant 2, the C-terminus of which is attached, either directly or via a polypeptide linker, to a second antigen or adjuvant 2'.

Figure 1F:
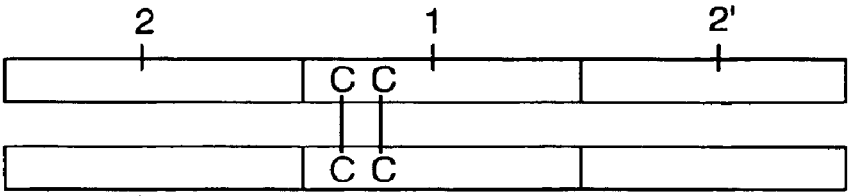

FIG. 1F depicts a dimeric construct containing two Fc fusion proteins also linked by means of two disulfide bonds. The dimeric construct comprises two Fc fusion proteins in which the C-terminus of the antigen or adjuvant 2 is linked, either directly or via a polypeptide linker, to the N-terminus of the immunoglobulin heavy chain constant region 1, whose C-terminus is linked, either directly or via a polypeptide linker, to the N-terminus of a different adjuvant or antigen 2'. For example, such fusion proteins may include, in an N- to C-terminal direction, preselected antigen-immunoglobulin heavy chain constant region-adjuvant.

Figure 1G:
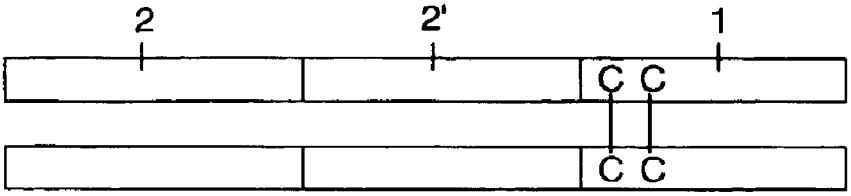
Figure 3A:
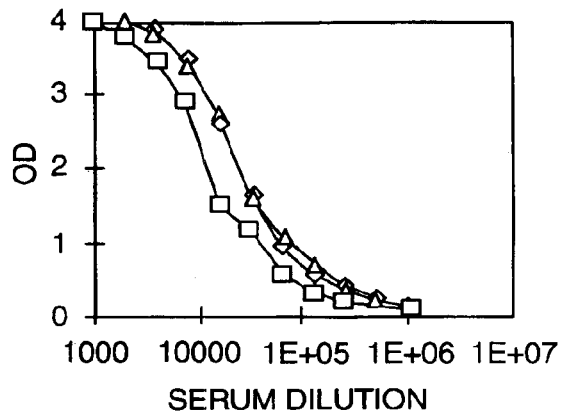
FIGS. 3A–3F are graphs showing the effect of chemical and Fc-cytokine adjuvants on antibody production in mice immunized with the Fc-antigen fusion protein, mouse Fc-human IL-4 receptor ectodomain (Fc-IL-4R) fusion protein.
Figure 3B:
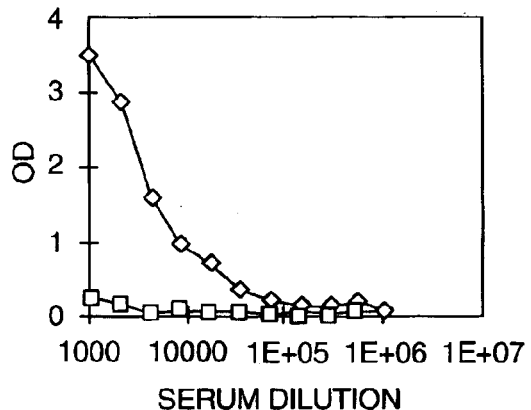
Figure 3C:
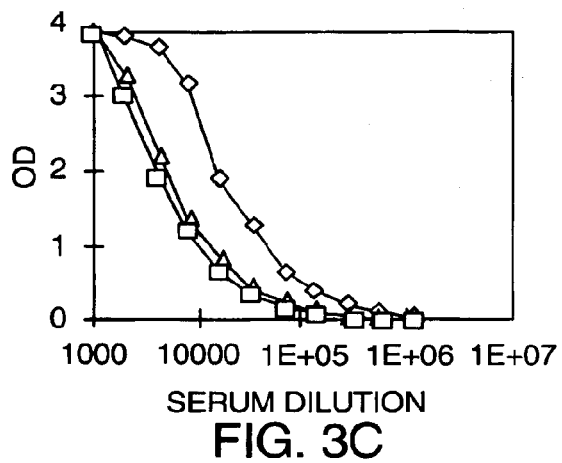
Figure 3D:
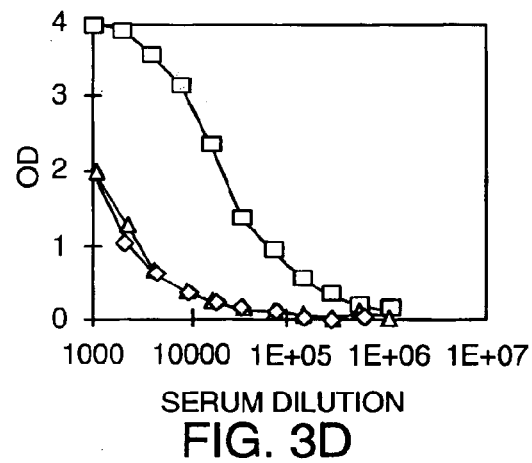
Figure 3E:
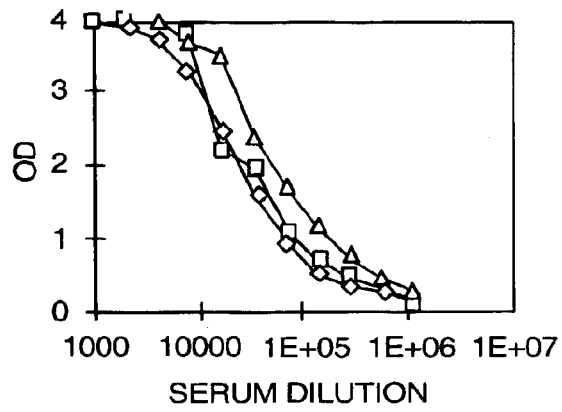
Figure 3F:
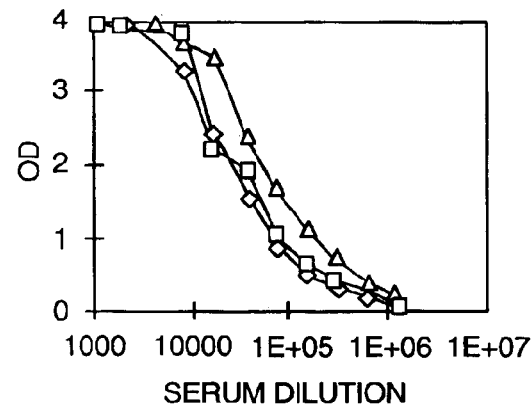

FIG. 1G depicts a dimeric construct containing two Fc fusion proteins also linked by means of two disulfide bonds. The dimeric construct comprises two Fc fusion proteins in which the C-terminus of the antigen or adjuvant 2 is linked, either directly or via a polypeptide linker, to the N-terminus of a different adjuvant or antigen 2', whose C-terminus is linked, either directly or via a polypeptide linker to the N-terminus of the immunoglobulin heavy chain constant region 1. For example, such fusion proteins may include, in an N- to C-terminal direction, preselected antigen-adjuvant-immunoglobulin heavy chain constant region.

In the practice of the invention, it is generally preferred to place the Fc moiety in an N-terminal position relative to the adjuvant moiety. If the adjuvant moiety is placed N-terminal to the Fc moiety, then the adjuvant-Fc fusion may bind to an adjuvant receptor on an immune cell and the Fc moiety will be in the same orientation that is adopted when an antibody binds to a cell surface. ADCC or complement fixation may result. However, when the Fc moiety is placed N-terminal to the adjuvant moiety, ADCC and complement fixation do not appear to result.

The constructs depicted in FIGS. 1C–1G are illustrated as dimers cross-linked by a pair of disulfide bonds between cysteines on adjacent hinge regions. In the drawings the disulfide bridges are depicted as linking together the portions of two immunoglobulin heavy chain constant regions via the hinge region characteristic of native forms of these molecules. While constructs including immunoglobulin hinge regions are preferred, the invention contemplates that crosslinking at other positions may be chosen as desired. Furthermore, in some cases, two or more monomers may associate non-covalently to produce dimers or multimers useful in the practice of the invention.

As used herein, the term "immunoglobulin heavy chain constant region" is used interchangeably with the term "Fc region" and is understood to mean the carboxyl-terminal portion of an immunoglobulin heavy chain constant region, or an analog or portion thereof capable of binding an Fc receptor. As is known, each immunoglobulin heavy chain constant region comprises four or five domains. The domains are named sequentially as follows: CH1-hinge-CH2-CH3(-CH4). CH4 is present in IgM, which has no hinge region. The immunoglobulin heavy chain constant region useful in the practice of the invention preferably comprises an immunoglobulin hinge region, and preferably also includes a CH3 domain. The immunoglobulin heavy chain constant region most preferably comprises an immunoglobulin hinge region, a CH2 domain and a CH3 domain. As used herein, the term immunoglobulin "hinge region" is understood to mean an entire immunoglobulin hinge region or at least a portion of the immunoglobulin hinge region sufficient to form one or more disulfide bonds with a second immunoglobulin hinge region.

It is contemplated that suitable immunoglobulin heavy chain constant regions may be derived from antibodies belonging to each of the immunoglobulin classes referred to as IgA, IgD, IgE, IgG, and IgM, however, immunoglobulin heavy chain constant regions from the IgG class are preferred. Furthermore, it is contemplated that immunoglobulin heavy chain constant regions may be derived from any of the IgG antibody subclasses referred to in the art as IgG1, IgG2, IgG3, and IgG4.

Immunoglobulin heavy chain constant region domains have cross-homology among the immunoglobulin classes. For example, the CH2 domain of IgG is homologous to the CH2 domain of IgA and IgD, and to the CH3 domain of IgM and IgE. Preferred immunoglobulin heavy chain constant regions include protein domains corresponding to a CH2 region and a CH3 region of IgG, or functional portions or derivatives thereof. The immunoglobulin heavy chain constant regions, however, preferably lack at least the CH1 domain. Furthermore, the Fc-antigen or Fc-adjuvant fusion proteins optionally lack an immunoglobulin variable region. In a more preferred embodiment, the immunoglobulin heavy chain constant region comprises, in an N to C terminal direction, an immunoglobulin hinge region, a CH2 domain and a CH3 domain all of which are based on sequences from an IgG molecule. The choice of appropriate immunoglobulin heavy chain constant regions is discussed in detail in U.S. Pat. No. 5,541,087, and U.S. Pat. No. 5,726,044. The choice of particular immunoglobulin heavy chain constant region sequences from certain immunoglobulin classes and subclasses to achieve a particular result is considered to be within the level of skill in the art.

It may be useful, in some circumstances, to modify the immunoglobulin heavy chain constant region, for example, by mutation, deletion or other changes mediated by genetic engineering or other approaches, so that certain activities, such as complement fixation or stimulation of antibody-dependent cell-mediated cytotoxicity (ADCC) are reduced or eliminated. However, it is considered necessary that the immunoglobulin heavy chain constant region's ability to bind an Fc receptor is maintained.

In the practice of this invention, the immunoglobulin heavy chain constant region component of the Fc-antigen or Fc-adjuvant fusion proteins preferably is non-immunogenic or is weakly immunogenic in the intended recipient. The Fc region is considered non- or weakly immunogenic if the immunoglobulin heavy chain constant region fails to generate a detectable antibody response directed against the immunoglobulin heavy chain constant region. Accordingly, the immunoglobulin heavy chain constant region should be derived from immunoglobulins present, or based on amino acid sequences corresponding to immunoglobulins present in the same species as the intended recipient of the fusion protein. In other words, human immunoglobulin constant heavy region sequences should be used when the Fc fusion construct (the Fc-antigen and/or the Fc-adjuvant fusion protein) is to be administered to a human. Nucleotide and amino acid sequences of human Fc IgG are disclosed, for example, in Ellison et al. (1982) NUCLEIC ACIDS RES. 10:4071–4079. Likewise, murine Fc sequences should be used when the Fc fusion is to be administered to mice. Nucleotide and amino acid sequences of murine Fc IgG2a are disclosed, for example, in Bourgois et al. (1974) EUR. J. BIOCHEM. 43:423–435. The same logic would be applied if the Fc fusion proteins were to be administered to other animals including pets, for example, cats and dogs, and farm animals, for example, cows and horses.

As used herein, the term "preselected antigen" is understood to mean any protein or fragment thereof, or polypeptide which, either alone or in combination with other reagents, is capable of inducing an immune response in a mammal. It is contemplated that any preselected antigen of interest may be included in the Fc-antigen fusion protein of the invention. In a preferred embodiment, the preselected antigen is selected from the group consisting of a prostate-specific membrane antigen (PSMA); an ectodomain of a cytokine receptor, for example, an ectodomain of the human IL-4 receptor; a tumor-specific antigen (for example, an antigen that is upregulated or is otherwise present at elevated levels in a tumor cell relative to a normal cell); and a viral protein, for example, a protein encoded by the genome of the human immunodeficiency virus (HIV).

As used herein, the term "adjuvant" is understood to mean any substance that is capable of acting as an immunomodulator, by, for example, enhancing an immune response (either humoral or cellular) against the preselected antigen. As used herein, the term "humoral" immunity is understood to mean immunity mediated by antibodies disposed in body fluids, for example, plasma or lymph, whereas the term, "cellular" immunity also referred to in the art as "cell-mediated immunity" is understood to mean immunological reactions initiated by T lymphocytes and mediated by effector T lymphocytes and/or macrophages.

As discussed previously, a variety of chemical adjuvants, for example, Freund's complete adjuvant, may be useful in immunizing non-human mammals. Although widely used in animals to generate high titers of antibody or significant cytotoxic T lymphocyte (CTL) responses, its side effects, for example, tissue scarring, make it unacceptable for human use. Therefore, there is a need to induce strong immune responses without the accompanying inflammation at the injection site. One distinct advantage of using Fc-adjuvant fusion proteins of the invention is the ability to elicit a strong immune response without the need of chemical adjuvants such as Freund's adjuvant.

Preferred adjuvants useful in the practice of the invention comprise an Fc-adjuvant fusion protein or a nucleic acid encoding the same. Preferred adjuvant proteins for inclusion in the Fc fusion proteins include cytokines. As used herein, the term "cytokine" is understood to mean any protein or peptide analog or functional fragment thereof, which is capable of modulating the activity of immune cells, for example: T cells; B cells; macrophages; neutrophils; eosinophils; basophils; dendritic cells; and their precursors, in a mammal. Preferred cytokines include, for example, IFN-γ, IL-2, IL-4, IL-12, IL-18, TNF, and GMCSF. The extracellular domain of CD40 ligand is also a preferred protein to fuse to Fc to form an Fc-adjuvant. When administered with Fc-adjuvant, the antigen in the Fc-antigen fusion protein can elicit an immune response which is stronger than when the Fc-antigen fusion protein is administered without the Fc-adjuvant fusion protein. In some cases, the level of antibody reached after only two immunizations of Fc-antigen with Fc-adjuvant is just as high or higher than that achieved with Freund's adjuvant, and with no detectable skin reactions.

As with the immunoglobulin heavy chain constant regions of the Fc-antigen or the Fc-adjuvant fusion proteins, the adjuvant protein preferably is non- or is only weakly immunogenic in the intended recipient. This can be accomplished by incorporating into the Fc adjuvant fusion proteins, cytokines defined by amino acid sequences corresponding to cytokines isolatable from the same species as the intended recipient. For example, when the Fc adjuvant fusion protein is to be administered to a human, the adjuvant protein (for example, cytokine) preferably is of human origin.

Co-administration of the Fc-antigen and Fc-adjuvant fusion proteins, either simultaneously or one after the other, can be used to modulate the type of immune response that is stimulated against the preselected antigen. Two classes of immune response, termed Th1 and Th2, are stimulated in response to different types of infection and involve different cytokines. Th1 mediated immune responses typically are cellular in nature, whereas Th2 mediated immune responses typically are humoral in nature. Accordingly, a Th1 response can be useful in attacking altered cells, such as tumor cells or virus-infected cells, whereas a Th2 response can be useful in attacking extracellular agents such as parasites. Often it is useful to administer cytokines, fused to immunoglobulin heavy chain constant regions, to stimulate either a general immune response, or to initiate or modulate specific Th1 or Th2 responses.

Furthermore, the choice of a particular cytokine present in an Fc-adjuvant fusion protein can influence the class of antibody produced against the preselected antigen of the Fc-antigen fusion protein. For example, Fc-IL12 stimulates a helper T cell response by stimulating the production of what are known as Th1 cytokines, for example, IFN-γ, IL-2, and TNF, which promote potent cellular immunity and the production of the IgG2a class of antibody. Conversely, Fc-IL-4 stimulates the production of Th2 cytokines, for example, IL-5, IL-6, IL-10, and IL-4 which promote humoral immunity.

As discussed previously, in a preferred embodiment, the method comprises administering the Fc-antigen fusion protein or the nucleic acid encoding the Fc-antigen fusion protein in combination with an Fc-adjuvant fusion protein. By using two fusion proteins, each containing an immunoglobulin heavy chain constant region, it is possible to co-localize both the preselected antigen and the adjuvant protein (for example, a cytokine) at the same or similar cell types in the mammal. For example, macrophages, B cells, granulocytes and dendritic cells express Fc receptors on their cell surface. Accordingly, by co-administering Fc-antigen and Fc-adjuvant fusion proteins capable of binding Fc receptors, it is possible to co-localize the antigen of the antigen-fusion protein and the adjuvant of the adjuvant fusion protein at the same cellular compartment of APCs. The adjuvant can then enhance or otherwise modulate the immune response in the vicinity of the preselected antigen.

Combinations of Fc-cytokines may also be used in a synergistic manner to stimulate a general response, and then influence whether a cellular (Th1) or humoral (Th2) response occurs. For example, Fc-GMCSF is a potent general stimulator of immune responses. However, in order to modulate the response further toward cellular or Th1 mediated immunity, an Fc-IL12 or Fc-IFNγ adjuvant protein, for example, can be co-administered with Fc-GMCSF. In order to promote a more humoral or Th2 mediated response, an Fc-IL4 adjuvant protein, for example, can be co-administered with Fc-GMCSF to module the response toward the generation of Th2 cells. Other Th1- or Th2-promoting cytokines, used as fusions to Fc, may also be employed depending on the precise nature of the physiological response desired. It is contemplated that this general approach can also be used to modulate existing pathogenic responses such as autoimmunity (a Th1-mediated disease) and allergy (a Th2-mediated disease) by pushing the response toward a particular antigen and away from a detrimental one by immunizing for a new response of the opposite Th type.

In some circumstances, when immunizing an animal with an Fc-antigen fusion protein, it is useful to use nucleic acids as adjuvants. Nucleic acids, for example, oligonucleotides containing a cytosine-phosphodiester link-guanosine (CpG) enriched sequence can bias an immune response toward a Th1 response, and can optionally be used in combination with other adjuvants such as cytokines (see, for example, Brazolot et al. (1998) PROC. NATL. ACAD. SCI. U.S.A. 95:15553–8; Liu et al. (1998) BLOOD 92:3730–6; and Klinman et al. (1997) IMMUNOL. 158:3635–3639). Accordingly, it is contemplated that oligonucleotides containing CpG may be co-administered with an Fc-antigen fusion to achieve an enhanced and appropriately modulated immune response. Such nucleic acid molecules may be of any length, however, nucleotides greater than 8 nucleotides in length are preferred. The nucleic acid sequences preferably comprise the sequence CpG, and more preferably the sequence purine-purine-C-G-pyrimidine-pyrimidine, where cytosines in the central CpG are unmethylated. The frequency of CpG dinucleotides in the adjuvant DNA is preferably at least about 5%, and more preferably about 10%. For example, a double-stranded form of the oligodeoxynucleotide TCCATGACGTTCCTGACGTT (SEQ. ID NO. 22) may be used as an adjuvant. Depending on the type of immune response that is sought, it may be useful to combine the nucleic acid with alum.

The present invention exploits conventional recombinant DNA methodologies for generating the Fc fusion proteins useful in the practice of the invention. The Fc fusion constructs preferably are generated at the DNA level, and the resulting DNAs integrated into expression vectors, and expressed to produce the Fc-antigen or Fc-adjuvant fusion proteins of the invention. As used herein, the term "vector" is understood to mean any nucleic acid comprising a nucleotide sequence competent to be incorporated into a host cell and to be recombined with and integrated into the host cell genome, or to replicate autonomously as an episome. Such vectors include linear nucleic acids, plasmids, phagemids, cosmids, RNA vectors, viral vectors and the like. Non-limiting examples of a viral vector include a retrovirus, an adenovirus and an adeno-associated virus. As used herein, the term "gene expression" or "expression" of an Fc fusion protein, is understood to mean the transcription of a DNA sequence, translation of the mRNA transcript, and secretion of an Fc fusion protein product. Fc fusion proteins each comprising IL2, CD26, Tat, Rev, OSF-2, bIG-H3, IgE Receptor, PSMA, or gp120 have been expressed using expression systems of the type discussed herein. The same or similar expression constructs are disclosed in U.S. Pat. No. 5,541,087 and U.S. Pat. No. 5,726,044.

As an alternative to fusion of proteins by genetic engineering techniques, chemical conjugation using conventional chemical cross-linkers may be used to fuse protein moieties.

Basic vectors useful in the practice of the invention include a selectable marker, for example, a gene encoding dihydrofolate reductase (DHFR), driven by transcriptional regulatory sequences, derived, for example, from the SV40 virus, and bacterial plasmid sequences for selection and maintenance of the plasmid in E. coli. Expression of the Fc-fusion protein sequences are driven by promoter and optionally enhancer sequences, for example, the cytomegalovirus (CMV) promoter and enhancer sequences.

If the Fc-fusion protein or the nucleic acid encoding such a fusion protein is to be administered to humans, the Fc fusion protein-encoding sequences preferably start in a 5' to 3' direction with a "leader sequence" derived, for example, from an antibody light (L) chain, fused in frame with at least a portion of an immunoglobulin heavy chain or mutant form thereof, preferably from the Fcγ1 region of the human immunoglobulin g1 gene. The Fcγ1 region of the immunoglobulin Fcγ1 gene preferably includes at least a portion of the hinge domain and a CH3 domain, and more preferably includes at least a hinge domain, a CH2 domain and a CH3 domain. If the Fc fusion protein is to be administered to mice, preferred nucleic acid sequences encoding the immunoglobulin heavy chain constant region comprise nucleic acid sequence encoding in an 5' to 3' direction, a hinge region, a CH2 domain and a CH3 domain from a mouse IgG2a antibody. The carboxyl terminus of the immunoglobulin heavy chain constant region, if necessary, is modified at the nucleic acid level for ligation, in-frame, with sequences encoding either the preselected antigen (in the case of Fc-antigen) or an immunostimulatory cytokine (in the case of an Fc-adjuvant cytokine ). DNA encoding the secretion cassette can be in its genomic configuration or its cDNA configuration.

The portion of the DNA encoding the signal sequence preferably encodes a peptide segment which directs the secretion of the Fc fusion protein and thereafter is cleaved away from the remainder of the Fc fusion protein. The signal sequence of the invention is a polynucleotide which encodes an amino acid sequence which initiates transport of a protein across the membrane of the endoplasmic reticulum. Signal sequences which are useful in the invention include antibody light chain signal sequences, e.g., antibody 14.18 (Gillies et al. (1989) J. OF IMMUNOL. METH., 125:191), antibody heavy chain signal sequences, e.g., the MOPC141 antibody heavy chain signal sequence (Sakano et al. (1980) NATURE 286:5774), and any other signal sequences which are known in the art (see, for example, Watson (1984) NUCLEIC ACIDS RESEARCH 12:5145).

Signal sequences have been well characterized in the art and are known typically to contain 16 to 30 amino acid residues, and may contain greater or fewer amino acid residues. A typical signal peptide consists of three regions: a basic N-terminal region, a central hydrophobic region, and a more polar C-terminal region. The central hydrophobic region contains 4 to 12 hydrophobic residues that anchor the signal peptide across the membrane lipid bilayer during transport of the nascent polypeptide. Following initiation, the signal peptide usually is cleaved within the lumen of the endoplasmic reticulum by cellular enzymes known as signal peptidases. Potential cleavage sites of the signal peptide generally follow the "(−3, −1) rule". Thus a typical signal peptide has small, neutral amino acid residues in positions −1 and −3 and lacks proline residues in this region. The signal peptidase will cleave such a signal peptide between the −1 and +1 amino acids. Thus, the signal sequence may be cleaved from the amino-terminus of the fusion protein during secretion. This results in the secretion of an Fc fusion protein. Signal peptide sequences useful in the practice of the invention are well known in the art. See, for example, von Heijne (1986) NUCLEIC ACIDS RES. 14:4683.

As would be apparent to one of skill in the art, the suitability of a particular signal sequence for use in the secretion cassette may require some routine experimentation. Such experimentation may include determining the ability of the signal sequence to direct the secretion of an Fc fusion protein and/or determining the optimal configuration, genomic or cDNA, of the sequence to be used in order to achieve efficient secretion of Fc fusion proteins. Additionally, one skilled in the art is capable of creating a synthetic signal peptide following the rules presented by von Heijne, referenced above, and testing for the efficacy of such a synthetic signal sequence by routine experimentation. The terms "signal sequence", "signal peptide," "leader sequence," or "leader peptides" are used interchangeably herein.

It is contemplated that a number of different modes of administration of the Fc fusion proteins or nucleic acid sequences encoding the fusion protein may be used to immunize a recipient against a preselected antigen. Two different applications of the present invention can be used to generate CTL responses, one based on the injection of DNA encoding an Fc-antigen fusion protein, and a second based on administration of Fc-antigen fusion protein capable of delivering the protein to the class I MHC pathway.

The injection of protein antigens typically is used to elicit immune responses in mammals. However, the invention also provides methods of delivering antigen to APCs by DNA injection. A commonly used technique is to inject DNA expression vectors, encoding an antigenic protein, into muscle. Reports suggest that the protein antigen is expressed by muscle cells but that the antigen is not presented to the immune system by these cells. Instead, it is believed that specialized APCs, for example, macrophages and dendritic cells, migrate to the site of injection, pick up and present the antigen through a process that has not yet been elaborated. Use of Fc-antigen fusion protein expression vectors make this process more efficient because the secreted fusion protein binds more efficiently to APCs than native antigen protein.

One consequence of the DNA injection approach is that it can often result in the generation of both humoral and cellular responses. Typically, proteins administered exogenously have a more difficult time entering the pathway for presentation on MHC class I molecules. Nevertheless, administration of the Fc fusion proteins of the invention enhance the generation of cytotoxic cells, likely through MHC class I presentation of the preselected exogenous antigen. Combinations of DNA immunization and protein immunization also can work synergistically to first prime the immune system and then boost the level of response in the form of both antibody production and cytotoxic cellular responses. Co-administration of Fc-adjuvant fusion protein, for example, Fc-IL-2, Fc-GMCSF, Fc-IL-12, and Fc-Flt3 ligand, together with the Fc-antigen fusion protein ensures co-localization of the fusion proteins to the same cellular compartment of the APCs, thereby stimulating a more potent immune response against the preselected antigen.

The compositions of the present invention (i.e., Fc-antigen and/or Fc-adjuvant fusion proteins, or nucleic acid sequences encoding such fusion proteins) may be provided to an animal by any suitable means, directly (e.g., locally, as by injection, implantation or topical administration to a tissue locus) or systemically (e.g., parenterally or orally). Where the composition is to be provided parenterally, such as by intravenous, subcutaneous, ophthalmic, intraperitoneal, intramuscular, buccal, rectal, vaginal, intraorbital, transdermal, intracerebral, intracranial, intraspinal, intraventricular, intrathecal, intracisternal, intracapsular, intranasal or by aerosol administration, the composition preferably comprises part of an aqueous or physiologically compatible fluid suspension or solution. Thus, the carrier or vehicle is physiologically acceptable so that in addition to delivery of the desired composition to the patient, it does not otherwise adversely affect the patient's electrolyte and/or volume balance. The fluid medium for the agent thus can comprise normal physiologic saline (e.g., 9.85% aqueous NaCl, 0.15 M, pH 7–7.4).

Preferred dosages of the Fc-antigen fusion protein per administration are within the range of 50 ng/m$^2$ to 1 g/m$^2$, more preferably 5 µg/m$^2$ to 200 mg/m$^2$, and most preferably 0.1 mg/m$^2$ to 50 mg/m$^2$. Preferred dosages of the Fc-adjuvant fusion protein per administration are within the range of 1 ng/m$^2$ to 0.1 g/m$^2$, more preferably 0.5 µg/m$^2$ to 20 mg/m$^2$, and most preferably 10 µg/m$^2$ to 5 mg/m$^2$. Preferred dosages of nucleic acids encoding the Fc-antigen or Fc-adjuvant fusion proteins per administration are within the range of 1 µg/m$^2$ to 100 mg/m$^2$, more preferably 20 µg/m$^2$ to 10 mg/m$^2$, and most preferably 400 µg/m$^2$ to 4 mg/m$^2$.

It is contemplated that maximal immunization may be achieved by performing numerous separate immunizations, for example, one to three inoculations about 3 weeks to six months apart. Furthermore, as discussed above, maximal immune responses can be achieved under certain circumstances by alternating between the administration of Fc fusion proteins, and nucleic acids encoding such Fc fusion proteins. It is contemplated that the Fc-antigen fusion protein or the nucleic acid encoding the fusion protein can be administered before, simultaneously with, or after the Fc adjuvant fusion protein or the nucleic acid encoding the Fc adjuvant fusion protein is administered to the mammal. It is contemplated, however, that the optimal modes of administration, dosages and booster regimes may be determined by routine experimentation well within the level of skill in the art.

The invention is illustrated further by the following non-limiting examples.

EXAMPLES

EXAMPLE 1

Construction of Fc-antigen and Fc-adjuvant Expression Vectors

In order to properly test the immunogenicity of the Fc fusion proteins in a mouse model, expression vectors were constructed using nucleic acid sequences encoding mouse IgG2a Fc regions. This reduces the risk of the Fc region of each fusion protein inducing an immune response in the mammal. Furthermore, mouse cytokines were used as fusion partners in Fc-adjuvant fusion constructs because their biological activities can be highly species specific. Thus, vectors reported earlier (Lo et al. (1998) PROTEIN ENGINEERING 11:495–500) were modified (see FIG. 2) by replacing the human IgG1 Fc sequence with sequences from cDNA encoding the mouse IgG2a Fc (U.S. Pat. No. 5,726,044).

The mouse IgG2a Fc sequence was cloned from a mouse spleen cell library by polymerase chain reaction (PCR) amplification. The PCR primers contained adapter sequences for joining a leader sequence at the 5' end, and a unique Sma I/Xma I restriction site at the 3' end for ligation with sequences encoding either antigens or adjuvant cytokines. The antigen and adjuvant (cytokine) sequences were prepared with a 5' Sma I site and maintaining the reading frames between Fc and antigen or adjuvant proteins, and a unique Xho I site positioned just after the translational stop signal.

The resulting DNA construct encoded a light chain leader sequence fused directly to the hinge region of mouse IgG2a H chain, and continuing through the mouse IgG2a CH2 and CH3 exons and the fusion partner (either the antigen or the adjuvant cytokine). Transcription was driven by the CMV promoter/enhancer, which has been found to be useful for expression in most cell types in culture, as well as for expression in muscle and other cell types following DNA injection in vivo. A selectable dihydrofolate reductase (DHFR) marker gene was included into each vector to facilitate selection of stably transfected clones, as were sequences necessary for maintenance of the plasmid DNA in *E. coli*.

The following exemplary Fc-antigen constructs were created by inserting properly adapted sequences between the unique Sma I to Xho I sites in the vector designated, pdCs-muFc, where "mu" indicates that the Fc is of mouse origin:

The ectodomain (the extracellular portion) of the human IL4 receptor (IL-4R) was cloned from human peripheral blood mononuclear cells (PBMC) via PCR amplification. The primers used were 5' GTCCCGGGTATGAAGGTCT-TGCAGGAGC (SEQ ID NO: 1) and 5' CCCCTC-GAGCTAGTGCTGCTCGAAGGGCTCCCTG (SEQ ID NO: 2), which contained the Sma I and Xho I sites, respectively, for insertion into the pdCs-muFc vector. The PCR reaction conditions used for this, and the following clonings, were as follows. Advantage KlenTaq and Polymerase Mix (Clontech, Palo Alto, Calif.), and specific primers were used to amplify the gene(s) of interest. The reaction mixtures contained 10 mM Tris-HCl, pH 8.3, 50 mM KCl, 1.5 mM MgCl2, 0.01% gelatin (w/v), 0.2 mM each of dNTPs, and 1.25 units of KlenTaq in a total volume of 100 ml. Thirty PCR cycles were performed, each cycle consisting of heat denaturation at 94° C. for 1 min, annealing at 42° C. for 45 sec, and primer extension at 72° C. for 1 min. The amplified product then was subcloned into an SK vector (Stratagene, San Diego, Calif.), and its DNA sequence verified by standard sequencing methodologies.

The ectodomain of human prostate specific membrane antigen (PSMA) was cloned from the LnCAP prostate carcinoma cell line (ATCC CRL1740) via PCR using the primers 5' AAGCTTAAATCCTCCAATGAAGC (SEQ ID NO: 3) and 5' CTCGAGTTAGGCTACTTCACTCAAAG (SEQ ID NO: 4), for the sense and anti-sense strands, respectively. The DNA sequence was verified, and the PCR fragment inserted into the pdCs-muFc vector to produce pdCs-muFc-PSMA fusion construct.

The ectodomain of human EpCAM (also known as KS antigen), an epithelial cell surface protein upregulated in most carcinoma cells, was cloned from LnCAP cells via PCR using the primers 5' CCCCGGGTAAACAGGAA-GAATGTGTCTGTG (SEQ ID NO: 5), and 5' CTCGAGT-CATTTTAGACCCTGCATTGAG (SEQ ID NO: 6) for the sense and anti-sense strands, respectively. The DNA sequence was verified by standard sequencing methodologies, and the PCR fragment inserted into the pdCs-muFc vector to produce the pdCs-muFc-EpCAM fusion construct. Another vector was constructed using the EpCAM ectodomain as the N-terminal fusion partner, and in this case the PCR product included the natural leader of the EpCAM cDNA and the mature ectodomain sequence to the boundary of the membrane spanning domain. The 3' end of this PCR product contained an engineered Afl II site for ligation to the 5' Afl II site of the murine Fc fragment. The PCR primers used included 5' TCTAGAGCAGCATG-GCGCCCCGC (SEQ ID NO: 7) and 5' CCTTAAGCAC-CCTGCATTGAGAATTCAG (SEQ ID NO: 8). In this case, the murine Fc lacked a 3' insertion site for inserting a fusion protein, but contained a translation termination signal at the end of the Fc coding sequence.

A relatively conserved portion of the membrane-proximal region of HIV gp41, extending from a Hind III site to the lysine residue adjacent to the membrane-spanning region, was expressed as an Fc fusion protein as an example of a short polypeptide antigen sequence. Although the protein sequence from the HIV IIIB strain was used, the coding sequence was optimized for optimal eukaryotic cell expression by using a codon bias of high GC content. A DNA sequence encoding amino acid residues 626 through 669 having the following sequence: C CCG GGA TCC CTG ATC CAC TCC CTG ATC GAG GAA TCC CAG AAC CAG CAA GAG AAG AAC GAG CAG GAG CTG CTG GAG CTC GAC AAG TGG GCC TCC CTG TGG AAC TGG TTC AAC ATC ACC AAT TGG CTG TGG TAC ATC AAG TGA CTCGAG (SEQ ID NO: 9) was synthesized chemically and ligated into the pdCs-muFc vector. The amino acid sequence of the fused polypeptide was: SLIH-SLIEESQNQQEKNEQELLELDKWASLWN-WFNITNWLWYIK (SEQ ID NO: 10).

Other HIV protein encoding sequences were used to construct Fc-antigen fusion proteins as described earlier (U.S. Pat. No. 5,541,087 and U.S. Pat. No. 5,726,044) using the mouse IgG2a Fc rather than the original human IgG1 Fc. These constructs represent further embodiments of the invention.

A series of Fc-adjuvant (cytokine) fusion proteins comprising the mouse IgG2a Fc and several mouse cytokines was constructed in the same manner as for the Fc-antigen fusion proteins. The specific cytokines and the cloning primers are discussed below.

Mouse IL-2 was cloned from murine peripheral blood mononuclear cells (PBMCs) via PCR using the PCR primers (sense) 5' GGCCCGGGTAAAGCACCCACTTCAAGCTCC (SEQ ID NO: 11), and (antisense) 5' CCCTCGAGTTATTGAGGGCTTGTTG (SEQ ID NO: 12).

Mouse GMCSF was cloned from murine PBMCs via PCR using the PCR primers (sense) 5' CCCGGGAAAAGCACCCGCCCGCTCACCC (SEQ ID NO: 13), and (antisense) 5' CTCGAGTCATTTTTGGCTTGGTTTTTTGC (SEQ ID NO: 14).

Mouse Flt3 ligand was cloned from murine thymus via PCR using the PCR primers (sense) 5' CAAGCTTACACCTGACTGTTACTTCAGC (SEQ ID NO: 15), and (antisense) 5' CTCGAGTCAAGGCTCTGGGAGCTCCGTGGC (SEQ ID NO: 16).

Mouse IL-12p35 was cloned from murine PBMCs via PCR using the PCR primers (sense) 5' CCCCGGGTAGGGTCATTCCAGTCTCTGG (SEQ ID NO: 17), and (antisense) 5' CTCGAGTCAGGCGGAGCTCAGATAGC (SEQ ID NO: 18).

Mouse IL12p40 was cloned from murine PBMCs via PCR using the PCR primers (sense) 5' TCTAGACCATGTGTCCTCAGAAGCTAAC (SEQ ID NO: 19), and (antisense) 5' CTCGAGCTAGGATCGGACCCTGCAG (SEQ ID NO: 20).

All the PCR products, except for the mouse IL-12p40, were cloned as Sma I to Xho I fragments, analyzed by standard DNA sequencing methodologies, and ligated into the pdCs-muFc vector containing murine Fc of IgG2a as its Fc region. The mouse IL-12p40 PCR product was expressed separately (not as an Fc fusion protein) in a vector containing the same CMV promoter enhancer, a light chain leader sequence fused directly to the mature mouse p40 subunit of IL-12, and a neomycin resistance gene in place of the DHFR selectable marker gene in the pdCs-muFc vector. The resulting vector was called pNC-mp40, where the "N" denotes a Neomycin selection gene.

All the plasmid constructs induced synthesis and secretion of the specific fusion proteins by transient expression in human kidney 293 cells. Briefly, plasmids were introduced into human kidney monolayer cells 293 via co-precipitation with calcium phosphate (Sambrook et al. (1989) MOLECULAR CLONING - A LABORATORY MANUAL, Cold Spring Harbor, N.Y.). The cells were left overnight (16 hr), rinsed with PBS, and fed with fresh cell culture medium (DMEM containing 10% fetal bovine serum (FBS)). After an additional 2–3 days, the culture medium was tested for secreted fusion proteins by an Fc specific ELISA (Gillies et al. (1989) J. IMMUNOL. METHODS 125:191) using antibodies specific for mouse IgG-Fc protein. In the case of the mouse Fc-IL12, both the Fc-p35 and p40 expression plasmid DNAs were transiently expressed in the same cell culture so that the heterodimeric cytokine fusion protein assembled before secretion out of the cell (Gillies et al. (1998) J. IMMUNOL. 160:6195).

Thereafter, stably transfected cells expressing the various Fc fusion proteins were generated by introducing linearized DNA into mouse NS/0 myeloma cells by standard electroporation techniques. Briefly, cells were suspended in a Gene Pulser Cuvette (BioRad) at $10^7$ cells/ml and 0.5 ml of the suspension was mixed with 10 µg of DNA, and the mixture chilled on ice for 10 minutes. Electroporation was performed using a Gene Pulser (BioRad) with settings of 0.25 V and 500 µF. Cells were allowed to recover on ice for 10 minutes, after which they were resuspended in growth medium and transferred to 96-well plates. The cells were fed every 2–3 days with selection medium containing 0.1 µM methotrexate beginning 2 days after electroporation. Drug-resistant colonies growing in the 96-well plates were tested for expression by the Fc ELISA protocol.

For expression of the mouse Fc-IL12 fusion protein, a transfected cell line of NS/0 already expressing the p40 subunit of mouse IL-12 was transfected, as described above, with the mouse Fc-p35 subunit expression vector. The p40 expressing line was obtained by electroporation of NS/0 cells with the pNC-mp40 vector, described above, and selection in medium containing the Neomycin analog G418 (Life Sciences Technologies). After the second transfection, surviving cell clones were screened by an Fc ELISA and a mouse IL-12 ELISA (Genzyme, Cambridge, Mass.).

The structural integrity of the resulting fusion proteins was tested by SDS-polyacrylamide gel electrophoresis (SDS-PAGE). Initially, the fusion proteins were bound to a small volume (10–20 µl per ml of media) of protein A Sepharose (Repligen, Needham, Mass.). The bound material was washed with PBS containing Tween-20 (0.01%), then eluted in gel buffer containing SDS, and then boiling for 2 minutes in the presence of 5% 2-mercaptoethanol. The reduced proteins then were run on pre-cast SDS-PAGE gels and stained with Coomassie blue. Large scale purifications from stable cell clones were performed using protein A Sepharose columns (Repligen, Needham, Mass.) in accordance with the manufacturer's instructions.

EXAMPLE 2

Immunogenicity of an Fc-antigen and the Effect of Chemical or Fc-cytokine Adjuvants on Antibody Production The mouse Fc-huIL-4R alpha subunit construct prepared in Example 1 was used as an antigen to test the potential APC-targeting effect of these proteins in an animal model. The ectodomain of the IL-4R alpha subunit represents a fairly conserved molecule between species, having greater than 50% sequence identity between humans and mice.

Groups of mice were injected subcutaneously with 50 µg of the Fc-antigen fusion protein (Fc-IL-4R) in either PBS or emulsified in Freund's Complete Adjuvant (CFA). Some groups also received a 5 µg dose (mixed with the Fc-IL-4R) of an Fc-adjuvant protein of either Fc-IL2 or Fc-GMCSF. Two weeks later, the mice were injected with the same mixture but administered to the peritoneal cavity. The CFA formulation creates micelles which serve to form a source of slow-released antigen, allowing for continuous stimulation of the immune system. Mycobacterial proteins in the CFA also induce a strong inflammatory response through cytokine stimulation, thereby further enhancing an immune response. CFA, however, causes severe side effects including skin damage, making it unusable in humans. The mixtures with the Fc-adjuvant fusion proteins in PBS, however, did not appear to elicit any visible skin reaction or any other overt signs of toxicity in any of the animals.

Two weeks after the boost (i.e., day 28 after the first injection), the animals were bled and sera prepared by allowing whole blood to clot in microfuge tubes, spinning out cells and clotted material at high speed 12000 RPM for 5 minutes, and recovering the supernatant. The resulting sera were diluted with assay buffer (PBS containing 0.01% Tween-20) and tested for antibodies reactive with human IL-4R. An antigen-specific ELISA was performed using 96-well plates coated with human Fc-huIL-4R (100 µl of 5 µg/ml in PBS was added to each well and incubated at 4° C. (overnight). The antigen coated plates then were washed and blocked with blocking buffer (1% BSA, 0.01% Tween-20 in PBS) prior to use. Dilutions of the test sera were incubated in the wells for 2 hours at room temperature, and then the wells were washed eight times with assay buffer. Secondary anti-mouse Fc-specific horse radish peroxidase-conjugated antibody (1:2000 dilution, Jackson ImmunoResearch) was added, and the plates were incubated for another hour. After eight additional washes with assay buffer, a solution of o-phenylenediamine dihydrochloride (OPD) containing 25 mM citric acid, 50 mM $Na_2HPO_4$, pH5 and 0.03% freshly added $H_2O_2$, was added. The reaction was stopped after about 30 minutes by the addition of 100 µL of 4N $H_2SO_4$. The resulting plates were read at 490 nm in a plate reader which automatically subtracted the background reading at 650 nm. The results were plotted as optical density versus dilution of antiserum. Relative antibody titers were determined by the amount serum had to be diluted before the optical density fell below an arbitrarily value of, for example, 1 O.D. unit.

The results of the immunization protocols are shown in FIG. 3. Injection of the mouse Fc-IL-4R fusion protein alone in PBS by this protocol induced an antibody response in only one mouse (FIG. 3B). The addition of CFA, however, resulted in more mice responding but the titers were roughly the same as the responding mouse injected with Fc-IL4R fusion protein alone in PBS (FIG. 3C). Co-administration of the mouse Fc-IL2 adjuvant with Fc-IL4R in PBS induced responses in all animals, however, the amount of antibody produced in each case varied (FIG. 3D). The combination of CFA and the mouse Fc-IL2 adjuvant together (FIG. 3A) resulted in higher antibody titers than either agent alone (FIGS. 3C and 3D). Co-administration of the mouse Fc-GMCSF adjuvant in PBS induced the strongest immune response of all groups (FIG. 3E), including the group that was immunized with the combination of both the Fc-GMCSF adjuvant and CFA (FIG. 3F). In other words, the mouse Fc-GMCSF adjuvant in PBS, when co-administered with the mouse Fc-IL4R antigen, obviated the need to use CFA. It is contemplated that such a method would be more appropriate for use in humans.

EXAMPLE 3

Effect of Fc-GMCSF Adjuvant Dose on Antibody Produced Against the Cancer Antigen, PSMA in the Fc-PSMA Fusion Protein PSMA presently represents an attractive human tumor-associated target antigen because of its restricted normal tissue distribution. PMSA currently is being tested in clinical trials as a tumor vaccine candidate. In this example, the immunogenicity of the PMSA antigen in an Fc-PMSA fusion protein was evaluated.

The mouse Fc-PSMA fusion protein was prepared as discussed in Example 1. Groups of mice were injected subcutaneously with 50 µg of mouse Fc-PSMA in PBS, together with varying concentrations of the Fc-adjuvant fusion protein Fc-GMCSF, and then boosted by intraperitoneal injection 14 days later. Antibody titers were measured via Fc-PSMA antigen capture ELISA, as described in Example 2 for the Fc-IL4R fusion protein. The results were plotted in FIG. 4 as antibody titer (dilution at which the OD is reduced to 1) versus the time after first injection.

Figure 4A:
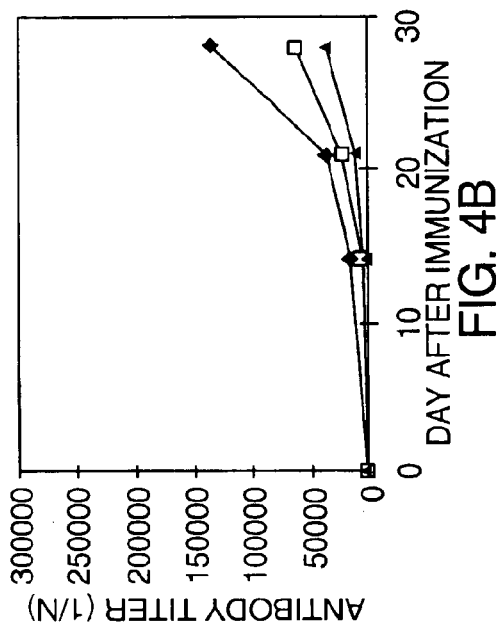
FIGS. 4A–4D are graphs showing the effect of immunizing mice with a human cancer antigen PSMA, in the form of an Fc-antigen fusion protein using varying amounts of Fc-GMCSF as an adjuvant.
Figure 4B:
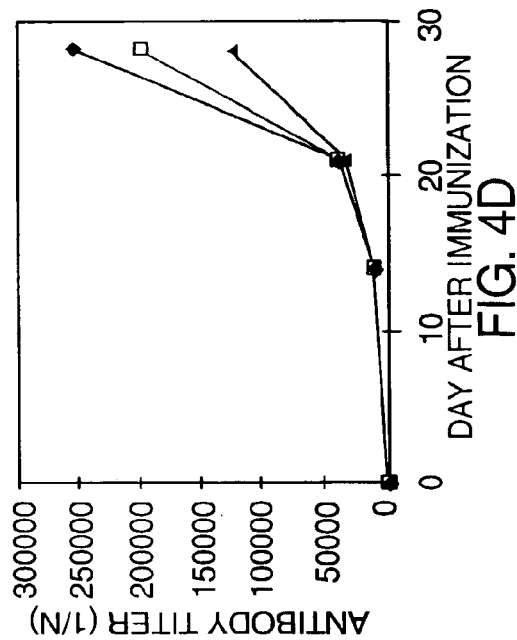
Figure 4C:
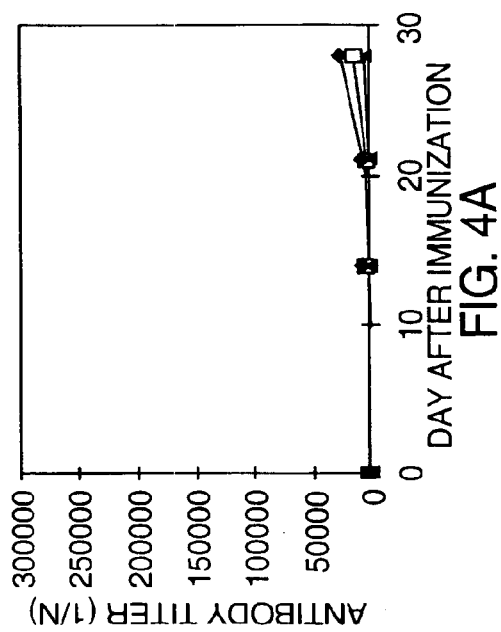
Figure 4D:
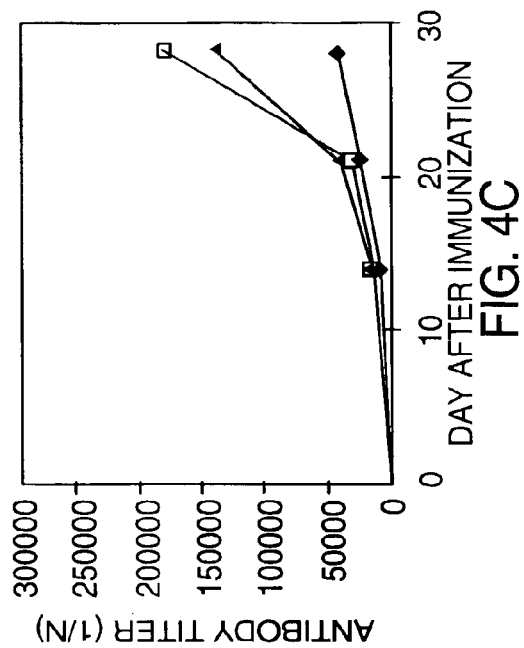

In the absence of Fc-GMCSF, mice had antibody titers against PSMA ranging from 1000 to approximately 20,000 (FIG. 4A). Co-administration of as little as 0.05 µg of Fc-GMCSF, however, resulted in titers ranging from 30,000 to 140,000 (FIG. 4B). Ten-fold increases of Fc-GMCSF further stimulated antibody titers to this cancer antigen (FIGS. 4C and 4D). The highest dose given (5 µg of the Fc-GMCSF fusion protein per mouse) still only represents about 2 µg of GMCSF per injection—a dose with no apparent effect on the mouse skin or any systemic signs that the animal has been immunized (see, FIG. 4D). Furthermore, unlike with CFA, there was no apparent enlargement of the spleen.

EXAMPLE 4

Effect of Fc-mediated Delivery of PSMA on Antibody Response to Immunization

The specific effects of the Fc component of the Fc-antigen and Fc-adjuvant fusion proteins were tested by comparing the induced immune responses in mice injected with the fusion proteins, the non-fused antigen or adjuvant proteins, or with mixtures of the foregoing. The human PSMA system was used for this purpose.

Unfused PSMA was prepared by proteolytic digestion of human Fc-PSMA fusion protein (Lo et al. (1998) PROTEIN ENGINEERING 11:495–500) with plasmin in accordance with the manufacturer's instructions. Released Fc and undigested Fc-PSMA were removed by adsorption to protein A Sepharose (Repligen, Needham, Mass.).

Figure 5A:
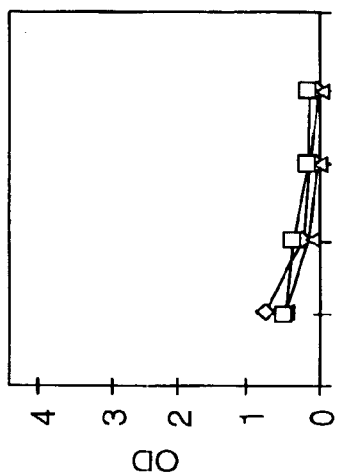
Figure 5C:
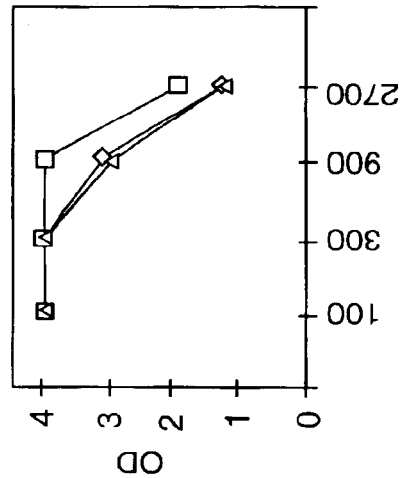

Groups of mice (n=3) were injected with a single subcutaneous dose of 50 µg of PSMA either alone (FIG. 5A), or in combination with 0.2 µg free GMCSF (FIG. 5B) or with 0.5 µg Fc-GMCSF (FIG. 5C) (0.5 µg of Fc-GMCSF contains about 0.2 µg of GMCSF). In another set of mice each mouse was injected with one subcutaneous dose of 50 µg of mouse Fc-PSMA fusion protein alone (FIG. 5D), or together with 0.2 µg free GMCSF (FIG. 5E) or with 0.5 µg Fc-GMCSF (FIG. 5F). All injection formulations were in PBS without chemical adjuvant. Antibodies reactive with mouse Fc-PSMA were measured on day 14 after immunization.

Figure 5B:
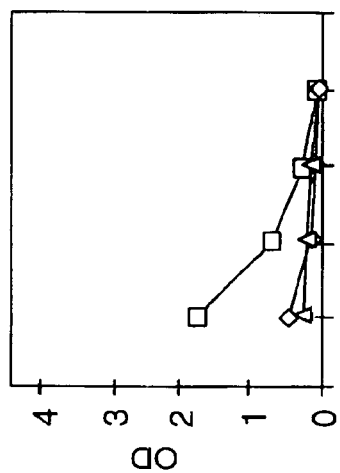
Figure 5E:
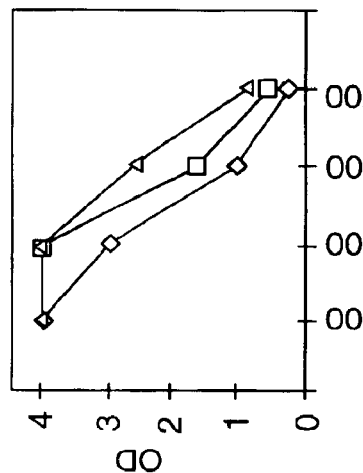
Figure 5A:
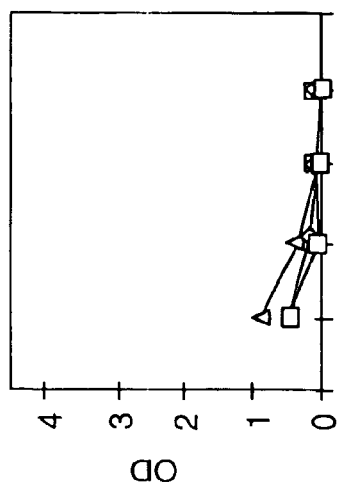
Figure 5D:
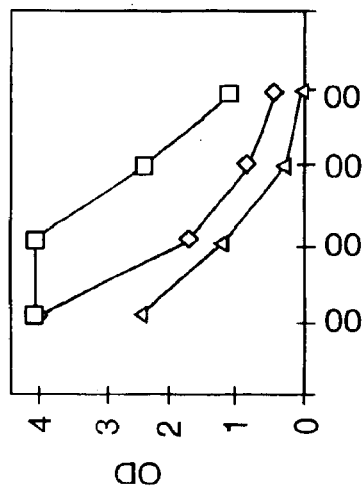

The importance of the Fc component of the Fc-antigen fusion protein in the Fc-PSMA fusion protein for the immunogenicity of PSMA was striking when animals were injected with PBS formulations without chemical adjuvants. There was essentially no primary immune response to the PSMA administered in PBS (FIG. 5A). The addition of GMCSF or Fc-GMCSF to the immunization had very little effect (FIGS. 5B and 5C), except for a weak response in one animal (FIG. 5B). In contrast, animals injected with Fc-PSMA alone showed strong primary immune responses in all cases (FIG. 5D). The addition of free GMCSF to Fc-PMSA boosted the effect slightly (FIG. 5E), but co-administration of both antigen and cytokine as Fc fusion proteins gave the highest level of response (FIG. 5F).

These results indicate that the combination of Fc-antigen and Fc-adjuvant is particularly useful in generating an immune response and show the apparent benefit of co-localizing the antigen and stimulatory cytokine in vivo, presumably to the APCs.

EXAMPLE 5

Comparison of the Adjuvant Effects of the Fusion Proteins Fc-GMCSF or Fc-Flt3L

The ligand for Flt3, also referred to in the art as Flt3 ligand (Flt3L), has been shown to play a critical role on the generation and maturation of dendritic cells (Soligo et al. (1998) BR. J. HAEMATOL. 101:352–63. Dendritic cells, along with tissue macrophage cells, are believed to be the most important APC. Studies in mice have shown that daily injections for 10 days increase the number and APC activity of dendritic cells recoverable from lymph tissue and spleen, and that these cells are extremely potent at presenting antigen to both $CD4^+$ and $CD8^+$ T cells. The Langerhans cells of the skin are believed to represent one type of dendritic cell capable of presenting antigen after uptake and migration to local lymph nodes. Because it is believed that most dendritic cells do not express the array of Fc receptors typically found on macrophage (e.g. FcγRI), it could not be predicted whether the co-localizing effect of Fc fusion proteins would involve this lineage of APC.

Figure 6:
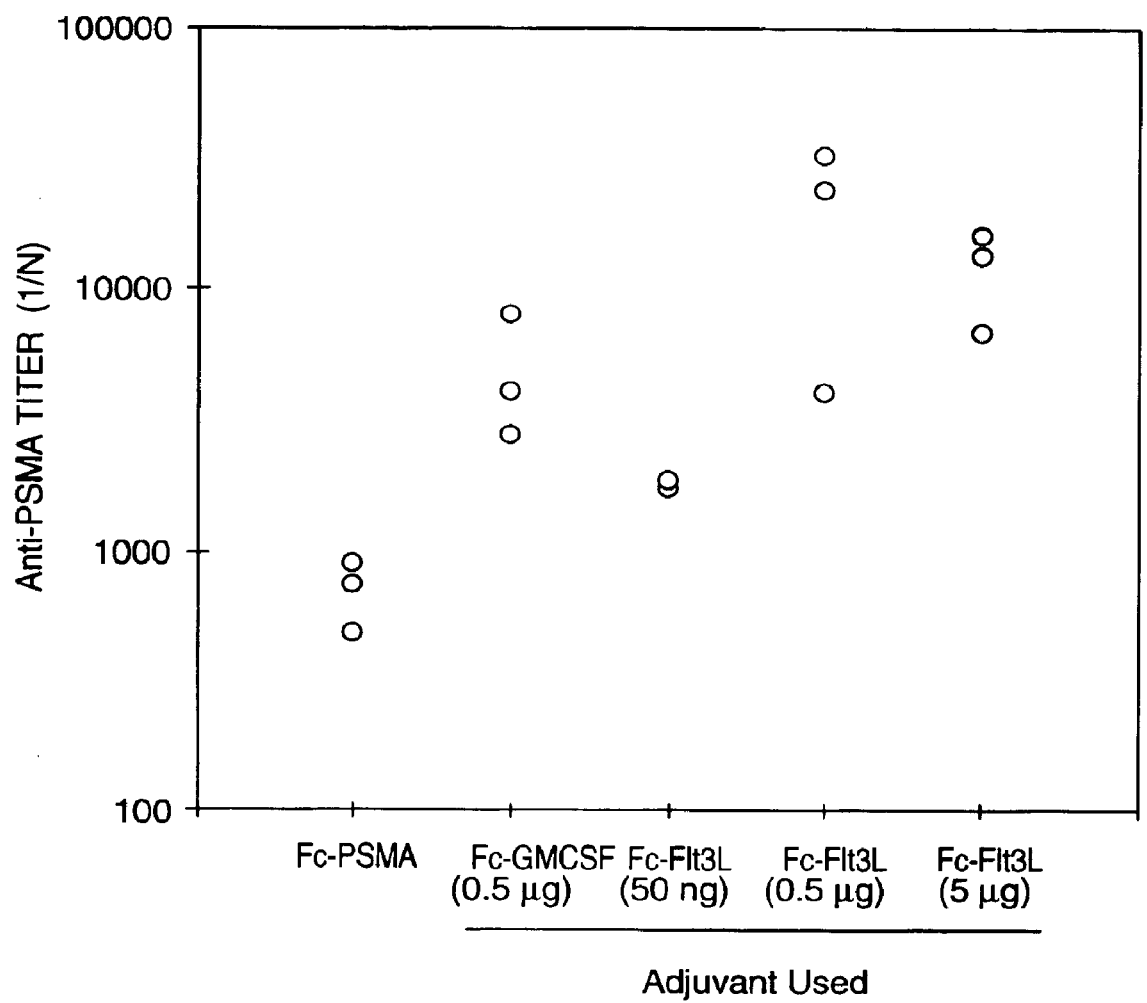
FIG. 6 is a chart comparing the adjuvant effects of Fc-GMCSF or Fc-F3L co-administered with Fc-PSMA on antibody production against human PSMA. All animals received 50 μg of Fc-PSMA either alone or in combination with the indicated Fc-cytokine as an adjuvant. Three mice were tested per experiment.

To test whether Flt-3L could function as an adjuvant, groups of mice were injected with mouse Fc-PSMA and mouse Fc-FLt3L, rather than using the mouse Fc-GMCSF fusion protein (a potent stimulator of macrophage and granulocytes). In this case, any adjuvant effect was expected to be mediated via activation and uptake by dendritic cells, which would ultimately result in an antibody response to PMSA. The results are summarized in FIG. 6.

This study indicates that mouse Fc-Flt3L is a powerful adjuvant that stimulates anti-PSMA antibodies as well as, if not better than, the same dose of Fc-GMCSF. The results support the observation that a combination of an Fc-antigen and an Fc-adjuvant can be particularly potent in inducing an immune response. The results also show that dendritic APC apparently can be targeted with Fc-antigen and Fc-cytokine as well as macrophage APC, suggesting that at least one form of Fc receptor is present on these cells.

EXAMPLE 6

Immune Responses to Fc-EpCAM and EpCAM-Fc Fusion Proteins

Figure 7A:
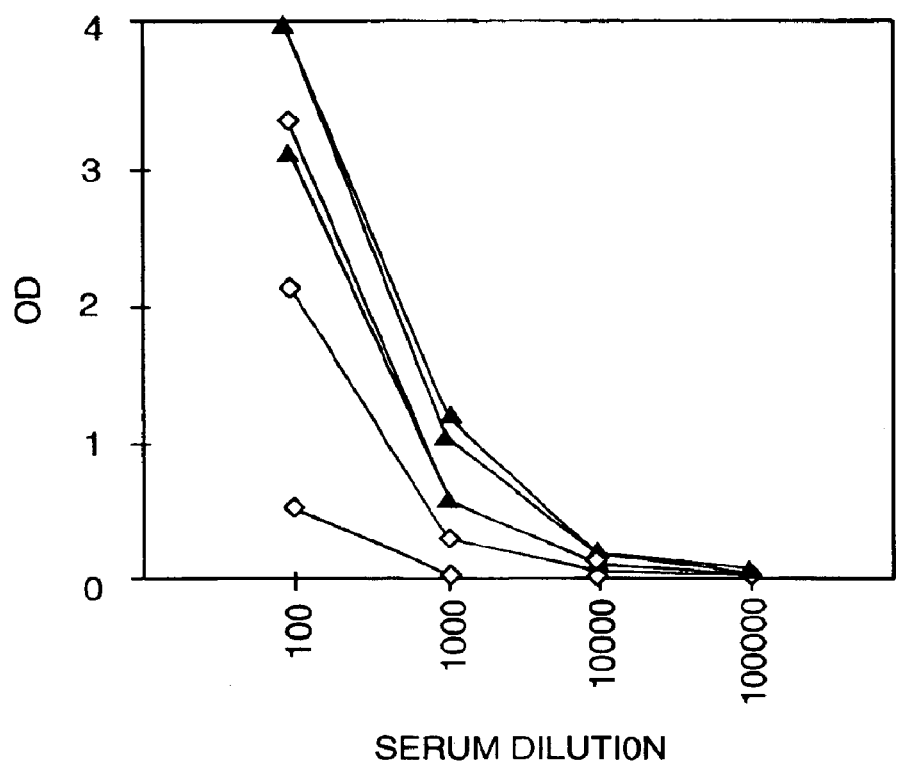
FIGS. 7A–7B are graphs showing the immunogenicity in individual mice of the Fc-EpCAM fusion protein, either alone or in combination with an Fc-GMCSF adjuvant.
Figure 7B:
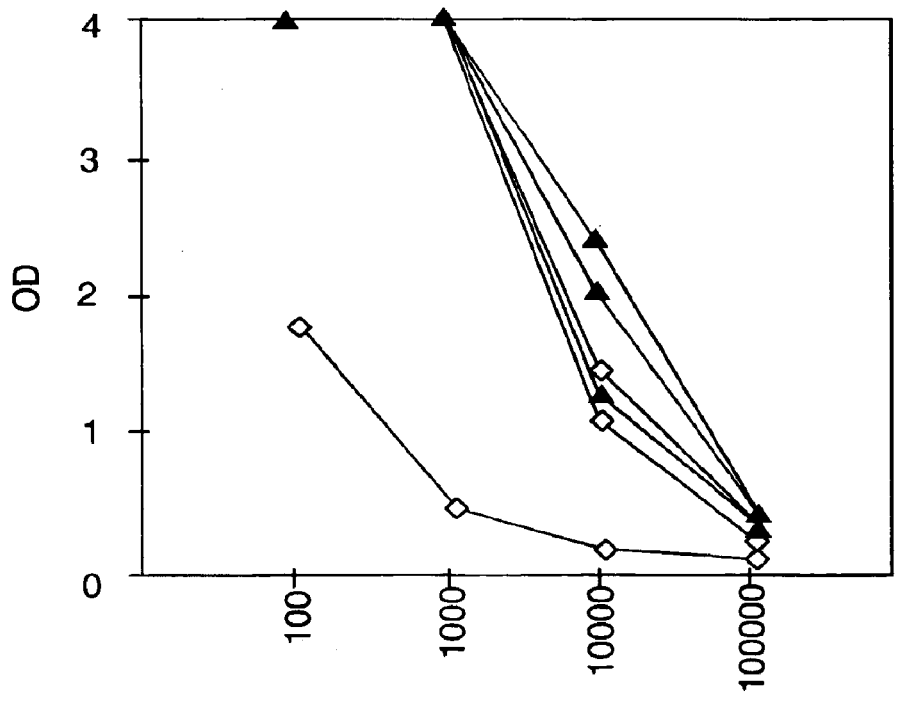

Another potentially important human cancer antigen, EpCAM (also called KSA and 17-1A antigen), was produced as a fusion protein with a mouse IgG2a Fc region using the plasmids and methods as described in Example 1, and was administered either alone, or in combination with Fc-GMCSF as an adjuvant. Mice were injected subcutaneously, and boosted after 3 weeks with 10 μg of Fc-EpCAM and 1 μg of Fc-GMCSF in PBS. Control mice did not receive Fc-GMCSF. Titers of antibodies directed against EpCAM were measured 7 days (FIG. 7A) and 14 days (FIG. 7B) after the boost. The results indicate that Fc-EpCAM, when administered alone, is a potent immunogen (open diamonds), and that Fc-GMCSF can further boost the response to this antigen (closed triangles).

Figure 8A:
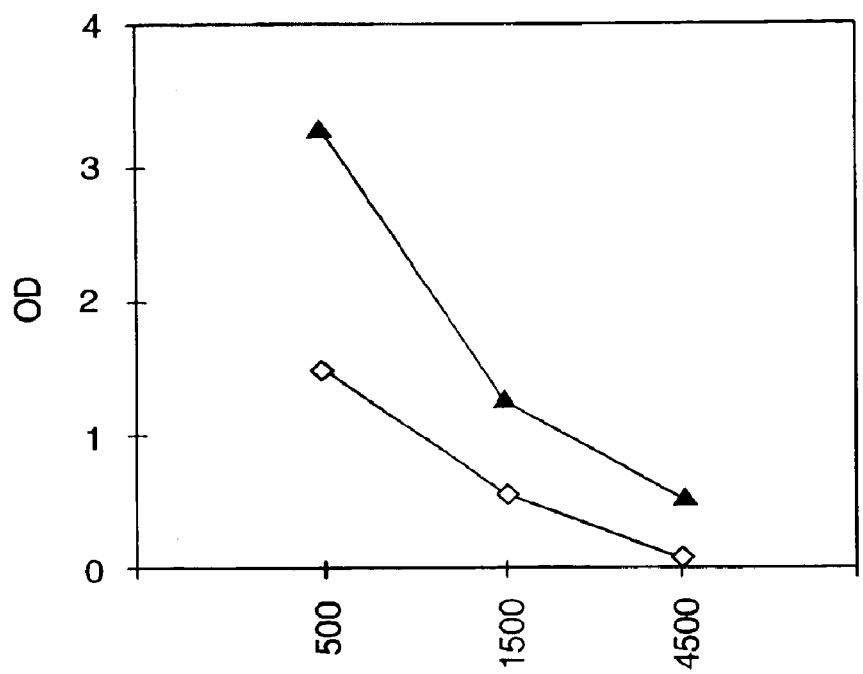
FIGS. 8A–8B are graphs showing the immunogenicity in mice of the EpCAM-Fc (reverse orientation of the Fc region and antigen), either alone or in combination with an Fc-GMCSF adjuvant fusion protein.
Figure 8B:
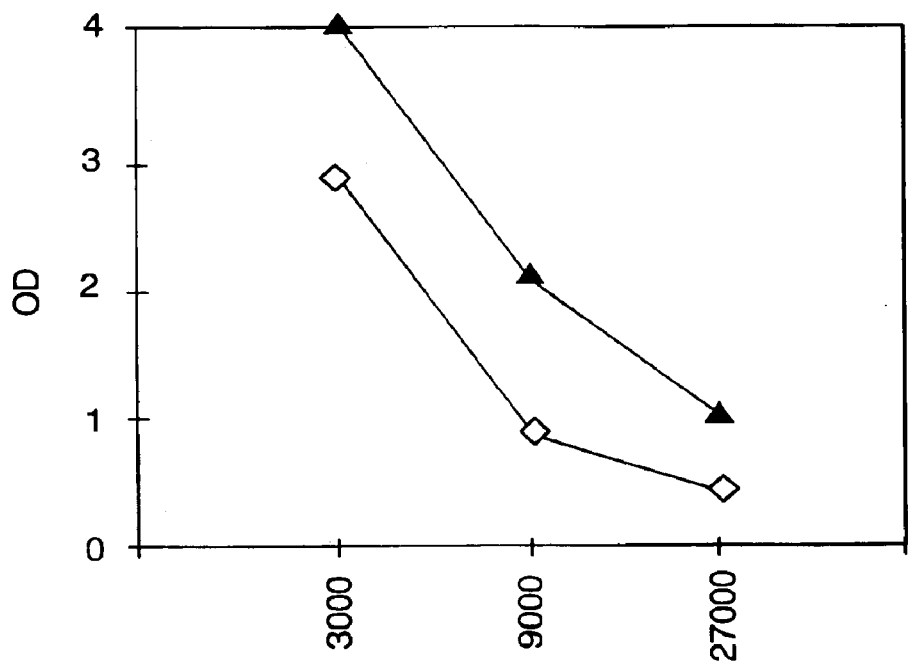

In addition, the EpCAM antigen was expressed in the reverse orientation with respect to the Fc fragment as EpCAM-muFc (see Example 1, FIG. 1B). This molecule was used to immunize Balb/c mice by subcutaneous injection. Higher doses of EpCAM-Fc fusion protein were used (25 μg per dose), and the amount of adjuvant (2.5 μg Fc-GMCSF) was increased also. Titers of antibodies directed against EpCAM were measured 14 days (FIG. 8A) and 21 days (FIG. 8B) after immunization. The EpCAM-Fc fusion protein alone was quite immunogenic in the absence of Fc-GMCSF (FIGS. 8A and 8B, (open diamonds)). The addition of the Fc-cytokine improved antibody titers by about 3-fold (FIG. 8A and 8B, (solid triangles)).

In order to test whether the immune response against EpCAM could protect mammals from tumor cells expressing this antigen, non-immunized mice or those immunized with EpCAM-Fc fusion protein (and in some cases Fc-cytokines) were injected in the tail vein with $10^5$ CT26 mouse colon cancer cells transfected with human EpCAM (Gillies et al. (1998) J. IMMUNOL. 160:6195). Twenty one days later, the animals were sacrificed and the extent of lung metastases estimated by (1) staging in terms of lung surface coverage; and (2) by weighing the lungs and comparing them to normal animal lungs to determine the differential weight increase attributable to tumor mass. Results summarized in Table 1 show that all of the immunized mice showed statistically significant reductions in tumor metastases compared to the control mice, including animals immunized with the EpCAM-Fc fusion protein alone. Similar results were achieved using the Fc-EpCAM fusion protein as the antigen.

TABLE 1

| Treatment Group | Metastatic Score | Av. Lung Weight (mg) |
|---|---|---|
| Control | 4, 4, 4, 1, 1, | 412 +/− 130 |
| EpCAM-Fc | 0, 0, 0, 0, 0 | 210 +/− 21 |
| EpCAM-Fc + Fc-GM | 0, 0, 0, 0, 0 | 240 +/− 19 |
| EpCAM-Fc + Fc-IL2 | 0, 0, 0, 0, 0 | 230 +/− 19 |

Metastatic scores were based on surface coverage of lungs using the following rankings: 1=1–25% coverage; 2=26–50% coverage; 3=51–75% coverage; and 4=76–100% coverage.

EXAMPLE 7

Combination of Antigen-Fc and Cytokine Adjuvant in a Single Fusion Protein

The protein described in Example 6, EpCAM-Fc, exemplifies an N-terminal antigen, linked to an immunoglobulin Fc region as the carboxyl protein domain. This protein, and others like it, can be co-administered with Fc-adjuvant fusion proteins, e.g., Fc-cytokines, to boost the immune response to the antigen. Alternatively, the antigen, the immunoglobulin heavy chain constant region and the adjuvant protein (for example, cytokine) can be produced as a single fusion protein, for example, as an EpCAM-Fc-GMCSF fusion protein.

Figure 9:
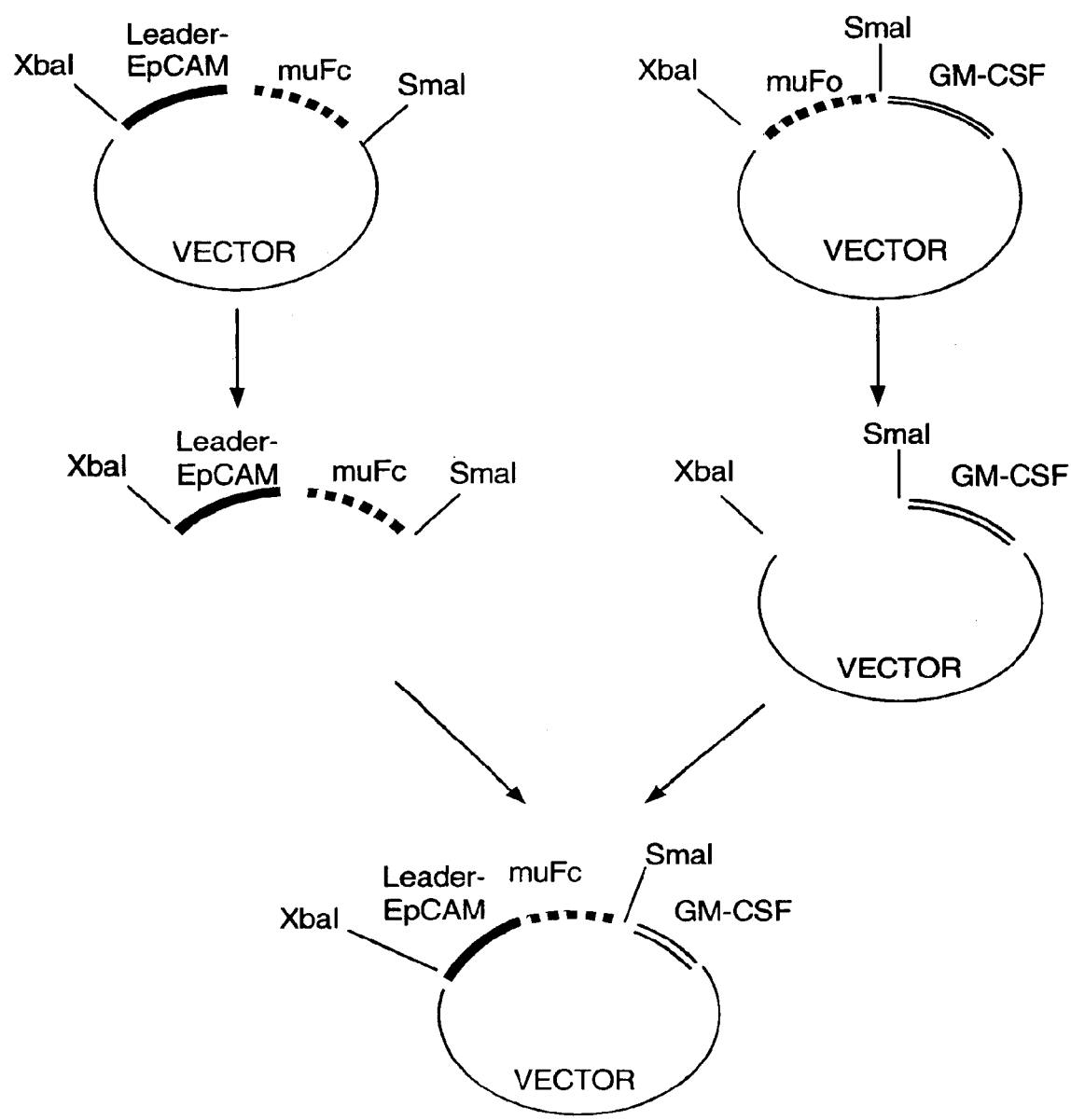
FIG. 9 shows a chart for constructing a plasmid vector encoding an EpCAM-Fc-GMCSF fusion protein. In this case, the antigen EpCAM is fused to the amino terminal end of the immunoglobulin heavy chain constant region (Fc region) and the adjuvant GMCSF is fused to the carboxy terminal end of the Fc region.

The expression plasmid for this protein was constructed using the murine IgG2a Fc and GM-CSF sequences so the construct could be evaluated in a mouse model. A small Xba I to Sma I fragment containing the leader-EpCAM-Fc coding sequences was obtained from the original EpCAM-Fc expression vector (Example 1) and ligated into the large Sma I to Xba I fragment of the Fc-GMCSF expression vector (FIG. 9).

The resulting vector, pdCs-EpCAM-Fc-GMCSF, was introduced into 293 cells using the calcium phosphate precipitation method, for transient expression, and into NS/0 cells by electroporation for stable expression. Stable transfectants were selected by culturing the cells in medium containing methotrexate (0.1 μM). Expressing clones were identified by Fc ELISA (see Example 1) and high-level producers were expanded in culture. The EpCAM-Fc-GMCSF protein was purified from conditioned media by binding to, and elution from protein A Sepharose (Repligen, Needham, Mass.), and structural integrity was analyzed by SDS-PAGE following reduction with 2-mercaptoethanol. The results indicated that the protein had a molecular weight of about 90 kD, as expected for a single-chain fusion of EpCAM, Fc and GMCSF.

In order to compare the relative immunogenicity of the combined fusion protein, mice are injected subcutaneously with equivalent doses of EpCAM-Fc-GMCSF, and the individual fusion proteins in combination: EpCAM-Fc and Fc-GMCSF. The same injections are given 14 days later and serum samples tested for specific antibody reactivity to human EpCAM 7 days after the boost. The same approach may be used for other protein or peptide antigens as well as for other stimulatory cytokines, such as IL-2, IL-12 and Flt3L.

EXAMPLE 8

Immunization with Fc-antigen by DNA Injection

The same expression vectors used for transfection and production of mouse Fc-EpCAM and EpCAM-Fc in mammalian cells (see Example 1) were injected as "naked" plasmid DNA into the hind leg muscle of groups of Balb/c mice. DNA was injected at a concentration of 0.5 mg/ml and a total amount of 100 μg was administered in either PBS or a solution of 25% (w/v) sucrose. Injections were repeated every 3 weeks for a total of 3 injections. Antibody responses were measured at varying times and were quantitated by ELISA using human Fc-EpCAM coated 96-well plates for capture, and using an HRP-conjugated anti-mouse Fc specific polyclonal antibody (Jackson ImmunoResearch) for detection. The data presented in FIG. 10 represents antibody titers recorded 14 days (FIG. 10A), 27 days (FIG. 10B), 55 days (FIG. 10C) and 69 days (FIG. 10D) post injection.

Figure 10B:
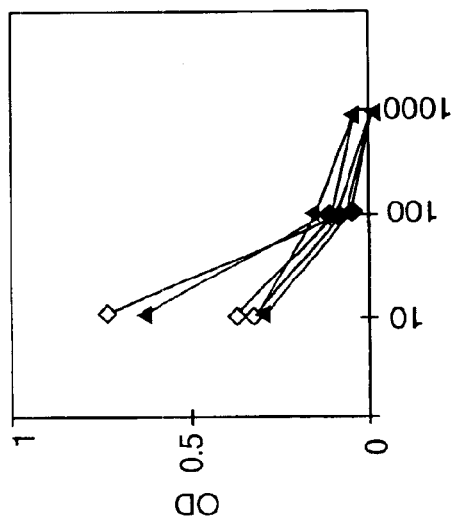
FIGS. 10A–10D are graphs showing antibody titers in mice injected with plasmid vectors encoding the Fc-EpCAM fusion protein using either PBS or a 25% (w/v) sucrose solution as a carrier vehicle.
Figure 10D:
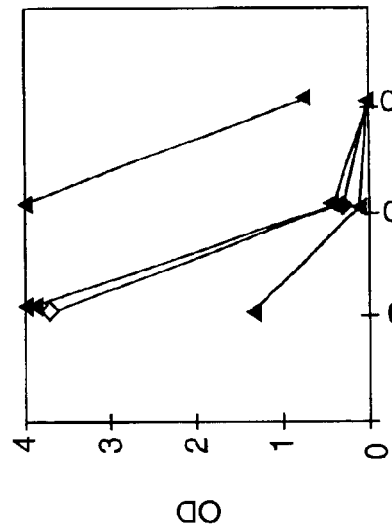
Figure 10A:
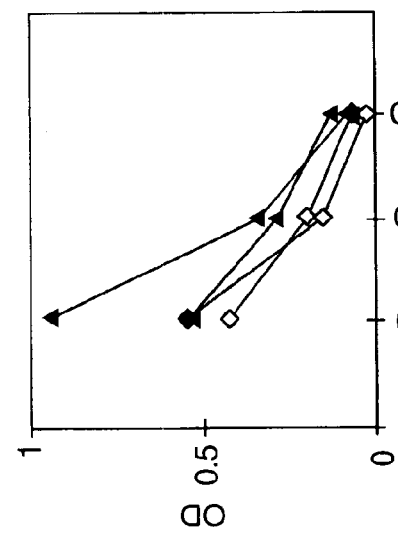
Figure 10C:
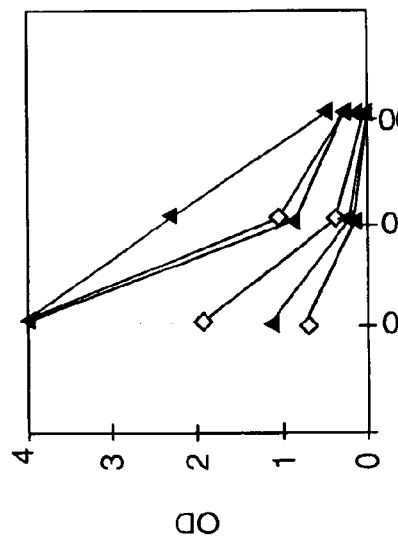

The results presented in FIG. 10 indicate that low titers of specific anti-EpCAM antibody were induced during the first month using both formulations (FIGS. 10A and 10B). Much higher titers were obtained by day 55 (FIG. 10C), and even higher levels by day 69 (FIG. 10D). Similar results were obtained using DNA injection of a vector expressing EpCAM-Fc, although the titers were lower. These data show that an antigen expressed as a fusion molecule comprising a protein antigen and an immunoglobulin Fc region can induce an immune response when introduced by injection of naked DNA, and that persistent antigen exposure leads to delayed responses in most animals.

Figure 11A:
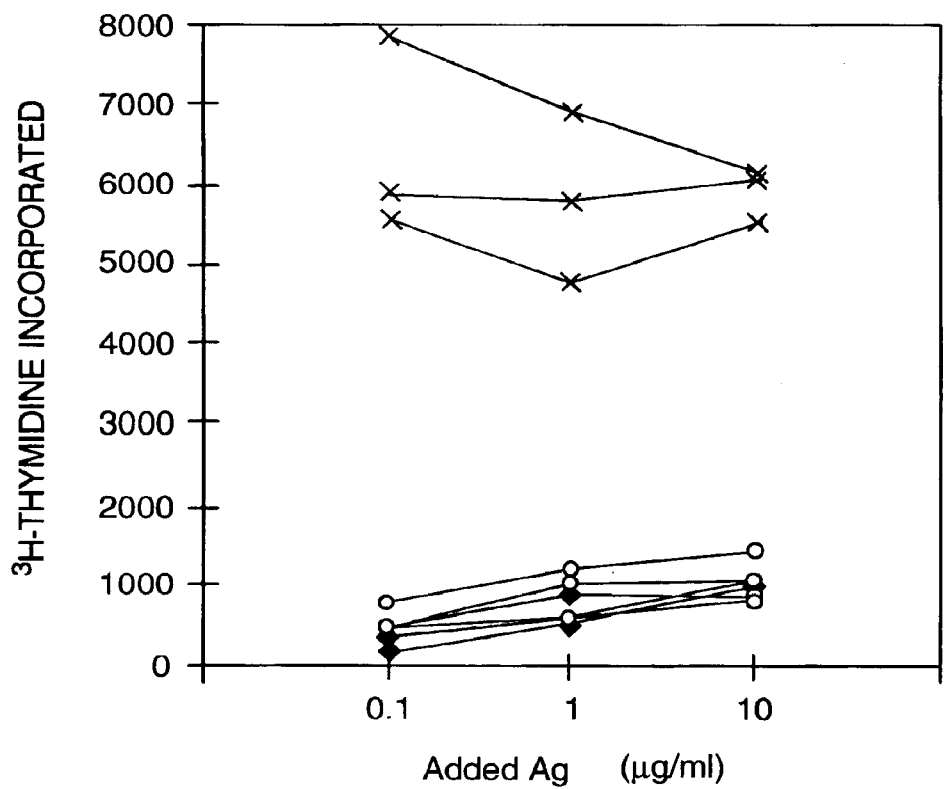
FIGS. 11A–11B are graphs showing the stimulation of $^3$H-thymidine incorporation in response to in vitro stimulation with antigen of splenocytes isolated from mice immunized by DNA vaccination or by protein injection.
Figure 11B:
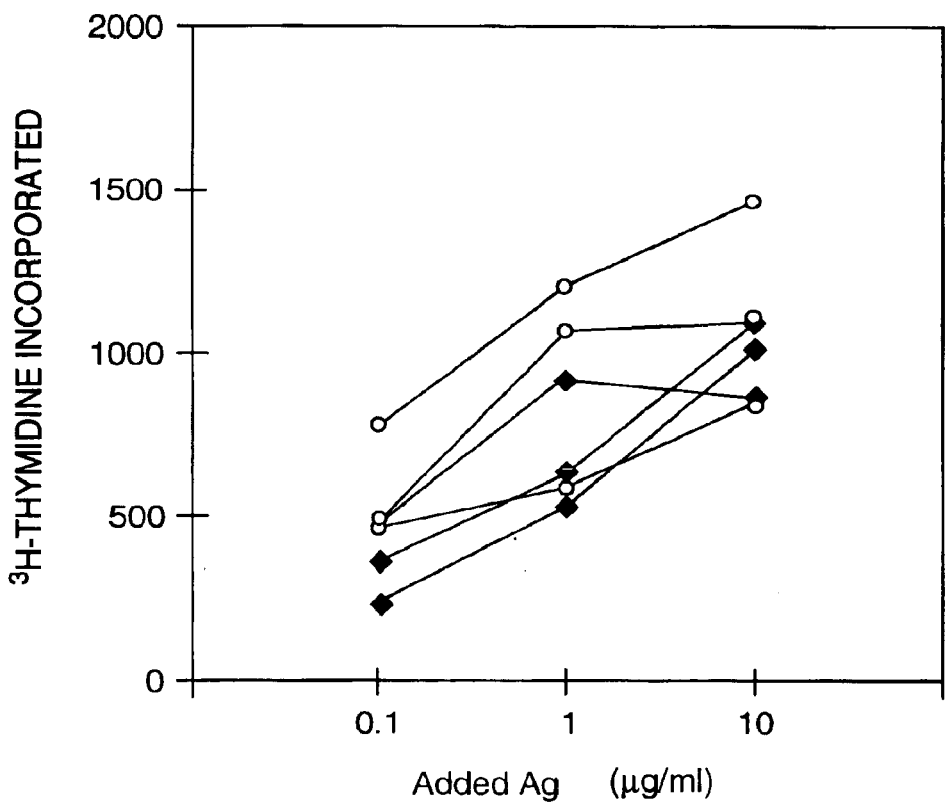

Cellular immune responses were tested by culturing splenocytes from DNA vaccinated or protein immunized mice (70 days after injection) stimulated with different concentrations of Fc-EpCAM protein in vitro. The data present in FIG. 11 (top panel) indicate proliferative response (as measured by $^3$H-thymidine incorporation) to antigen in animals immunized with either Fc-EpCAM protein (crosses) or DNA vaccination with CMVpromoter-EpCAM-Fc (open circles) or CMVpromoter-Fc-EpCAM (closed diamonds) expression vectors. The protein immunized animals showed much greater responses to antigen, even at very low doses. The responses from DNA vaccinated animals (also shown on a different scale in the bottom panel of FIG. 11) were dose-dependent but were lower in magnitude than the protein injected mice. These responses were characteristic of MHC class II restricted CD4$^+$ T cell responses.

In order to test for cytotoxic activity (generally indicative of MHC class I restricted T cell responses), splenocyte cultures from the DNA or protein immunized mice were cultured for 5 days in the presence of about 10 U/ml of IL-2. The effector cells were the cultured splenocytes, and the target cells were either labeled human EpCAM-expressing CT26 colon carcinoma cells (syngeneic for Balb/c mice), or labeled parental (untransfected CT26 cells). The effector and target cells were mixed at different ratios and the extent of lysis was determined. The value of 100% lysis was achieved by incubating the labeled target cells in the presence of detergent and the amount of released label measured..

The results are presented in FIG. 12, where FIG. 12A shows the activity of splenocytes against CT26 cells expressing human EpCAM, whereas FIG. 12B shows the activity of splenocytes against parental CT26 cells. For both figures, the open diamonds represent splenocytes isolated from mice immunized with DNA carrying an EpCAM construct, open squares represent splenocytes isolated from mice immunized with DNA carrying an Fc-EpCAM fusion construct, open triangles represent splenocytes isolated from mice immunized with DNA carrying a EpCAM-Fc fusion construct, and crosses represent splenocytes isolated from mice immunized with Fc-EpCAM fusion proteins.

FIG. 12 shows that although DNA vaccination generated weak cytotoxic responses against both target cells, significantly higher cytotoxicity was seen in the protein-immunized mice. Both the parental CT26 tumor cells and the CT26 tumor cells expressing EpCAM were killed in the assay. The cytotoxicity observed against parental CT26 cells may be because these cells can express high levels of the mouse EpCAM homologue which is about 81% identical to the human protein at the amino acid level. Nevertheless, the Fc-EpCAM protein immunization did generate significant cytotoxic activity against CT26 tumor cells expressing human EpCAM, thereby explaining the potent tumor-protective activity described in Example 6.

EXAMPLE 9

Immunization With An Fc-Fusion Protein Containing a Sub-region of a Protein Cancer Antigen Although some whole proteins may not be useful as antigens for immune therapy, smaller sub-regions of the proteins may be far more effective. For example, proteins may contain domains that are modified post-translationally to make them less immunogenic, thereby reducing immune reactivity to the actual polypeptide components. Large proteins may induce antibodies that react only with non-polypeptide portions of the antigen and that do not mediate antibody-dependent cellular cytotoxicity (ADCC), a potentially important component of anti-tumor immune responses. A good example of this situation is exemplified by the human melanoma-specific chondroitin sulfate proteoglycan (MCSP) antigen, which is expressed on virtually all melanomas as well as several types of brain cancer. This protein is heavily glycosylated and is further modified by attachment of several glycosaminoglycan chains. An antibody known as 9.2.27 (Bumol et al. (1982) PROC. NATL. ACAD. SCi. 79:1245–1249), binds this protein with high affinity, but does not mediate any effector function, either ADCC or complement mediated cytotoxicity (CDC). Even partially humanized (chimeric) forms of this antibody fail to mediate such activities.

In order to elicit more focused responses to more optimal target regions of this large molecule, the putative glycan attachment sites in the protein sequence were identified. (Pluske et al (1996) PROC. NATL. ACAD. SCI. USA 93:9710–9715). A sub-region not far from the cell surface membrane spanning sequence, and some distance away from the glycan attachment sites was selected.

The peptide sequence: QGATLRLDPTVLDAGELAN-RTGSVPRFRLLEGRHGRVVRVPRARTEPGGSQLVE QFTQQDLEDGRLGLEVGRPEGRAPGPAGD (SEQ ID NO: 21) was reverse translated, the resulting DNA sequence synthesized chemically, and ligated into the pdCs-Fc-X expression vector using the same restriction sites used in the earlier Examples. A translation termination site was added to the 3' end, just after the sequence encoding the last amino acid, followed by a unique Xho I site. The final expression plasmid was electroporated into NS/0 myeloma cells and stable transfectants expressing the desired protein were obtained as described in Example 1.

Figure 13:
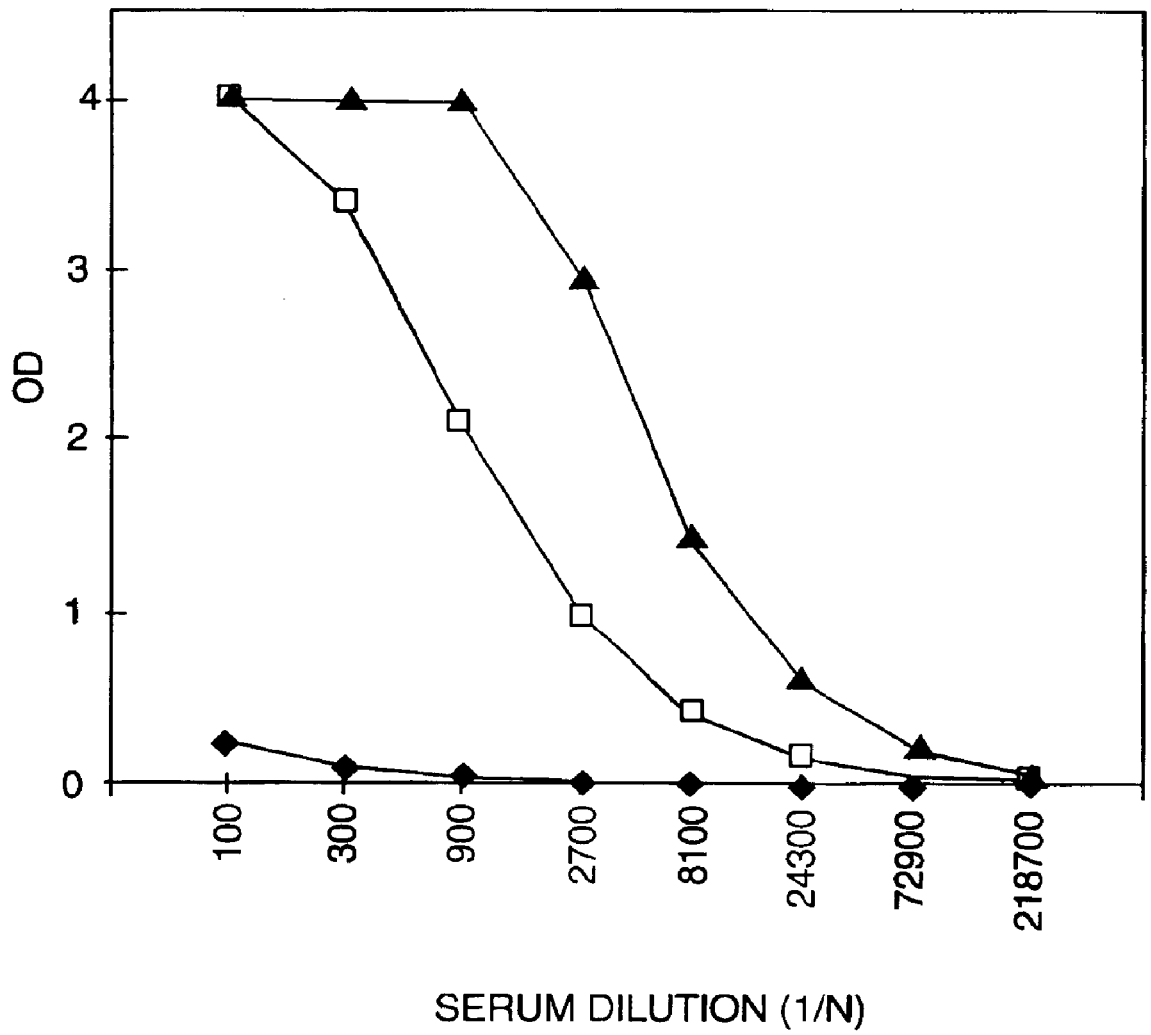
FIG. 13 is a graph showing antibody titers in mice immunized subcutaneously with 50 µg of Fc-MCSP fusion protein in PBS either alone or in combination with 5 µg of Fc-GMCSF as an adjuvant. The solid diamonds represent antibody titers in normal serum, the open squares represent antibody titers in serum of mice immunized with Fc-MCSP fusion protein alone, and the solid triangles represent antibody titers in serum of mice immunized with Fc-MCSP fusion protein in combination with an Fc-GMCSF adjuvant. The levels of antibodies to an antigen were measured by ELISA; the Y-axis indicates the optical density of the ELISA readout.

Fc-MCSP protein was purified from culture supernatants using protein A Sepharose chromatography (Repligen, Needham, Mass.). Antibody titers were measured in Balb/c mice immunized subcutaneously with 50 µg of Fc-MCSP fusion protein in PBS either alone or in combination with 5 µg of Fc-GMCSF as an adjuvant. The results are shown in FIG. 13. The solid diamonds represent antibody titers in a normal serum, the open squares represent antibody titers in serum of mice immunized with Fc-MCSP, and the solid triangles represent antibody titers in a serum of mice immunized with Fc-MCSP and an Fc-GMCSF adjuvant.

Specific immune responses to this sub-region of MCSP were detected by day 14, and increased significantly after booster immunization. The results indicate that mice immunized with both Fc-GMCSF and Fc-MCSP stimulated higher antibody titers against MCSP (solid triangles) than mice immunized with Fc-MCSP alone (open squares).

EXAMPLE 10

Immunization With an Fc-Fusion Protein Containing a Viral Antigen

Development of an effective vaccine against human immunodeficiency virus (HIV), the virus that causes AIDS, is one of the most important goals in vaccine research. Recently, several reports have indicated that certain properties of the virus envelope serve to trick the immune response into responding to irrelevant epitopes, thereby masking important and potentially neutralizing regions of the virus particle. These include the presence of highly immunodominant antigenic regions that serve as decoys, and extensive glycosylation that physically masks and reduces the immunogenicity of important epitopes (Wyatt et al. (1998) NATURE 393:705–11).

One possible way to circumvent the decoy mechanism is to express small regions of the virus envelope gene to avoid immunodominant responses that are not protective, and to induce a neutralizing response. One problem with small subunit vaccines is the reduced immunogenicity either as a synthetic peptide or a small protein. One approach has been to couple the proteins or peptides to immunogenic carrier proteins such as keyhole limpet hemocyanin (KLH). This induces a strong response to KLH as well due to the protein or peptide. Another approach is to make a fusion protein with Fc as described in Example 1 for a subregion of, for example, the ectodomain of gp41 (the anchoring domain of the viral envelope, gp160). Unlike other carriers, the immunoglobulin region is seen as "self", thereby minimizing any immunodominance effect.

The Fc-gp41pep626 fusion construct contained a 44 amino acid polypeptide fused to the carboxyl terminus of a mouse immunoglobulin Fc region. The sequence of HIV strain IIIB in this region contains a signal for N-linked glycosylation, so that the Fc-gp41pep626 fusion protein, produced in either 293 cells by transient expression, or in NS/0 myeloma cells by stable transfection, showed a high degree of variation in mobility on SDS-PAGE analysis thereby indicating heterogeneity in the extent of glycosylation.

Figure 14A:
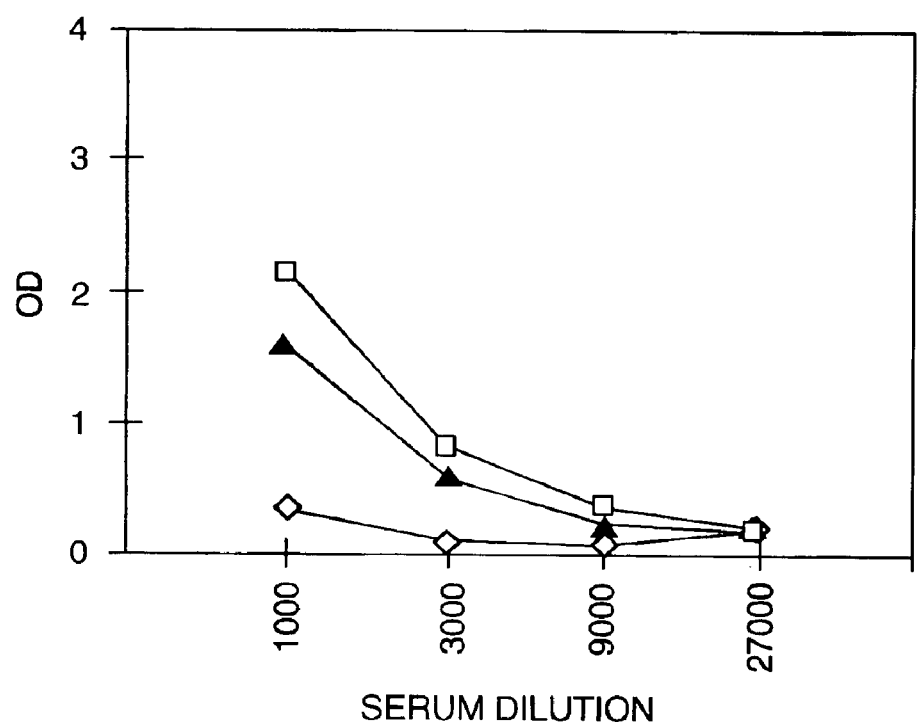
FIGS. 14A–B are graphs showing antibody titers in mice immunized with Fc-gp41pep626 fusion protein, either alone or in combination with an Fc-cytokine adjuvant.
Figure 14B:
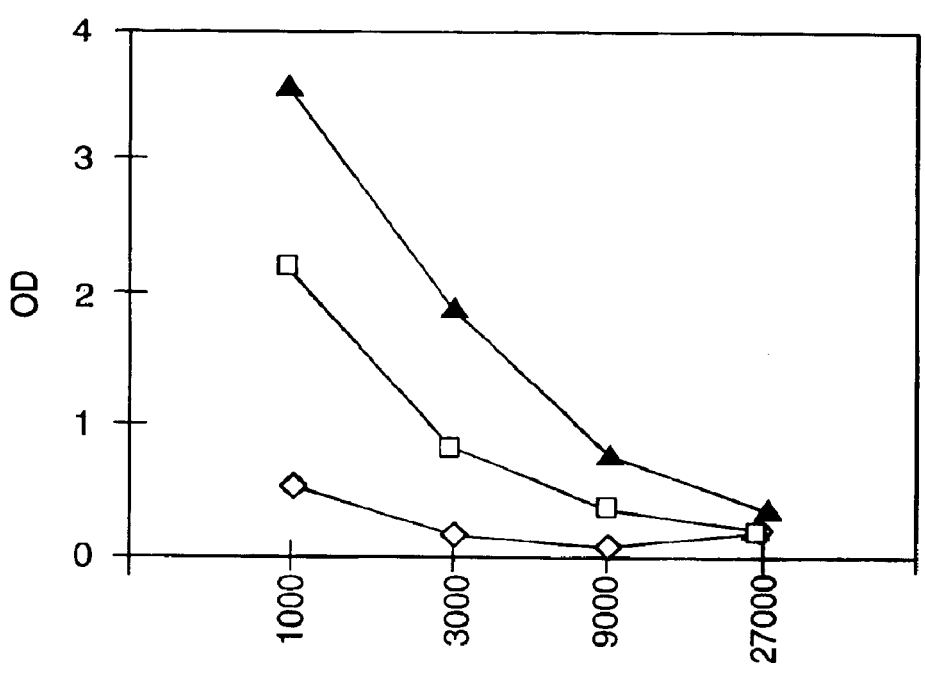

Despite the fact that this viral antigen was quite small (44 amino acid residues in length) and was heterogenously glycosylated, it was possible to elicit an immune response in Balb/c mice (see, FIG. 14). In this case, groups of five mice were injected intradermally with 25 µg of Fc-gp41pep626 on day 1, and twice more at two week intervals, either alone (open diamonds) or in combination with 2.5 µg of the Fc-adjuvant fusion proteins, Fc-GMCSF (open squares) or Fc-IL2 (solid triangles). FIGS. 14A and 14B represent antibody titers achieved 7 and 33 days after a second boost, respectively.

The immune responses were more dependent on the co-administration of Fc-cytokines, and took longer to reach a high titer. It is contemplated that higher immune responses may be elicited using modifications of this sequence that do not contain the glycosylation signal (in fact, many strains do not encode this site) or by enzymatically removing the carbohydrate side chains in vitro.

EXAMPLE 11

Adjuvant Activity of an Fc-Fusion Protein Containing the Extracellular Domain of a Cell-Surface Molecule To construct Fc-adjuvant fusion proteins, it is sometimes useful to fuse to Fc the extracellular domain of a protein that can be membrane-bound. For example, CD40 ligand (CD40L) is fused at the N terminus of C terminus to Fc. A linker is optionally used.

CD40L is useful because its receptor, CD40, is expressed on the surface of B cells and is involved in stimulation of B cells by T cells. Like Tumor Necrosis Factor, CD40L is a trimer that causes dimerization or trimerization of its receptor on a cell surface. As a result, intracellular receptor domains are brought into contact and signal transduction results. Also like TNF, CD40L may be membrane-bound but may also be cleaved from the cell surface and function like a cytokine.

An Fc-CD40L fusion protein is co-administered to animals with an Fc-antigen fusion protein. In control experiments, the Fc-CD40L protein and the Fc-antigen protein are administered to different sets of animals. It is contemplated that animals injected with both fusion proteins produce a higher titer of antibodies than animals injected with each fusion protein individually.

Alternatively, a single Fc fusion protein containing both an antigen and a CD40L moiety is used, with optional linkers (L) between the Fc, CD40L, and antigen moieties. The fusion protein may be the N-terminal to C-terminal order Fc-(L)-antigen-(L)-CD40L, FC-(L)-CD40L-(L)-antigen, antigen)L)-CD40L-(L)-Fc, CD40L-(L)-antigen-(L)-Fc, antigen-(L)-Fc-(L)CD40L, or CD40L-Fc-(L)-antigen-(L). The fusion protein comprising Fc, the antigen, and CD40L is injected into animals and antibody titers then are measured. It is contemplated that antibody titers generated by injection of the fusion protein with both CD40L and antigen are higher than the titers obtained by injection of fusion proteins containing only Fc and antigen or Fc and CD40L.

In the above administrations of fusion proteins, animals are injected intravenously, subcutaneously, or by other appropriate modes of administration. The times between the primary and boosting administration of antigens and/or adjuvants and the measurement of antibody titers are as described in the previous examples. Alternatively, standard dosage and assay regimens are used.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

INCORPORATION BY REFERENCE

The teachings of all the patent documents and scientific publications referred to hereinabove are expressly incorporated herein by reference.

What is claimed is:

1. A method for eliciting an immune response against an antigen in a mammal, the method comprising:
administering to the mammal intramuscularly, intravenously, transdermally or subcutaneously, a fusion protein comprising an antigen linked by a polypeptide bond to an immunoglobulin heavy chain constant region whose ability to bind an Fc receptor is not modified by mutation, thereby to elicit an immune response against the antigen, wherein the fusion protein lacks an immunoglobulin variable domain and the antigen is selected from the group consisting of Prostate-Specific Membrane Antigen, an ectodomain of a cytokine receptor, a viral protein and a tumor-specific protein, the antigen of the fusion protein eliciting a stronger immune response in the mammal than the antigen alone.

2. The method of claim 1, further comprising administering the fusion protein in combination with an adjuvant in an amount sufficient to enhance the immune response against the antigen of the fusion protein relative to the immune response against the antigen of the fusion protein administered without the adjuvant.

3. The method of claim 2, wherein the fusion protein and adjuvant are administered simultaneously.

4. The method of claim 2, wherein the adjuvant comprises a fusion protein comprising an immunoglobulin heavy chain constant region linked by a polypeptide bond to an adjuvant protein.

5. The method of claim 1 or 4, wherein the immunoglobulin heavy chain constant region comprises an immunoglobulin hinge region.

6. The method of claim 5, wherein the immunoglobulin heavy chain constant region comprises an immunoglobulin heavy chain constant region domain selected from the group consisting of a CH2 domain, a CH3 domain, and a CH4 domain.

7. The method of claim 5, wherein the immunoglobulin heavy chain constant region comprises a CH2 domain and a CH3 domain.

8. The method of claim 1 or 4, wherein the immunoglobulin heavy chain constant region is an immunoglobulin heavy chain constant region present in the same species as the mammal.

9. The method of claim 8, wherein the immunoglobulin heavy chain constant region is a human immunoglobulin heavy chain constant region.

10. The method of claim 4, wherein the adjuvant protein is a cytokine.

11. The method of claim 10, wherein the cytokine is a cytokine present in the same species as the mammal.

12. The method of claim 11, wherein the cytokine is a human cytokine.

13. The method of claim 1, wherein the mammal is a human.

14. A composition for eliciting an immune response against an antigen in a mammal, the composition comprising:
an adjuvant; and
an antigen fusion protein comprising an antigen linked by a polypeptide bond to an immunoglobulin heavy chain constant region whose ability to bind an Fc receptor is not modified by mutation, wherein the antigen fusion protein lacks an immunoglobulin variable domain and the antigen of the fusion protein is capable of eliciting a stronger immune response in the mammal than the antigen alone, wherein the antigen is selected from the group consisting of Prostate-Specific Membrane Antigen, an ectodomain of a cytokine receptor, a viral protein and a tumor-specific protein, the composition being formulated for intramuscular, intravenous, transdermal or subcutaneous administration.

15. The composition of claim 14, wherein the adjuvant comprises a fusion protein comprising an immunoglobulin constant region linked by a polypeptide bond to an adjuvant protein.

16. The composition of claim 14 or 15, wherein the immunoglobulin heavy chain constant region comprises an immunoglobulin hinge region.

17. The composition of claim 16, wherein the immunoglobulin heavy chain constant region comprises an immunoglobulin heavy chain constant region domain selected from the group consisting of a CH2 domain, a CH3 domain, and a CH4 domain.

18. The composition of claim 16, wherein the immunoglobulin heavy chain constant region comprises a CH2 domain and a CH3 domain.

19. The composition of claim 14, wherein the adjuvant comprises an oligonucleotide CpG sequence.

20. The composition of claim 14, wherein the adjuvant comprises a cytokine.

21. The composition of claim 20, wherein the cytokine is a human cytokine.

22. The composition of claim 14 or 15, wherein the immunoglobulin heavy chain constant region is a human immunoglobulin heavy chain constant region.

23. The composition of claim 15, wherein the adjuvant protein is a cytokine.

24. The method of claim 1, wherein the fusion protein further comprises an adjuvant linked by a polypeptide bond to at least one of the antigen and the immunoglobulin heavy chain constant region.

25. The composition of claim 14, wherein the adjuvant is linked by a polypeptide bond to at least one of the antigen and the immunoglobulin heavy chain constant region.

* * * * *

SEQUENCE LISTING

```
<160> NUMBER OF SEQ ID NOS:  22

<210> SEQ ID NO 1
<211> LENGTH: 28
<212> TYPE: DNA
<213> ORGANISM: Artificial Sequence
<220> FEATURE:
<223> OTHER INFORMATION: Description of Artificial Sequence:IL-4R primer

<400> SEQUENCE: 1
gtcccgggta tgaaggtctt gcaggagc                                          28

<210> SEQ ID NO 2
<211> LENGTH: 34
<212> TYPE: DNA
<213> ORGANISM: Artificial Sequence
<220> FEATURE:
<223> OTHER INFORMATION: Description of Artificial Sequence:IL-4R primer

<400> SEQUENCE: 2
cccctcgagc tagtgctgct cgaagggctc cctg                                   34

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence:PSMA primer

<400> SEQUENCE: 3
aagcttaaat cctccaatga agc                                               23

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence:PSMA primer

<400> SEQUENCE: 4
ctcgagttag gctacttcac tcaaag                                            26

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence:EpCAM primer

<400> SEQUENCE: 5
ccccgggtaa acaggaagaa tgtgtctgtg                                        30
```

-continued

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence:EpCAM primer

<400> SEQUENCE: 6
ctcgagtcat tttagaccct gcattgag                                              28

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence:EpCAM primer

<400> SEQUENCE: 7
tctagagcag catggcgccc ccgc                                                  24

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence:EpCAM primer

<400> SEQUENCE: 8
ccttaagcac cctgcattga gaattcag                                              28

<210> SEQ ID NO 9
<211> LENGTH: 148
<212> TYPE: DNA
<213> ORGANISM: Artificial Sequence
<220> FEATURE:
<223> OTHER INFORMATION: Description of Artificial Sequence:DNA encoding
      amino acid residues 626-669 of HIV IIIB gp41

<400> SEQUENCE: 9
cccgggatcc ctgatccact ccctgatcga ggaatcccag aaccagcaag agaagaacga           60
gcaggagctg ctggagctcg acaagtgggc ctccctgtgg aactggttca acatcaccaa          120
ttggctgtgg tacatcaagt gactcgag                                             148

<210> SEQ ID NO 10
<211> LENGTH: 44
<212> TYPE: PRT
<213> ORGANISM: Artificial Sequence
<220> FEATURE:
<223> OTHER INFORMATION: Description of Artificial Sequence:Fused
      polypeptide from pdC-muFC vector

<400> SEQUENCE: 10

Ser Leu Ile His Ser Leu Ile Glu Glu Ser Gln Asn Gln Gln Glu Lys
  1               5                  10                  15

Asn Glu Gln Glu Leu Leu Glu Leu Asp Lys Trp Ala Ser Leu Trp Asn
             20                  25                  30

Trp Phe Asn Ile Thr Asn Trp Leu Trp Tyr Ile Lys
         35                  40

<210> SEQ ID NO 11
<211> LENGTH: 30
<212> TYPE: DNA
<213> ORGANISM: Artificial Sequence

```
<220> FEATURE:
<223> OTHER INFORMATION: Description of Artificial Sequence:Primers for
      mouse IL2

<400> SEQUENCE: 11
ggcccgggta aagcacccac ttcaagctcc                                          30

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence:Primer for
      mouse IL2

<400> SEQUENCE: 12
ccctcgagtt attgagggct tgttg                                               25

<210> SEQ ID NO 13
<211> LENGTH: 28
<212> TYPE: DNA
<213> ORGANISM: Artificial Sequence
<220> FEATURE:
<223> OTHER INFORMATION: Description of Artificial Sequence:Primer for
      mouse GMCSF

<400> SEQUENCE: 13
cccgggaaaa gcacccgccc gctcaccc                                            28

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence:Primer for
      mouse GMCSF

<400> SEQUENCE: 14
ctcgagtcat ttttggcttg gtttttgc                                            29

<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence:Primer for
      mouse Flt3 ligand

<400> SEQUENCE: 15
caagcttaca cctgactgtt acttcagc                                            28

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence:Primer for
      mouse Flt3 ligand

<400> SEQUENCE: 16
ctcgagtcaa ggctctggga gctccgtggc                                          30

<210> SEQ ID NO 17
<211> LENGTH: 28
<212> TYPE: DNA
<213> ORGANISM: Artificial Sequence
<220> FEATURE:
```

-continued

```
<223> OTHER INFORMATION: Description of Artificial Sequence:Primer for
      mouse IL-12p35

<400> SEQUENCE: 17
ccccgggtag ggtcattcca gtctctgg                                              28

<210> SEQ ID NO 18
<211> LENGTH: 26
<212> TYPE: DNA
<213> ORGANISM: Artificial Sequence
<220> FEATURE:
<223> OTHER INFORMATION: Description of Artificial Sequence:Primer for
      mouse IL-12p35

<400> SEQUENCE: 18
ctcgagtcag gcggagctca gatagc                                                26

<210> SEQ ID NO 19
<211> LENGTH: 28
<212> TYPE: DNA
<213> ORGANISM: Artificial Sequence
<220> FEATURE:
<223> OTHER INFORMATION: Description of Artificial Sequence:Primer for
      mouse IL12 p40

<400> SEQUENCE: 19
tctagaccat gtgtcctcag aagctaac                                              28

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence:Primer for
      mouse IL12 p40

<400> SEQUENCE: 20
ctcgagctag gatcggaccc tgcag                                                 25

<210> SEQ ID NO 21
<211> LENGTH: 83
<212> TYPE: PRT
<213> ORGANISM: Artificial Sequence
<220> FEATURE:
<223> OTHER INFORMATION: Description of Artificial Sequence:MSCP peptide

<400> SEQUENCE: 21

Gln Gly Ala Thr Leu Arg Leu Asp Pro Thr Val Leu Asp Ala Gly Glu
  1               5                  10                  15

Leu Ala Asn Arg Thr Gly Ser Val Pro Arg Phe Arg Leu Leu Glu Gly
             20                  25                  30

Arg His Gly Arg Val Val Arg Val Pro Arg Ala Arg Thr Glu Pro Gly
         35                  40                  45

Gly Ser Gln Leu Val Glu Gln Phe Thr Gln Gln Asp Leu Glu Asp Gly
     50                  55                  60

Arg Leu Gly Leu Glu Val Gly Arg Pro Glu Gly Arg Ala Pro Gly Pro
 65                  70                  75                  80

Ala Gly Asp

<210> SEQ ID NO 22
<211> LENGTH: 20
<212> TYPE: DNA
<213> ORGANISM: Artificial Sequence
<220> FEATURE:
```

```
<223> OTHER INFORMATION: Description of Artificial
      Sequence:oligodeoxynucleotide that may be used as
      an adjuvant

<400> SEQUENCE: 22
tccatgacgt tcctgacgtt                                                    20
```